United States Patent
Hawley et al.

(10) Patent No.: US 10,822,311 B2
(45) Date of Patent: Nov. 3, 2020

(54) PYRIMIDINES AND VARIANTS THEREOF, AND USES THEREFOR

(71) Applicant: Afferent Pharmaceuticals Inc., San Mateo, CA (US)

(72) Inventors: Ronald Charles Hawley, Oakland, CA (US); Prabha Ibrahim, Mountain View, CA (US); Anthony P. Ford, Palo Alto, CA (US); Joel R. Gever, Los Altos, CA (US)

(73) Assignee: Afferent Pharmaceuticals, Inc., San Mateo, CA (US)

(*) Notice: Subject to any disclaimer, the term of this patent is extended or adjusted under 35 U.S.C. 154(b) by 48 days.

(21) Appl. No.: 16/077,904

(22) PCT Filed: Mar. 9, 2017

(86) PCT No.: PCT/US2017/021477
§ 371 (c)(1),
(2) Date: Aug. 14, 2018

(87) PCT Pub. No.: WO2017/160569
PCT Pub. Date: Sep. 21, 2017

(65) Prior Publication Data
US 2019/0389811 A1 Dec. 26, 2019

Related U.S. Application Data

(60) Provisional application No. 62/363,630, filed on Jul. 18, 2016, provisional application No. 62/308,157, filed on Mar. 14, 2016.

(51) Int. Cl.
*C07D 239/48* (2006.01)
*C07D 401/12* (2006.01)
*C07D 403/12* (2006.01)
*C07D 405/12* (2006.01)

(52) U.S. Cl.
CPC ......... *C07D 239/48* (2013.01); *C07D 401/12* (2013.01); *C07D 403/12* (2013.01); *C07D 405/12* (2013.01)

(58) Field of Classification Search
CPC .. C07D 239/56; C07D 495/04; C07D 239/47; C07D 403/12; C07D 239/60; C07M 239/38; A61K 31/506; A61K 31/496; A61K 31/513; A61K 2121/00
See application file for complete search history.

(56) References Cited

U.S. PATENT DOCUMENTS

| | | |
|---|---|---|
| 2,953,567 A | 9/1960 | Hitchings et al. |
| 9,567,318 B2* | 2/2017 | Chiosis ............... C07D 239/47 |
| 9,732,060 B2 | 8/2017 | Kai |
| 10,052,325 B2* | 8/2018 | Chiosis ............... C07D 239/47 |
| 2004/0157893 A1 | 8/2004 | Bebbington et al. |
| 2007/0049610 A1 | 3/2007 | Dillon et al. |
| 2010/0286390 A1 | 11/2010 | Shigeta et al. |
| 2011/0077242 A1 | 3/2011 | Broka et al. |
| 2012/0135993 A1 | 5/2012 | Leach et al. |
| 2019/0055202 A1 | 2/2019 | Hawley |

FOREIGN PATENT DOCUMENTS

| | | |
|---|---|---|
| WO | 2000059893 | * 10/2000 |
| WO | 2000059893 A1 | 10/2000 |
| WO | 2005095359 A1 | 10/2005 |
| WO | 2007025899 A1 | 3/2007 |
| WO | 2007025900 A1 | 3/2007 |
| WO | 2007025901 A1 | 3/2007 |
| WO | 2007025925 A1 | 3/2007 |
| WO | 2008104472 A1 | 9/2008 |
| WO | 2008104474 A1 | 9/2008 |
| WO | WO2014200078 A1 | 12/2014 |
| WO | 2017165255 A1 | 9/2017 |
| WO | WO2017160569 A1 | 9/2017 |

OTHER PUBLICATIONS

CAS Abstract of W. Zhao et al., Yaoxue Xuebao, 22(7), 541-4 (1987).*
Falco et al., 5-Arylthiopyrinnidines. 1, 2, 4-Diannino derivatives; Journal of Organic Chemistry (1961), 26, 1143-6.*
Carter, Identification and SAR of novel diaminopyrimidines. Part 1: The discovery of RO-4, a dual P2X3/PsX2/3 antagonist for the treatment of pain, Bioorganic & Medicinal Chemistry Letters, 2009, 1628-1631, 19.
NPL—PubChem—CID608444—2005.
Jahangir, Alam, Identification and SAR of novel diaminopyrimidines. Part 2: The discovery of RO-51, a potent and selective, dual P2X3/P2X2/3 antagonist for the treatment of pain, Bioorganic & Medicinal Chemistry Letters, 2009, 1632-1635, 19.
NPL—PubChem—CID18762697—2007.

* cited by examiner

*Primary Examiner* — Mark L Shibuya
*Assistant Examiner* — Ebenezer O Sackey
(74) *Attorney, Agent, or Firm* — Yong Zhao; Anna L. Cocuzzo

(57) ABSTRACT

The present disclosure provides pyrimidine compounds and uses thereof, for example, for the treatment of diseases associated with P2X purinergic receptors. In certain aspects, the present disclosure provides P2X3 and/or P2X2/3 antagonists which are useful, for example, for the treatment of visceral organ, cardiovascular and pain-related diseases, conditions and disorders.

16 Claims, No Drawings

PYRIMIDINES AND VARIANTS THEREOF, AND USES THEREFOR

CROSS-REFERENCE TO RELATED APPLICATIONS

The present application is a 371 national phase application of international application no. PCT/US2017/021477, filed Mar. 9, 2017, which claims the benefit of U.S. Provisional Application No. 62/308,157, filed Mar. 14, 2016, and U.S. Provisional Application No. 62/363,630, filed Jul. 18, 2016; hereby incorporated by reference in their entireties.

FIELD

The present disclosure pertains to pyrimidine compounds and variants thereof, as well as the use thereof, for example, for the treatment of diseases associated with P2X purinergic receptors, and more particularly to P2X3 and/or P2X2/3 antagonists usable for treatment of visceral, cardiovascular and pain-related diseases, conditions and disorders.

BACKGROUND

The information provided herein and references cited are provided solely to assist the understanding of the reader, and does not constitute an admission that any of the references or information is prior art to the present invention.

Purines, acting via cell surface purinoceptors, have been implicated as having a variety of physiological and pathological roles, ATP, and to a lesser extent, adenosine, can stimulate sensory nerve endings resulting in intense pain and irritation and a pronounced increase in sensory nerve discharge. ATP receptors have been classified into two major families, the P2Y- and P2X-purinoreceptors, on the basis of molecular structure, transduction mechanisms, and pharmacological characterization. The P2Y-purinoceptors are Q-protein coupled receptors, while the P2X-purinoceptors are a family of ATP-gated cation channels. Purinergic receptors, in particular, P2X receptors, are known to form homomultimers or heteromultimers. To date, cDNAs for seven P2X subunits have been cloned, (P2X1, P2X2, P2X3, P2X4, P2X5, P2X6 and P2X7), each able to produce homotrimeric channels and some able to form heterotrimeric receptors (e.g. P2X2/3, P2X4/6 and P2X1/5). The structure and chromosomal mapping of mouse and human genomic P2X3 receptor subunits have also been described. In vitro, co-expression of P2X2 and P2X3 receptor subunits is necessary to produce ATP-gated currents with the properties seen in some sensory neurons.

P2X3 receptor subunits are found on primary sensory afferents innervating rodent and human organs and tissues. Data exist suggesting that ATP may be released from epithelial/endothelial cells of the hollow organs or from muscle beds as a result of distention, movement, injury infection and inflammation ATP released in this manner may serve a role in conveying information to nearby sensory neurons located. P2X receptors have been studied in a number of neurons, including sensory, sympathetic, parasympathetic, mesenteric, and central neurons. Some studies indicate that P2X purinergic receptors play a role in afferent neurotransmission from the many organ systems and tissues, and that modulators of P2X receptors are potentially useful in the treatment of functional organ or tissue disorders and attenuate common chronic symptoms and signs of important diseases or conditions.

Evidence also suggests a role of endogenous ATP and purinergic receptors in nociceptive responses in mice. ATP-induced activation of P2X3 receptors on dorsal root ganglion nerve terminals in the dorsal horn of the spinal cord has been shown to stimulate release of glutamate, a key neurotransmitter involved in nociceptive signalling. P2X3 receptors have been identified on nociceptive neurons in the tooth pulp. ATP released from distressed or damaged cells in many tissue systems may thus lead to pain by activating P2X3 containing receptors on nociceptive sensory nerve endings. This is consistent with observations of the induction of pain and discomfort by intradermally applied ATP in the human blister-base model or following its infusion into a muscle bed. P2X antagonists have been shown to be analgesic in many animal models. This evidence suggests that P2X3 containing channels are involved in the sensitization of nerves that drives and maintains heightened nociception signalling, and that modulators of P2X receptors are potentially useful as inhibitors of sensitization and may have applicability as analgesics, anti-pruritics, antitussives and treatments for autonomic hyperresponsiveness.

The use of antagonists of P2X2 and P2X2/3 for the treatment of pain was discussed by Carter, et al., (*Bioorganic and Medical Chemistry Letters*, 2009, 19(6), 1628-1635; doi: 10.1016/j.bmcl.2009.02.003). The structure-activity relationship of a series of diaminopyrimidines was studied. The selectivity of these compounds for P2X3 and P2X2/3 vs. other P2X purinoceptors was also discussed.

Vandenbeuch et al. (*J. Physiol*, 2015, 593(5), 1113-1125; doi: 10/1113/jphysiol.2014.281014) discuss the role of both P2X3 and P2X2/3 channels in taste transduction.

SUMMARY

In a first aspect of the present disclosure, there are provided compounds of Formula 1:

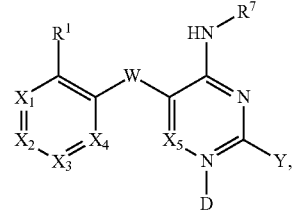

Formula 1 or a pharmaceutically acceptable salt thereof, wherein:
W is $CH_2$, NR (where R is H, or $C_{1-3}$ alkyl), O or S;
$X_1$ is N or $CR^2$;
$X_2$ is N or $CR^3$;
$X_3$ is N or $CR^4$;
$X_4$ is N or $CR^5$, provided, however not more than two of $X_1$, $X_2$, $X_3$, or $X_4$ are N at the same time;
$X_5$ is N or $CR^6$, provided, however, when $X_1$ is $CR^2$, $X_2$ is $CR^3$, $X_3$ is $CR^4$ and $X_4$ is $CR^5$, W is not O or —$CH_2$—;
Y is selected from hydrogen or —$NHR^d$, wherein $R^d$ is selected from hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalkyl; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{1-12}$-hydroxycarbonylalkyl; $C_{2-12}$-hydroxylalkyloxycarbonylalkyl; $C_{5-12}$-aryl; $C_{6-12}$-arylalkyl; $C_{5-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; or $C_{4-12}$-heterocyclylalkyl;

D is an optional oxygen;

$R^1$ is selected from $C_{1-12}$-alkyl; $C_{2-12}$-alkenyl; $C_{2-12}$-alkynyl; $C_{3-12}$-cycloalkyl; $C_{3-12}$-cycloalkenyl; halo; $C_{1-12}$-haloalkyl; or $C_{1-12}$-hydroxyalkyl;

$R^2$, $R^3$, $R^4$ and $R^5$ are each independently selected from hydrogen; $C_{1-12}$-alkyl; $C_{2-12}$-alkenyl; $C_{2-12}$-alkynyl; amino; halo; amido; $C_{1-12}$-haloalkyl; $C_{1-12}$-alkoxy; hydroxy; $C_{1-12}$-haloalkoxy; nitro; $C_{1-12}$-hydroxyalkyl; $C_{2-12}$-alkoxyalkyl; $C_{1-12}$-hydroxyalkoxy; $C_{3-12}$-alkynylalkoxy; $C_{1-12}$-alkylsulfonyl; $C_{5-12}$-arylsulfonyl; cyano; $C_{6-12}$-aryl; $C_{5-12}$-heteroaryl; $C_{3-12}$-heterocyclyl; $C_{4-12}$-heterocyclylalkoxy; $C_{6-12}$-aryloxy; $C_{5-12}$-heteroaryloxy; $C_{7-12}$-arylalkyloxy; $C_{6-12}$-heteroaralkyloxy; optionally substituted phenoxy; —$(CH_2)_m$—$(Z)_n$—$(CO)$—$R^f$ or —$(CH_2)_m$—$(Z)_n$—$SO_2$—$(NR^g)_{n'}$—$R^f$, where m, n and n' are each independently 0 or 1, Z is O or $NR^g$, $R^f$ is selected from hydrogen, $C_{1-12}$-alkyl, hydroxy, $C_{1-12}$-alkoxy, amino, $C_{1-12}$-hydroxyalkyl or $C_{2-12}$-alkoxyalkyl and each $R^g$ is independently hydrogen or $C_{1-12}$-alkyl;

$R^3$ and $R^4$ together with the atoms to which they are attached may form a five or six-membered ring that optionally includes one or two heteroatoms selected from O, S and N $R^2$ and $R^3$ may together form an alkylene dioxy; or $R^2$ and $R^3$ together with the atoms to which they are attached may form a five or six-membered ring that optionally includes one or two heteroatoms selected from O, S and N;

$R^6$ is selected from hydrogen; $C_{1-12}$-alkyl; and $R^7$ is selected from hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{3-12}$-hydroxyalkyloxycarbonylalkyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; or $C_{6-12}$-heterocyclylalkyl.

In certain aspects of the present disclosure, compounds of Formula 1 have >test fold (10×) selectivity for the P2X3 homotrimeric receptor compared to the P2X2/3 heterotrimeric receptor. In another aspect, compounds of Formula 1 have >20× selectivity for P2X3 receptor compared to P2X2/3 receptor. In another aspect, compounds of Formula 1 have >30× selectivity for P2X3 receptor compared to P2X2/3 receptor. In another aspect, compounds of Formula 1 have >40× selectivity for P2X3 receptor compared to P2X2/3 receptor. In another aspect, compounds of Formula 1 have >50× selectivity for P2X3 receptor compared to P2X2/3 receptor. In another aspect, compounds of Formula 1 have >1, but less than 10× selectivity for P2X3 receptor compared to P2X2/3 receptor.

In a second aspect, the present disclosure provides methods for treating a disease mediated by a P2X3 receptor antagonist, a P2X2/3 receptor antagonist, or both, said method comprising administering to a subject in need thereof an effective amount of a compound of Formula 1:

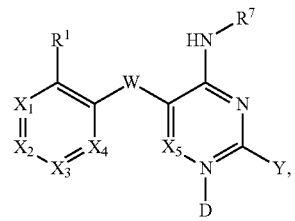

Formula 1 or a pharmaceutically acceptable salt thereof, wherein:

W is $CH_2$, NR (where R is H, or $C_{1-3}$ alkyl), O or S;

$X_1$ is N or $CR^2$;

$X_2$ is N or $CR^3$;

$X_3$ is N or $CR^4$;

$X_4$ is N or $CR^5$, provided, however not more than two of $X_1$, $X_2$, $X_3$, or $X_4$ are N at the same time;

$X_5$ is N or $CR^6$, provided, however, when $X_1$ is C—$R^2$, $X_2$ is C—$R^3$, $X_3$ is C—$R^4$ and $X_4$ is C—$R^5$, W is not O or —$CH_2$—;

Y is selected from hydrogen or —$NHR^d$, wherein $R^d$ is selected from; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalkyl; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{1-12}$-hydroxycarbonylalkyl; $C_{2-12}$-hydroxyalkyloxycarbonylalkyl; $C_{5-12}$-aryl; $C_{6-12}$-arylalkyl; $C_{5-12}$-arylsulfonyl; $C_{5-12}$-heteroaryl; $C_{6-12}$-heteroalkyl; $C_{5-12}$-heteroarylsulfonyl; $C_{3-12}$-heterocyclyl; and $C_{4-12}$-heterocyclylalkyl;

D is an optional oxygen;

$R^1$ is selected from $C_{1-12}$-alkyl; $C_{2-12}$-alkenyl; $C_{2-12}$-alkynyl; $C_{3-12}$-cycloalkyl; $C_{3-12}$-cycloalkenyl; halo; $C_{1-12}$-haloalkyl; or $C_{1-12}$-hydroxyalkyl;

$R^2$, $R^3$, $R^4$ and $R^5$ are each independently selected from hydrogen; $C_{1-12}$-alkyl; $C_{2-12}$-alkenyl; $C_{2-12}$-alkynyl; amino; halo; amido; $C_{1-12}$-haloalkyl; $C_{1-12}$-alkoxy; hydroxy; $C_{1-12}$-haloalkoxy; nitro; $C_{1-12}$-hydroxyalkyl; $C_{2-12}$-alkoxyalkyl; $C_{1-12}$-hydroxyalkoxy; $C_{3-12}$-alkynylalkoxy; $C_{1-12}$-alkylsulfonyl; $C_{5-12}$-arylsulfonyl; cyano; $C_{6-12}$-aryl; $C_{5-12}$-heteroaryl; $C_{3-12}$-heterocyclyl; $C_{4-12}$-heterocyclylalkoxy; $C_{6-12}$-aryloxy; $C_{5-12}$-heteroaryloxy; $C_{7-12}$-arylalkyloxy; $C_{6-12}$-heteroaralkyloxy; optionally substituted phenoxy; —$(CH_2)_m$—$(Z)_n$—$(CO)$—$R^f$ and —$(CH_2)_m$—$(Z)_n$—$SO_2$—$(NR^g)_{n'}$—$R^f$, where m, n and n' are each independently 0 or 1, Z is O or $NR^g$, $R^f$ is selected from $C_{1-12}$-alkyl, hydroxy, $C_{1-12}$-alkoxy, amino, $C_{1-12}$-hydroxyalkyl and $C_{2-12}$-alkoxyalkyl and each $R^g$ is independently hydrogen or $C_{1-12}$-alkyl;

$R^3$ and $R^4$ together with the atoms to which they are attached may form a five or six-membered ring that optionally includes one or two heteroatoms selected from O, S and N;

$R^2$ and $R^3$ may together form an alkylene dioxy; or $R^2$ and $R^3$ together with the atoms to which they are attached may form a five or six-membered ring that optionally includes one or two heteroatoms selected from O, S and N;

$R^6$ is selected from hydrogen; $C_{1-12}$-alkyl; and $R^7$ is selected from hydrogen; $C_{1-12}$-alkyl; $C_{3-12}$-cycloalkyl; $C_{4-12}$-cycloalkylalkyl, $C_{1-12}$-haloalkyl; $C_{1-12}$-hydroxyalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{3-12}$-hydroxyalkyloxycarbonylalkyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

Exemplary diseases and condition that are rationally treated by a P2X3 receptor antagonist, or a P2X2/3 receptor antagonist, or antagonist at both channels, contemplated herein include disorders of the urinary tract (aka uropathy), disease states associated with the urinary tract (aka urinary tract disease states), overactive bladder (aka detrusor hyperactivity or urge incontinence), outlet obstruction (aka benign prostatic hypertrophy), outlet insufficiency, pelvic hypersensitivity, bladder pain syndrome, endometriosis, respiratory symptoms, cough or urge to cough associated with a respiratory disease, asthma, hypertension, heart failure, dyspnea (aka shortness of breath), sleep apnea, signs and symptoms of carotid body hypertonicity and hyperraflexia (such as breathlessness and fatigue), sympathetic overactivity in a subject, and the like. Additionally, signs and symptoms of upper respiratory tract infection, including the cold and flu symptoms of pharyngitis, rhinitis, nasal congestion, hypertussivity, rhinorrhea and sneezing targeted conditions for treatment with an antagonist for P2X3 containing receptors.

In other instances the disease may be a disease associated with pain. The disease associated with pain may be; inflammatory pain; surgical pain; visceral pain; dental pain; premenstrual pain; central pain; pain due to burns; migraine or cluster headaches; nerve injury; neuropathy; neuritis; neuralgias; poisoning; ischemic injury; interstitial cystitis; cancer pain; pain of viral, parasitic or bacterial infection; post-traumatic injury pain; or pain associated with irritable bowel syndrome and inflammatory bowel diseases.

In additional instances the disorders or disease states may include hepatocellular carcinoma, tinnitus, migraine, itch (pruritus), diabetes mellitus, endometriosis and dysmenorrhea, peripheral artery occlusive disease (PAOD), intermittent claudication, acute and chronic heart failure, metabolic syndrome, chronic obstructive pulmonary disease (COPD), atopic dermatitis and other forms of eczema or dermatitis, prurigo nodularis, bursitis, tendonitis, fibromyalgia, gout, joint replacement, lichen sclerosus, psoriasis and psoriatic arthritis, cold sores, kidney stories, gall stones, smell disorders, taste disorders including dysgeusia or burning mouth syndrome, binge eating disorders, hyperphagia, obesity, gastro esophageal reflux disease (GERD), or pain from sickle cell anemia and ischemia.

The present disclosure also provides pharmaceutical compositions comprising the compounds, methods of using the compounds, and methods of preparing the compounds.

Definition of Terms

Unless otherwise stated, the following terms used in this Application, including the specification and claims, have the definitions given herein.

It must be noted that, as used in the specification and the appended claims, the singular forms "a", "an", and "the" include plural referents unless the context clearly dictates otherwise.

"Agonist" refers to a compound that enhances the activity of another compound or receptor site.

"Antagonist" refers to a compound that diminishes or prevents the action of another compound or receptor site. Antagonist selectivity for P2X3 subunit containing trimeric channel types, for example, is of increasing interest in the search for therapeutically preferred medicines. This is due to increased understanding, driven by clinical experience with first generation antagonists, of the potential contribution of blockade of distinct trimers with desirable (e.g., efficacy as antitussive, antihypertensive and antihyperalgesic) and less desirable (e.g., tolerability events such as hypogeusia, oropharyngeal dysesthesia) outcomes in treated patients.

Improved clinical effectiveness (efficacy vs. tolerability profile) is expected based on findings suggesting that channels formed solely from P2X3 subunits (homomeric P2X3 or P2X3.3.3) are found in nociceptive sensory fibers responsible for mediating irritative, painful and bothersome ("targeted") pathological symptoms such as cough, emanating mostly from neural crest derived sensory neurons of DRG and certain cranial (trigeminal, jugular) ganglia. In contrast, P2X channels involved in ATP mediation of the sense of taste, innervating the gustatory papillae of the tongue and oropharynx, are formed in placodally derived sensory neurons, notably from geniculate, petrosal and nodose cranial ganglia, as the heterotrimeric P2X2/3 (i.e., P2X2.3.3 and P2X2.2.3) channels found to be expressed in these cells.

Accordingly, antagonists with increased potency ($pIC_{50}$) at P2X3 homotrimers relative to P2X2/3 heterotrimers achieve greater attenuation of nociceptor sensitization and symptoms of pain, urgency, irritation, dyspnea, fatigue and autonomic hypeneflexia, before exposures are reached that introduce gustatory disturbance and raise issues of tolerability and patient compliance.

"Alkyl" means the monovalent linear or branched saturated hydrocarbon moiety, consisting solely of carbon and hydrogen atoms, having from one to twelve carbon atoms.

"Lower alkyl" refers to an alkyl group of one to six carbon atoms, i.e. $C_3$ alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear or branched saturated divalent hydrocarbon radical of one to twelve carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenyl" means a linear monovalent hydrocarbon radical of two to twelve carbon atoms or a branched monovalent hydrocarbon radical of three to twelve carbon atoms, containing at least one double bond. Examples of alkenyl groups include, but are not limited to, ethenyl (vinyl, $-CH=CH_2$), 1-propenyl ($-CH=CH-CH_3$), 2-propenyl (allyl, $-CH-CH=CH_2$) and isopropenyl (1-methylvinyl, $-C(CH_3)=CH_2$).

"Alkynyl" means a linear monovalent hydrocarbon radical of two to twelve carbon atoms or a branched monovalent hydrocarbon radical of three to twelve carbon atoms, containing at least one triple bond. Examples of alkynyl groups include, but are not limited to, ethynyl ($-C\equiv CH$) and 2-propynyl (propargyl, $-CH_2C\equiv CH$).

"Alkoxy" means a moiety of the formula $-OR$, wherein R is an alkyl moiety as defined herein. Examples of alkoxy moieties include, but are not limited to, methoxy, ethoxy, iso-propoxy, and the like.

"Alkoxyalkyl" meats a moiety of the formula $R^a-O-R^b-$, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxy-propyl, and 1-(2-methoxyethyl)-3-methoxypropyl.

"Alkoxyalkoxyalkl" means a group of the formula $-R-O-R'-O-R''$ wherein R and R' each are alkylene and R'' is alkyl as defined herein.

"Alkylcarbonyloxyalkyl" means a group of the formula —R—O—C(O)—R' wherein R is alkylene and R' is alkyl as defined herein.

"Alkylcarbonyl" means a moiety of the formula —R'—R", where R' is C(=O)— and R" is alkyl as defined herein.

"Alkylsulfonyl" means a moiety of the formula —R'—R", where R' is —SO$_2$— and R" is alkyl as defined herein.

"Alkylsulfonylalkyl" means a moiety of the formula —R'—R"—R'" where R' is alkyl, R" is —SO$_2$— and R'" is alkyl as defined herein.

"Alkylamino" means a moiety of the formula —NR—R' wherein R is hydrogen or alkyl and R' is alkyl as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Alkali metal ion" means a monovalent ion of a group I metal such as lithium, sodium, potassium, rubidium or cesium, preferably sodium or potassium.

"Alkaline earth metal ion" means a divalent ion of a group II metal such as berylium, magnesium, calcium, strontium or barium, preferably magnesium or calcium.

"Amino" means a group —NR'R" wherein R' and R" each independently is hydrogen or alkyl. "Amino" as used herein thus encompasses "alkylamino" and "dialkylamino".

"Alkylaminoalkyl" means a group —R—NHR' wherein R is alkylene and R' is alkyl. Alkylaminoalkyl includes methylaminomethyl, methylaminoethyl, methylaminopropyl, ethylaminoethyl and the like.

"Dialkylaminoalkyl" means a group —R—NR'R" wherein R is alkylene and R' and R" are alkyl as defined herein. Dialkylaminoalkyl includes dimethylaminomethyl, dimethylaminoethyl, dimethylaminopropyl, N-methyl-N-ethylaminoethyl, and the like.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like.

"Aminoalkoxy" means a group —OR—R$^1$ wherein R' is amino and R is alkylene as defined herein.

"Alkylsulfonylamido" means a moiety of the formula —NR'SO$_2$—R wherein R is alkyl and R' is hydrogen or alkyl.

"Aminocarbonyloxyalkyl" or "carbamylalkyl" means a groups —R—O—C(=O)—R' wherein R' is amino and R is alkylene as defined herein.

"Aminosulfonyl" means a group —SO$_2$—NR'R" wherein R' and R" each independently is hydrogen or alkyl. "Aminosulfonyl" as used herein thus encompasses "alkylaminosulfonyl" and "dialkylaminosulfonyl".

"Alkynylalkoxy" means a group of the formula —O—R—R' wherein R is alkylene and R' is alkynyl as defined herein.

"Aryl" means a monovalent cyclic aromatic hydrocarbon moiety comprising of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzominonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylalkyl" and "Aralkyl", which may be used interchangeably, mean a radical—R$^a$R$^b$ where R$^a$ is an alkylene group and R$^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —SO$_2$—R wherein R is aryl as defined herein.

"Aryloxy" means a group of the formula —O—R wherein R is aryl as defined herein.

"Aralkyloxy" or "Arylalkyloxy" means a group of the formula —O—R—R" wherein R is alkylene and R' is aryl as defined herein.

"Cyanoalkyl"" means a moiety of the formula —R'—R", where R' is alkylene as defined here-in and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkenyl" means a monovalent unsaturated carbocyclic moiety consisting of mono- or bicyclic rings containing at least one double bond. Cycloalkenyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkenyl moieties include, but are not limited to, cyclopropenyl, cyclobutenyl, cyclopentenyl, cyclohexenyl, cycloheptenyl.

"Cycloalkylalkyl" means a moiety of the formula —R'—R", where R' is alkylene and R" is cycloalkyl as defined herein.

"Cycloalkylene" means a divalent saturated carbocyclic radical consisting of mono- or bi-cyclic rings. Cycloalkylene can optionally be substituted with one or more substituents, wherein each substituent is independently hydroxy, alkyl, alkoxy, halo, haloalkyl, amino, monoalkylamino, or dialkylamino, unless otherwise specifically indicated.

"Cycloalkylalkylene" means a moiety of the formula —R'—R"—, where R' is alkylene and R" is cycloalkylene as defined herein.

"Heteroalkyl" means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, aryl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonyl propyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaiyl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

Heteroarylalkyl" or "heteroaralkyl" means a group of the formula —R—R' wherein R is alkylene and R' is heteroaryl as defined herein.

"Heteroarylsulfonyl" means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R'' wherein R is alkylene and R' is heteroaryl as defined herein.

"Heterocyclylalkoxy means a group of the formula —O—R—R' wherein R is alkylene and R' is heterocyclyl as defined herein.

The terms "halo", "halogen" and "halide", which may be used interchangeably, refer to a substituent fluoro, chloro, bromo, or iodo. In some embodiments, halo refers to a fluoro substituent.

"Haloalkyl" means alkyl as defined herein in which one or more hydrogen has been replaced with same or different halogen. In some embodiments, haloalkyl is a fluoroalkyl; in some embodiments, the haloalkyl is a perfluoroalkyl. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. In some embodiments, haloalkoxy is a fluoroalkoxy; in some embodiments, the haloalkoxyl is a perfluoroalkoxy. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydroisoquinolinyl, and the like.

"Heterocyclylalkyl" means a moiety of the formula —R—R' wherein R Is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R'' wherein R is alkylene, R' is hydrogen or alkyl, and R'' is hydroxyalkyl as defined herein.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxy-propyl, 2-hydroxy-1-hydroxymethylethyl, 2,3-dihydroxybutyl, 3,4-dihydroxybutyl and 2-(hydroxymethyl)-3-hydroxypropyl.

"Hydroxycarbonylalkyl" or "carboxyalkyl" means a group of the formula —R—(CO)—OH where R is alkylene as defined herein.

"Hydroxyalkyloxycarbonylalkyl" or "hnydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxyl-5-methyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl.

"Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxy-cyclohexyl, and the like.

"Urea" or "ureido" means a group of the formula —NR'—C(O)—NR''R''' wherein R, R'' and R''' each independently is hydrogen or alkyl.

"Carbamate" means a group of the formula —O—C(O)—NR'R'' wherein R' and R'' each independently is hydrogen or alkyl.

"Carboxy" means a group of the formula —C(O)OH.

"Sulfonamido" means a group of the formula —SO$_2$—NR'R'' wherein R', R'' and R'' each independently is hydrogen or alkyl.

"Nitro" means —NO$_2$.

"Cyano" mean —CN.

"Phenoxy" means a phenyl ring that is substituted with at least one —OH group.

"Acetyl" means —C(=O)—CH$_3$.

"C$_{n-m}$-" is used as a prefix before a functional group wherein 'n' and 'm' are recited as integer values (i.e. 0, 1, 2, 12), for example $C_{1-12}$-alkyl or $C_{5-12}$-heteroaryl. The prefix denotes the number, or range of numbers, of carbons atoms present in the functional group. In the case of ring systems the prefix denotes the number of ring atoms, or range of the number of ring atoms, whether the ring atoms are carbon atoms or heteroatoms. In the case of functional groups made up a ring portion and a non-ring portion (i.e. "arylalkyl" is made up of an aryl portion and an alkyl portion) the prefix is used to denote how many carbon atoms and ring atoms are present in total. For example, with arylalkyl, "$C_7$-arylalkyl" may be used to denote "phenyl-$CH_2$—". In the case of some functional groups zero carbon atoms may be present, for example $C_6$-aminosulfonyl (i.e. —$SO_2$—$NH_2$, with both potential R groups as hydrogen) the '0' indicates that no carbon atoms are present.

"Peptide" means an amide derived from two or more amino acids by combination of the amino group of one acid with foe carboxyl group. "Monopeptide" means a single amino acid, "dipeptide" means an amide compound comprising two amino acids, "tripeptide" means an amide compound comprising three amino acids, and so on. The C-terminus of a "peptide" may be joined to another moiety via an ester functionality.

"Optionally substituted", when used in association with "aryl", phenyl", "heteroaryl" "cyclo-hexyl" or "heterocyclyl", means an aryl, phenyl, heteroaryl, cyclohexyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, monoalkylamino, dialkylamino, haloalkyl, haloalkoxy, heteroalkyl, —COR (where R is hydrogen, alkyl, phenyl or phenylalkyl), —(CR'R")—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy dihalophosphinoyloxy optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including, e.g., benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present disclosure are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include: acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalene-sulfonic acid, propionic acid, salicylic acid, succinic acid, tartaric acid, p-toluenesulfonic acid, trimethylaceric acid, and the like; or salts formed when an acidic proton present in the parent compound either is replaced by a metal ion, e.g., an alkali metal ion, an alkaline earth ion, or an aluminum ion, or coordi-nates with an organic or inorganic base. Acceptable organic bases include diethanolamine, ethanolamine N-methylglucamine, triethanolamine, trimethylamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, "Design of prodrugs" p 1-92, Elsevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of the present disclosure rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The person skilled in the art will know how to choose a group for the ease of removal and for the ability to withstand the following reactions.

"Solvates" means solvent additions forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such com-bination being able to form one or more hydrate.

"Subject" means mammals and non-mammals. Mammals means any member of the mammalia class including, but not limited to, humans; non-human primates such as chimpanzees and other apes and monkey species; farm animals such as cows, horses, sheep, goats, and swine; domestic animals such as rabbits, dogs, and cats; laboratory animals in-eluding rodents, such as rats, mice, and guinea pigs; and the like. Examples of non-mammals include, but are not limited to, birds, and the like. The term "subject" does not denote a particular age or sex.

"Disorders of the urinary tract" or "uropathy" used interchangeably with "symptoms of the urinary tract" means the pathologic changes in the urinary tract. Examples of urinary tract disorders include, but are not limited to, incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, low micturition threshold, unstable bladder contractions, sphincteric spasticity, detrusor hyperreflexia (neurogenic bladder; dyssynergia), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodyma, prostatitis, vulvadynia, urethritis, orchidalgia, overactive bladder, and the like.

"Cough" includes acute, sub-acute and chronic cough, treatment-resistant cough, idiopathic chronic cough, post-viral cough, introgenic cough, cough associated with post-nasal drip, cough associated with upper respiratory infection, asthma and/or COPD, cough associated with interstitial disease, cough associated with gastroesophageal reflux disease (GERD), cough associated with smoking or a form of bronchitis, neuronal hypeersensitivity underlying acute, sub-acute or chronic cough, and the like.

The term "hypertension" as used herein refers to a condition or disease well known in the art in which the blood pressure in a mammal is chronically elevated. In certain embodiments hypertension may refer to a condition in which a subject's resting systolic blood pressure is above about 120 mmHg and/or diastolic pressure is above about 80 mmHg. In certain embodiments hypertension may refer to a condition in which a subject's resting systolic blood pressure is above about 115 mmHg; or above about 120 mmHg; or above about 125 mmHg; or above about 130 mmHg; or above about 135 mmHg; or above about 140 mmHg; or above about 145 mmHg; or above about 150 mmHg; or above about 155; or above about 160; or above about 165; or above about 170 and/or resting diastolic pressure is above about 75 mmHg; or above about 80 mmHg; or above about 85 mmHg; or above about 90 mmHg; or above about 95 mmHg; or above about 100 mmHg, or above about 105 mmHg; or above about 110 mmHg. In some embodiments hypertension may be primary or secondary hypertension. In some embodiments hypertension may be chronic treatment resistant hypertension, defined as persistent hypertension (resting office blood pressure>140/90 [SBP/DBP]) despite use of 2 or 3 antihypertensive medications including a diuretic, as well as hypertension in patients unable to tolerate currently preferred antihypertensive medications, or in whom approved medications cannot achieve recommended levels of BP control. Diagnosis of hypertension in a subject may in various embodiments be performed by an individual to make such diagnosis in a particular jurisdiction qualified.

The term "heart failure" as used herein refers to a condition or disease well known in the art which is associated with the heart being unable to maintain blood flow sufficient to maintain the needs of the body. Diagnosis of heart failure may in certain embodiments be based on echocardiography results characteristic of heart failure. In some embodiments, heart failure may refer to a condition often referred to as congestive heart failure. In some embodiments, heart failure may refer to systolic heart failure, also called heart failure due to reduced ejection fraction (HFREF) or heart failure due to left ventricular systolic dysfunction. In some embodiments, heart failure may refer to heart failure with preserved ejection fraction (HFPEF) also known as diastolic heart failure or heart failure with normal ejection fraction (HF-NEF). In some embodiments, heart failure may be chronic heart failure and in other embodiments the heart failure may be acute heart failure. Diagnosis of heart failure in a subject may in various embodiments be performed by an individual qualified to make such diagnosis in a particular jurisdiction.

The term "dyspnea" as used herein refers to a condition or disease well known in the art in which a subject experiences feelings or sensations associated with impaired breathing. In some embodiments dyspnea may refer to a condition consistent with the America Thoracic Society definition of dyspnea, i.e., "a subjective experience of breathing discomfort that consists of qualitatively distinct sensations that vary in intensity". In some embodiments dyspnea may refer to sensations of inadequate breathing, uncomfortable awareness of breathing and/or breathlessness. Diagnosis of dyspnea in a subject may in various embodiments be performed by an individual qualified to make such diagnosis in a particular jurisdiction.

The term "sleep apnea" as used herein refers to a condition or disease well known in the art characterized by disruptions in breathing (e.g., pauses in breathing or instances of shallow or infrequent breathing, accompanied by ischemia/hypoxemia) during sleep. In some aspects sleep apnea is central sleep apnea, obstructive sleep apnea, or mixed sleep apnea. In some embodiments, sleep apnea may be characterized by more than about 5 apneic events per hour of sleep; or more than about 10 apneic events per hour of sleep, or more than about 15 apneic events per hour sleep, or more than about 20 apneic events per hour of sleep, or more than about 25 apneic events per hour of sleep, or more than about 30 apneic sleep events per hour sleep; or more than about 35 apneic sleep events per hour sleep. Diagnosis of dyspnea in a subject may in various embodiments be performed by an individual qualified to make such diagnosis in a particular jurisdiction.

The term "carotid body" as used herein refers to a small cluster of chemoreceptors and supporting cells located near the fork (bifurcation) of the carotid artery. The carotid body is also referred in the art as carotid glomus or glomus caroticum. The term "altering carotid body tonicity" or activity as used herein means modifying the level of excitation of carotid sinus nerve chemoreceptor afferents that are discharging excessively in response to dysregulated levels of arterial chemicals (hyperreflexia), as well as attenuating the aberrant, spontaneous discharge of such nerve fibers that can occur in the absence of chemical dysregulation (hypertonoicity).

"Therapeutically effective amount" means an amount of a compound that, when administered to a subject for treating a disease state, is sufficient to effect such treatment for the disease stale. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, ie., arresting the development of the disease state or its clinical symptoms, or
(iii) relieving the disease state, ie., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Any open valency appearing on a carbon, oxygen, sulfur or nitrogen atom in the structures herein indicates the presence of a hydrogen atom.

All patents and publications identified herein are incorporated herein by reference in their entirety.

In certain embodiments, $X_1$ in Formula 1 is C—$R^2$ and W is S, providing compounds of Formula 1a as follows:

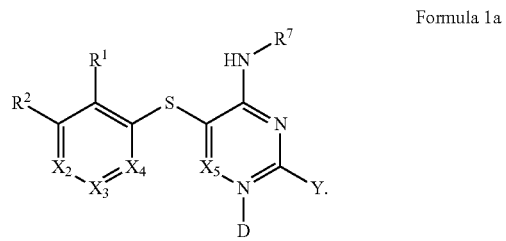

Formula 1a

In certain embodiments, $X_1$ in Formula 1 is N, providing compounds of the Formula 1b, as follows:

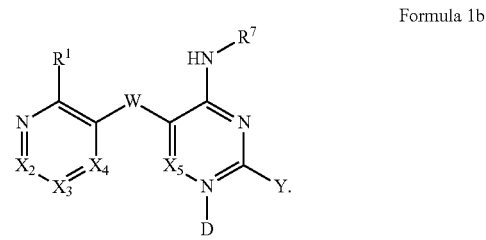

Formula 1b

In some embodiments of Formula 1b, W is O. In some embodiments of Formula 1b, W is S. In some embodiments of Formula 1b, W is $CH_2$. In some embodiments of Formula 1b, W is NR.

In certain embodiments, $X_1$ in Formula 1 is C—$R^2$ and $X_2$ is N, providing compounds of Formula 1c, as follows:

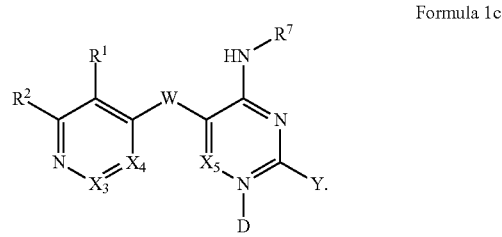

Formula 1c

In some embodiments of Formula 1c, W is O. In some embodiments of Formula 1c, W is S. In some embodiments of Formula 1c, W is $CH_2$. In some embodiments of Formula 1c, W is NR.

In certain embodiments, $X_1$ in Formula 1 is C—$R^2$ and $X_3$ is N, providing compounds of Formula 1d, as follows:

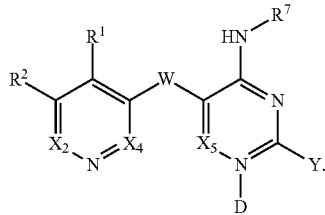

Formula 1d

In some embodiments of Formula 1d, W is O. In some embodiments of Formula 1d, W is S. In some embodiments of Formula 1d, W is $CH_2$. In some embodiments of Formula 1d, W is NR.

In certain embodiments, $X_1$ in Formula 1 is C—$R^2$ and $X_4$ is N, providing compounds of Formula 1e, as follows:

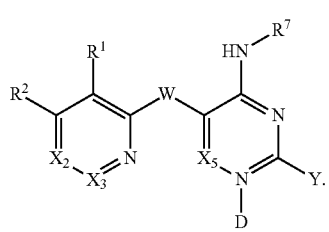

Formula 1e

In some embodiments of Formula 1e, W is O. In some embodiments of Formula 1e, W is S. In some embodiments of Formula 1e, W is $CH_2$. In some embodiments of Formula 1e, W is NR.

In certain embodiments, $X_1$ in Formula 1 is C—$R^2$ and both $X_2$ and $X_3$ are N, providing compounds of Formula 1f, as follows:

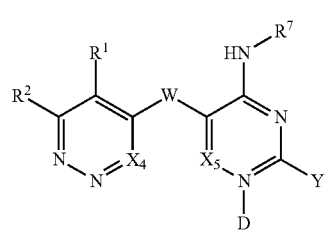

Formula 1f

In some embodiments of Formula 1f, W is O. In some embodiments of Formula 1f, W is S. In some embodiments of Formula 1f, W is $CH_2$. In some embodiments of Formula 1f, W is NR.

In certain embodiments, $X_1$ in Formula 1 is C—$R^2$ and both $X_2$ and $X_4$ are N, providing compounds of Formula 1g, as follows:

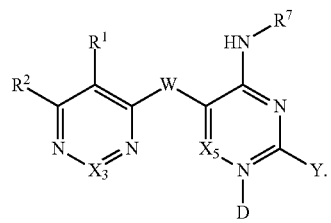

Formula 1g

In some embodiments of formula 1g, W is O. In some embodiment of Formula 1g, W is S. In some embodiments of Formula 1g, W is $CH_2$. In some embodiments of Formula 1g, W is NR.

In certain embodiment, $X_1$ in Formula 1 is C—$R^2$ and both $X_3$ and $X_4$ are N, providing compounds of Formula 1h, as follows:

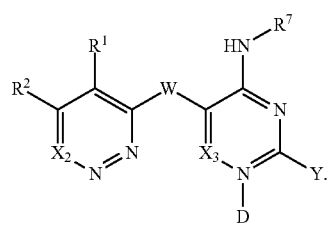

Formula 1h

In some embodiments of Formula 1h, W is O. In some embodiments of Formula 1h, W is S. In some embodiments of Formula 1h, W is $CH_2$. In some embodiments of Formula 1h, W is NR.

In certain embodiments, both $X_1$ and $X_2$ of Formula 1 are N, providing compounds of Formula 1i as follows:

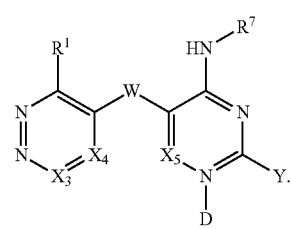

Formula 1i

In some embodiments of Formula 1i, W is O. In some embodiments of Formula 1i, W is S. In some embodiments of Formula 1i, W is $CH_2$. In some embodiments of Formula 1i, W is NR.

In certain embodiments, both $X_1$ and $X_3$ of Formula 1 are N, providing the compounds of Formula 1j, as follows:

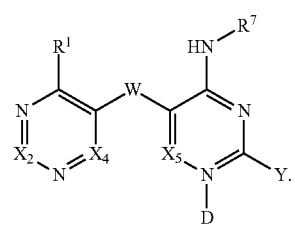

Formula 1j

In some embodiments of Formula 1j, W is O. In some embodiments of Formula 1j, W is S. In some embodiments of Formula 1j, W is CH$_2$. In some embodiments of Formula 1j, W is NR.

In certain embodiments, both X$_1$ and X$_4$ of Formula 1 are N, providing compounds of Formula 1k, as follows:

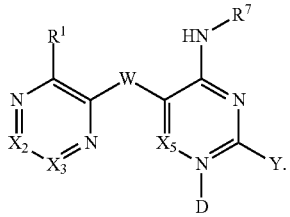

Formula 1k

In some embodiments of Formula 1k, W is O. In some embodiments of Formula 1k, W is S. In some embodiments of Formula 1k, W is CH$_2$. In some embodiments of Formula 1k, W is NR.

In certain embodiments, X$_5$ of Formula 1 is N, providing compounds of Formula 1l, as follows:

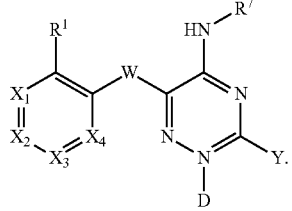

Formula 1l

In some embodiments of Formula 1l, W is O. In some embodiments of Formula 1l, W is S. In some embodiments of Formula 1l, W is CH$_2$. In some embodiments of Formula 1l, W is NR.

In certain embodiments, X$_5$ of Formula 1 is C—R$^6$, providing compounds of Formula 1m, as follows:

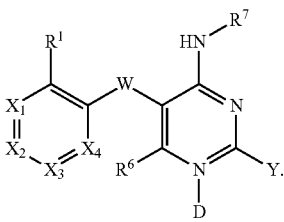

Formula 1m

In some embodiments of Formula 1m, W is O. In some embodiments of Formula 1m, W is S. In some embodiments of Formula 1m, W is CH$_2$. In some embodiments of Formula 1m, W is NR. In certain embodiments of Formula 1m, when X$_1$ is C—R$^2$, X$_2$ is C—R$^3$, X$_3$ is C—R$^4$ and X$_4$ is C—R$^5$, W is not O or —CH$_2$—.

In certain embodiments, X$_2$ and X$_3$ of Formula 1 are each C—OMe, providing compounds of Formula 1n, as follows:

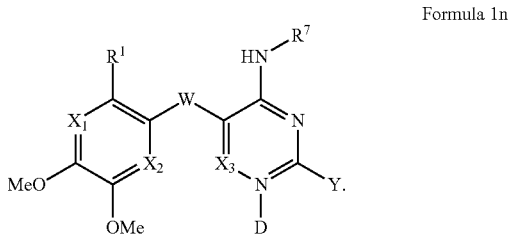

Formula 1n

In some embodiments of Formula 1n, W is O. In some embodiments of Formula 1n, W is S. In some embodiments of Formula 1n, W is CH$_2$. In some embodiments of Formula 1n, W is NR.

In certain embodiments of any one of Formulae 1-1n, R$^5$ and R$^6$ are hydrogen.

In certain embodiments of any one of Formulae 1-1n, R$^6$ is hydrogen or methyl.

In certain embodiments of any one of Formulae 1-1n, R$^2$ is hydrogen.

In certain embodiments of any one of Formulae 1-1n, D is absent.

In certain embodiments of any one of Formulae 1-1n, R$^1$ is selected from C$_{1-12}$-alkyl, C$_{2-12}$-alkenyl and C$_{3-12}$-cycloalkyl. In some of these embodiments, R$^1$ is selected from ethyl, cyclopropyl, isopropenyl and isopropyl. In particular embodiments, R$^1$ is isopropyl. In particular embodiments, R$^1$ is ethyl. In particular embodiments, R$^1$ is cyclopropyl.

In certain embodiments of any one of Formulae 1-1n, R$^7$ is selected from; C$_{1-12}$-alkyl, C$_{3-12}$-cycloalkyl; C$_{4-12}$-cycloalkylalkyl; C$_{1-12}$-haloalkyl; C$_{1-12}$-hydroxyalky; C$_{2-12}$-alkoxyalkyl; C$_{2-12}$-alkylsulfonylalkyl; acetyl; C$_{1-12}$-alkylsulfonyl; C$_{6-12}$-aryl; C$_{7-12}$-arylalkyl; C$_{6-12}$-arylsulfonyl; C$_{5-12}$-heteroaryl; C$_{6-12}$-heteroarylalkyl; C$_{5-12}$-heteroarylsulfonyl; C$_{3-12}$-heterocyclyl; and C$_{4-12}$-heterocyclyalkyl.

In certain embodiments of any one of Formulae 1-1n, R$^7$ is selected from C$_{1-12}$-alkyl, C$_{1-12}$-hydroxyalkyl and C$_{1-12}$-haloalkyl.

In certain embodiments of any one of Formulae 1-1n, Y is —NHR$^d$. In some of these embodiments of formula 1, R$^d$ is selected from: C$_{1-12}$-alkyl, C$_{3-12}$-cycloalkyl; C$_{4-12}$-cycloalkylalkyl; C$_{1-12}$-haloalkyl; C$_{1-12}$-hydroxyalky; C$_{2-12}$-alkoxyalkyl; C$_{2-12}$-alkylsulfonylalkyl; acetyl; C$_{1-12}$-alkylsulfonyl; C$_{6-12}$-aryl; C$_{7-12}$-arylalkyl; C$_{6-12}$-arylsulfonyl; C$_{5-12}$-heteroaryl; C$_{6-12}$-heteroarylalkyl; C$_{5-12}$-heteroarylsulfonyl; C$_{3-12}$-heterocyclyl; and C$_{4-12}$-heterocyclylalkyl. In particular embodiments, R$^d$ is selected from C$_{1-12}$-alkyl, C$_{1-12}$-hydroxyalkyl and C$_{1-12}$-haloalkyl.

In certain embodiments of any one of Formulae 1-1n, R$^3$ and R$^4$ each independently is C$_{1-12}$-alkyl, C$_{2-12}$-alkynyl, cyano, C$_{0-12}$-sulfonamido, —COOH, C$_{5-12}$-heteroaryl, halo, C$_{1-12}$-alkoxy, C$_{1-12}$-halo-alkoxy or C$_{1-12}$-alkylsulfonyl.

In certain embodiments of any one of Formulae 1-1n, R$^3$ is halo, C$_{1-12}$-alkoxy, C$_{1-12}$-haloalkoxy or hydroxy. In further embodiments, R$^3$ is methoxy, fluoro, or chloro. In particular embodiments, R$^3$ is methoxy. In certain embodiments R$^3$ is hydroxy.

In certain embodiments of any one of Formulae 1-1n, R$^4$ is C$_{1-12}$-alkyl, C$_{2-12}$-alkynyl, cyano, C$_{0-12}$-sulfonamido, —COOH, halo, C$_{1-12}$-alkoxy, C$_{1-12}$-alkylsulfonyl or C$_{5-12}$-heteroaryl. In further embodiments, R$^4$ is methoxy, iodo, methanesulfonyl or C$_{5-12}$-heteroaryl. In particular embodiments, R$^4$ is methoxy, methyl, cyano, bromo, chloro, iodo, —C≡C—CH$_3$, —C≡CH, —COOH, —S(O)$_2$CH$_3$, —S(O)$_2$NH$_2$ or tetrazolyl. In specific embodiments R$^4$ may be methoxy, while in other embodiments R$^4$ may be iodo.

In certain embodiments of any one of Formulae 1-1n, R$^7$, R$^d$ and R$^e$ are hydrogen.

In certain embodiments of any one of Formulae 1-1n, R$^3$ and R$^4$ together with the atoms to which they are attached may form a five or six-membered ring that optionally includes one or two heteroatoms selected from O, S and N. In many such embodiments R$^3$ and R$^4$ together with the atoms to which they are attached may form: a five membered aromatic with one nitrogen, i.e. a pyrrol ring; a five membered aromatic with two nitrogens, i.e., a pyrazol or imidazol ring; a five membered aromatic with one nitrogen and one oxygen, i.e., an ox-azole or isoxazole ring; a five membered aromatic with one nitrogen and one sulfur, i.e., a thiazole or isothiazole ring; a five membered aromatic with one oxygen, i.e., a furanyl ring; or a five membered aromatic with one sulfur, i.e., a thiophenyl ring.

In certain embodiments of any one of Formulae 1-1n, R$^2$ and R$^3$ together with the atoms to which they are attached may form a five or six-membered ring that optionally includes one or two heteroatoms selected from O, S and N. In many such embodiments R$^3$ and R$^4$ together with the atoms to which they are attached may form: a five membered aromatic with one nitrogen, i.e. a pyrrol ring; a five membered aromatic with two nitrogens, i.e. a pyrazol or imidazole ring; a five membered aromatic with one nitrogen and one oxygen, i.e., an oxazole or isoxazole ring; a five membered aromatic with one nitrogen and one sulfur, i.e., a thiazole or isothiazole ring; a five membered aromatic with one oxygen, i.e., a furanyl ring; or a five membered aromatic with one sulfur, i.e., a thiophenyl ring.

In some embodiments of the present disclosure, the compounds may be of Formula 2:

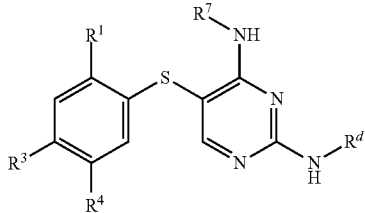

Formula 2 wherein:
R$^1$ is C$_{1-12}$-alkyl; C$_{2-12}$-alkenyl; C$_{3-12}$cycloalkyl; or C$_{3-12}$-cycloalkenyl; or halo;
R$^3$ and R$^4$ each independently is: hydrogen; C$_{1-12}$-alkyl; C$_{2-12}$-alkenyl; C$_{2-12}$-alkynyl; amino; halo; amido; C$_{1-12}$-haloalkyl; C$_{1-12}$-alkoxy, hydroxy; C$_{1-12}$-haloalkoxy; nitro; C$_{1-12}$-hydroxyalkyl; C$_{2-12}$-alkoxyalkyl; C$_{1-12}$-hydroxyalkoxy; C$_{3-12}$-alkynylalkoxy; C$_{2-12}$-alkylsulfonyl; C$_{6-12}$-arylsulfonyl; cyano; C$_{6-12}$-aryl; C$_{5-12}$-heteroaryl; C$_{3-12}$-heterocyclyl; C$_{4-12}$-heterocyclylalkoxy; C$_{6-12}$-aryloxy; C$_{5-12}$-heteroaryloxy; C$_{7-12}$-arylalkyloxy; C$_{6-12}$-heteroarylalkyloxy; optionally substituted phenoxy; —(CH$_2$)$_m$—(Z)$_n$—(CO)—R$^f$ or —(CH$_2$)$_m$—(Z)$_n$—SO$_2$—(NR$^g$)$_{n'}$—R$^f$, where m, n and n' are each independently 0 or 1,
Z is O or NR$^g$,
R$^f$ is hydrogen, C$_{1-12}$-alkyl, hydroxy, C$_{1-12}$-alkoxy, amino, C$_{1-12}$-hydroxyalkyl or C$_{2-12}$-alkoxyalkyl, and each R$^g$ is independently hydrogen or C$_{1-12}$-alkyl; or R$^3$ and R$^4$ together with the atoms to which they are attached may form a five or six-membered ring that optionally includes one or two heteroatoms selected from O, S and N;
R$^7$ is selected from hydrogen; C$_{1-12}$-alkyl; C$_{3-12}$-cycloalkyl; C$_{4-12}$-cycloalkylalkyl; C$_{1-12}$-haloalkyl; C$_{1-12}$-haloalkoxy; C$_{1-12}$-hydroxyalkyl; C$_{2-12}$-alkoxyalkyl; acetyl; C$_{1-12}$-alkylsulfonyl; C$_{2-12}$-alkylsulfonylalkyl; C$_{2-12}$-aminocarbonyloxyalkyl; C$_{2-12}$-hydroxycarbonylalkyl; C$_{2-12}$-hydroxyalkyloxycarbonylalkyl; C$_{6-12}$-aryl; C$_{7-12}$-arylalkyl; C$_{6-12}$-arylsulfonyl; C$_{5-12}$-heteroaryl; C$_{6-12}$-heteroarylalkyl; C$_{5-12}$-heteroarylsulfonyl; C$_{3-12}$-heterocyclyl; and C$_{4-12}$-heterocyclylalkyl; and
R$^d$ is selected from hydrogen; C$_{1-12}$-alkyl; C$_{3-12}$-cycloalkyl; C$_{4-12}$-cycloalkylalkyl; C$_{1-12}$-haloalkyl; C$_{1-12}$-haloalkoxy; C$_{1-12}$-hydroxyalky; C$_{2-12}$-alkoxyalkyl; acetyl; C$_{1-12}$-alkylsulfonyl; C$_{2-12}$-alkylsulfonylalkyl; C$_{2-12}$-aminocarbonyloxyalkyl; C$_{2-12}$-hydroxycarbonylalkyl; C$_{2-12}$-hydroxyalkyloxycarbonylalkyl; C$_{6-12}$-aryl; C$_{7-12}$-arylalkyl; C$_{6-12}$-arylsulfonyl; C$_{5-12}$-heteroaryl; C$_{6-12}$-heteroarylalkyl; C$_{5-12}$-heteroarylsulfonyl; C$_{3-12}$-heterocyclyl; and C$_{4-12}$-heterocyclylalkyl.

In certain embodiments of Formula 2, R$^1$ is selected from C$_{1-12}$-alkyl, C$_{2-12}$-alkenyl and C$_{3-12}$-cycloalkyl. In some of these embodiments, R$^1$ is selected from ethyl, cyclopropyl, isopropenyl and isopropyl. In particular embodiments, R$^1$ is isopropyl. In particular embodiments, R$^1$ is ethyl. In particular embodiments, R$^1$ is cyclopropyl.

In certain embodiments of Formula 2, R$^7$ is selected from: C$_{1-12}$-alkyl, C$_{3-12}$-cycloalkyl; C$_{4-12}$-cycloalkylalkyl; C$_{1-12}$-haloalkyl; C$_{1-12}$-hydroxyalky; C$_{2-12}$-alkoxyalkyl; C$_{2-12}$-alkylsulfonylalkyl; acetyl; C$_{1-12}$-alkylsulfonyl; C$_{6-12}$-aryl; C$_{7-12}$-arylalkyl; C$_{6-12}$-arylsulfonyl; C$_{5-12}$-heteroaryl; C$_{6-12}$-heteroarylalkyl; C$_{5-12}$-heteroarylsulfonyl; C$_{3-12}$-heterocyclyl; and C$_{4-12}$-heterocyclylalkyl.

In certain embodiments of Formula 2, R$^7$ is selected from C$_{1-12}$-alkyl, C$_{1-12}$-hydroxyalkyl and C$_{1-12}$-haloalkyl.

In certain embodiments of Formula 2, R$^d$ is selected from: C$_{1-12}$-alkyl, C$_{3-12}$-cycloalkyl; C$_{4-12}$-cycloalkylalkyl; C$_{1-12}$-haloalkyl; C$_{1-12}$-hydroxyalky; C$_{2-12}$-alkoxyalkyl; C$_{2-12}$-alkylsulfonylalkyl; acetyl; C$_{1-12}$-alkylsulfonyl; C$_{6-12}$-aryl; C$_{7-12}$-arylalkyl; C$_{6-12}$-arylsulfonyl; C$_{5-12}$-heteroaryl; C$_{6-12}$-heteroarylalkyl; C$_{5-12}$-heteroarylsulfonyl; C$_{3-12}$-heterocyclyl; and C$_{4-12}$-heterocyclylalkyl. In further embodiments, R$^d$ is selected from C$_{1-12}$-alkyl, C$_{1-12}$-hydroxyalkyl and C$_{1-12}$-haloalkyl.

In certain embodiments of Formula 1, R$^3$ and R$^4$ each independently is C$_{1-12}$-alkyl, C$_{2-12}$-alkynyl, cyano, C$_{0-12}$-sulfonamido, —COOH, C$_{5-12}$-heteroaryl, halo, C$_{1-12}$-alkoxy, C$_{1-12}$-halo-alkoxy or C$_{1-12}$-alkylsulfonyl.

In certain embodiments of Formula 1, R$^3$ is halo, C$_{1-12}$-alkoxy, C$_{1-12}$-haloalkoxy or hydroxy. In further embodiments, R$^3$ is methoxy, fluoro, or chloro. In particular embodiments, R$^3$ is methoxy. In certain embodiments R$^3$ is hydroxy.

In certain embodiments of Formula 1, R$^4$ is C$_{1-12}$-alkyl, C$_{2-12}$-alkynyl, cyano, C$_{0-12}$-sulfonamido, —COOH, halo, C$_{1-12}$-alkoxy, C$_{1-12}$-alkylsulfonyl or C$_{5-12}$-heteroaryl. In further embodiments, R$^4$ is methoxy, iodo, methanesulfonyl or C$_{5-12}$-heteroaryl. In particular embodiments, R$^4$ is methoxy, methyl, cyano, bromo, chloro, iodo, —C≡C—CH$_3$, —C≡CH, —COOH, —S(O)$_2$CH$_3$, —S(O)$_2$NH$_2$ or tetrazolyl. In specific embodiments R$^4$ may be methoxy, while in other embodiments R$^4$ may be iodo.

In certain embodiments of Formula 2, R$^7$, R$^d$ and R$^e$ are hydrogen.

In certain embodiments of Formula 2, R$^4$ is C$_{5-12}$-heteroaryl. The heteroaryl may be, in certain embodiments, tetrazolyl, pyrazolyl, oxazolyl, imidazolyl, thiazolyl, thiophenyl, triazolyl, furanyl, isoxazolyl, oxadiazolyl, benzothiophenyl, pyridinyl, or pyrrolyl. More specifically, the heteroaryl may be tetrazol-5-yl, pyrazol-1-yl, 3-methylpyrazol-1-yl, oxazol-2-yl, oxazol-2-yl, imidazol-2-yl, thiazol-2-yl, thiazol-4-yl, thiophen-3-yl, 5-chloro-thiophen-2-yl, 1-methyl-imidazol-2-yl, imidazol-1-yl, pyrazol-3-yl, 2-methyl-thiazol-4-yl, furan-2-yl, 3,5-dimethyl-pyrazol-1-yl, 4,5-dihydrooxazol-2-yl, isoxazol-5-yl, [1,2,4]-oxadiazol-3-yl, benzo[b]thiophen-3-yl, oxazol-4-yl, furan-3-yl, 4-methyl-thiophen-2-yl, thiazol-5-yl, tetrazol-1-yl, [1,2,4] triazol-1-yl, 2-methyl-thiazol-5-yl, 1-methyl-pyrazol-4-yl, 2-thiolyl-imidaxol-1-yl, pyridin-2-yl, or 2,5-dimethyl-pyrrol-1-yl).

In certain embodiments of Formula 2, $R^3$ and $R^4$ together with the atoms to which they are attached may form a five or six-membered ring that optionally includes one or two heteroatoms selected from O, S and N. In many such embodiments $R^3$ and $R^4$ together with the atoms to which they are attached may form a five membered aromatic with one nitrogen, i.e. a pyrrol ring, a five membered aromatic with two nitrogens, i.e., a pyrazol or imidazol ring, a five membered aromatic with one nitrogen and one oxygen, i.e., an ox-azole or isoxazole ring; a five membered aromatic with one nitrogen and one sulfur, i.e., a thiazole or isothiazole ring; a five membered aromatic with one oxygen, i.e., a furanyl ring; or a five membered aromatic with one sulfur, i.e., a thiophenyl ring.

In a further embodiment of Formula 2, $R^1$ is $C_{1-12}$-alkyl, $C_{2-12}$-alkenyl, $C_{3-12}$-cycloalkyl, or halo, $R^3$ is $C_{1-12}$-alkoxy, hydroxy or halo, and $R^4$ is $C_{1-12}$-alkyl, $C_{2-12}$-alkynyl, cyano, $C_{0-12}$-sulfonamido, —COOH, halo, $C_{1-12}$-alkoxy, $C_{1-12}$-alkylsulfonyl or $C_{5-12}$-heteroaryl selected from tetrazolyl, pyrazolyl, oxazolyl, imidazolyl, thiazolyl, thiophenyl, triazolyl, furanyl, isoxazolyl, oxadiazolyl, benzothiophenyl, pyridinyl and pyrrolyl.

In another further embodiment of Formula 2, $R^1$ is $C_{1-12}$-alkyl, $C_{2-12}$-alkenyl, $C_{3-12}$-cycloalkyl, or halo, $R^3$ is $C_{1-12}$-alkoxy, hydroxy or halo, and $R^4$ is $C_{1-12}$-alkyl, $C_{2-12}$-alkynyl, cyano, $C_{0-12}$-sulfonamido, —COOH, halo, $C_{1-12}$-alkoxy or $C_{1-12}$-alkylsulfonyl.

In another further embodiment of Formula 2, $R^1$ is $C_{1-12}$-alkyl, $C_{2-12}$-alkenyl, $C_{3-12}$-cycloalkyl, or halo, $R^3$ is $C_{1-12}$-alkoxy, hydroxy or halo, and $R^4$ is $C_{5-12}$-heteroaryl selected from tetrazolyl, pyrazolyl, oxazolyl, imidazolyl, thiazolyl, thiophenyl, triazolyl, furanyl, isoxazolyl, oxadiazolyl, benzothiophenyl, pyridinyl and pyrrolyl.

In another further embodiment of Formula 2, $R^1$ is $C_{2-12}$-alkyl, $C_{2-12}$-alkenyl, $C_{3-12}$-cycloalkyl, or halo, $R^3$ is $C_{1-12}$-alkoxy, hydroxy or halo, $R^4$ is $C_{1-12}$-alkyl, $C_{2-12}$-alkynyl, cyano, $C_{0-12}$-sulfonamido, —COOH, halo, $C_{1-12}$-alkoxy or $C_{1-12}$-alkylsulfonyl, $R^7$ is hydrogen, and $R^d$ is hydrogen, $C_{1-12}$-alkyl, $C_{1-12}$-hydroxyalkyl or $C_{1-12}$-haloalkyl.

In another further embodiment of Formula 2, $R^1$ is $C_{1-12}$-alkyl, $C_{2-12}$-alkenyl, $C_{3-12}$-cycloalkyl, or halo, $R^3$ is $C_{1-12}$-alkoxy, hydroxy or halo, $R^4$ is $C_{5-12}$-heteroaryl selected from tetrazolyl, pyrazolyl, oxazolyl, imidazolyl, thiazolyl, thiophenyl, triazolyl, furanyl, isoxazolyl, oxadiazolyl, benzothiophenyl, pyridinyl and pyrrolyl, $R^7$ is hydrogen, and $R^d$ is hydrogen, $C_{1-12}$-alkyl, acetyl, $C_{1-12}$-hydroxyalkyl or $C_{1-12}$-haloalkyl.

In another further embodiment of Formula 2, $R^1$ is isopropyl, isopropenyl, cyclopropyl or iodo, $R^3$ is $C_{1-12}$-alkoxy, hydroxy or halo, and $R^4$ is $C_{1-12}$-alkyl, $C_{2-12}$-alkynyl, cyano, $C_{0-12}$-sulfonamido, —COOH, halo, $C_{1-12}$-alkoxy, $C_{1-12}$-alkylsulfonyl or $C_{5-12}$-heteroaryl.

In another further embodiment of Formula 2, $R^1$ is isopropyl, isopropenyl, cyclopropyl or iodo, $R^3$ is $C_{1-12}$-alkoxy, hydroxy or halo, $R^4$ is $C_{1-12}$-alkyl, $C_{2-12}$-alkynyl, cyano, $C_{0-12}$-sulfonamido, —COOH, halo, $C_{1-12}$-alkoxy, $C_{1-12}$-alkylsulfonyl or $C_{5-12}$-heteroaryl, $R^7$ is hydrogen, and $R^d$ is hydrogen, $C_{1-12}$-alkyl, $C_{1-12}$-hydroxyalkyl or $C_{1-12}$-haloalkyl.

In another further embodiment of Formula 2, $R^1$ is isopropyl or iodo, $R^3$ is methoxy, hydroxy, chloro, bromo or iodo, and $R^4$ is methoxy, methyl, cyano, bromo, chloro, iodo, —C≡C—$CH_3$, —C≡CH, —COOH, —$S(O)_2CH_3$, —$S(O)_2NH_2$ or tetrazolyl.

In another further embodiment of Formula 2, $R^1$ is isopropyl or iodo, $R^3$ is methoxy, hydroxy, chloro, bromo or iodo, $R^4$ methoxy, methyl, cyano, bromo, chloro, iodo, —C≡C—$CH_3$, —C≡CH, —COOH, —$S(O)_2CH_3$, —$S(O)_2NH_2$ or tetrazolyl, $R^7$ is hydrogen, and $R^d$ is hydrogen, $C_{1-12}$-alkyl, $C_{1-12}$-hydroxyalkyl or $C_{1-12}$-haloalkyl.

In another further embodiment of Formula 2, $R^1$ is isopropyl, $R^3$ is methoxy, hydroxy, chloro, bromo or iodo, and $R^4$ is methoxy, methyl, cyano, bromo, chloro, iodo, —C≡C—$CH_3$, —C≡CH, —COOH, —$S(O)_2CH_3$, —$S(O)_2NH_2$ or tetrazolyl.

In another further embodiment of Formula 2, $R^1$ is isopropyl, $R^3$ is methoxy, hydroxy, chloro, bromo or iodo, $R^4$ methoxy, methyl, cyano, bromo, chloro, iodo, —C≡C—$CH_3$, —C≡CH, —COOH, —$S(O)_2CH_3$, —$S(O)_2NH_2$ or tetrazolyl, $R^7$ is hydrogen, and $R^d$ is hydrogen, $C_{1-12}$-alkyl, $C_{1-12}$-hydroxyalkyl or $C_{1-12}$-haloalkyl.

In other embodiments of the present disclosure, the compounds may be of Formula 3:

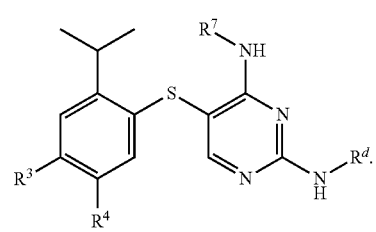

Formula 3 wherein:
  $R^3$ and $R^4$ each independently is: hydrogen; $C_{1-12}$-alkyl; $C_{2-12}$-alkenyl; $C_{2-12}$-alkynyl; amino; halo; amido; $C_{1-12}$-haloalkyl; $C_{1-12}$-alkoxy; hydroxy; $C_{1-12}$-haloalkoxy; nitro; $C_{1-12}$-hydroxyalkyl; $C_{2-12}$-alkoxyalkyl; $C_{1-12}$-hydroxyalkoxy; $C_{3-12}$-alkynylalkoxy; $C_{1-12}$-alkylsulfonyl; $C_{6-12}$-arylsulfonyl; cyano; $C_{6-12}$-aryl; $C_{5-12}$-heteroaryl; $C_{3-12}$-heterocyclyl; $C_{4-12}$-heterocyclylalkoxy; $C_{6-12}$-aryloxy; $C_{5-12}$-heteroaryloxy; $C_{7-12}$-arylalkyloxy; $C_{6-12}$-heteroaralkyloxy; optionally substituted phenoxy; —$(CH_2)_m$—$(Z)_n$—(CO)—$R^f$ or —$(CH_2)_m$—$(Z)_n$—$SO_2$—$(NR^g)_{n'}$—$R^f$, where m, n and n' are each independently 0 or 1,
  Z is O or $NR^g$,
  $R^f$ is hydrogen, $C_{1-12}$-alkyl, hydroxy, $C_{1-12}$alkoxy, amino, $C_{1-12}$-hydroxyalkyl or $C_{2-12}$-alkoxyalkyl, and each $R^g$ is independently hydrogen or $C_{1-12}$-alkyl;
  $R^3$ and $R^4$ together with the atoms to which they are attached may form a five or six-membered ring that optionally includes one or two heteroatoms selected from O, S and N;
  $R^7$ is selected from: hydrogen; $C_{1-12}$-alkyl; $C_{3-12}$-cycloalkyl; $C_{4-12}$-cycloalkylalkyl; $C_{1-12}$-haloalkyl; $C_{1-12}$- haloalkoxy; C$_{1-12}$-hydroxyalky; C$_{2-12}$-alkoxyalkyl; acetyl; C$_{1-12}$-alkylsulfonyl; C$_{2-12}$-alkylsulfonylalkyl; C$_{2-12}$-aminocarbonyloxyalkyl; C$_{2-12}$-hydroxycarbonylalkyl; C$_{2-12}$-hydroxyalkyloxycarbonylalkyl; C$_{6-12}$-aryl; C$_{7-12}$-arylalkyl; C$_{6-12}$-arylsulfonyl; C$_{5-12}$-heteroaryl; C$_{6-12}$-heteroarylalkyl; C$_{5-12}$-heteroarylsulfonyl; C$_{3-12}$-heterocyclyl; and C$_{4-12}$-heterocyclylalkyl; and R$^d$ is selected from: hydrogen; C$_{1-12}$-alkyl; C$_{3-12}$-cycloalkyl; C$_{4-12}$-cycloalkylalkyl; C$_{1-12}$-haloalkyl; C$_{1-12}$-haloalkoxy; C$_{1-12}$-hydroxyalky; C$_{2-12}$-alkoxyalkyl; acetyl; C$_{1-12}$-alkylsulfonyl; C$_{2-12}$-alkylsulfonylalkyl; C$_{2-12}$-aminocarbonyloxyalkyl; C$_{2-12}$-hydroxycarbonylalkyl; C$_{2-12}$-hydroxyalkyloxycarbonylalkyl; C$_{6-12}$-aryl; C$_{7-12}$-arylalkyl; C$_{6-12}$-arylsulfonyl; C$_{5-12}$-heteroaryl; C$_{6-12}$-heteroarylalkyl; C$_{5-12}$-heteroarylsulfonyl; C$_{3-12}$-heterocyclyl; and C$_{4-12}$-heterocyclylalkyl.

In certain embodiments Formula 3, R$^7$ is selected from: C$_{1-12}$-alkyl, C$_{3-12}$-cycloalkyl; C$_{4-12}$-cycloalkylalkyl; C$_{1-12}$-haloalkyl; C$_{1-12}$-hydroxyalky; C$_{2-12}$-alkoxyalkyl; C$_{2-12}$-alkylsulfonylalkyl; acetyl; C$_{1-12}$-alkylsulfonyl; C$_{6-12}$-aryl; C$_{7-12}$-arylalkyl; C$_{6-12}$-arylsulfonyl; C$_{5-12}$-heteroaryl; C$_{6-12}$-heteroarylalkyl; C$_{5-12}$-heteroarylsulfonyl; C$_{3-12}$-heterocyclyl; and C$_{4-12}$-heterocyclylalkyl.

In certain embodiments of Formula 3, R$^7$ is selected from C$_{1-12}$-alkyl, C$_{1-12}$-hydroxyalkyl and C$_{1-12}$-haloalkyl.

In certain embodiments of Formula 3, R$^d$ is selected from: C$_{1-12}$-alkyl, C$_{3-12}$-cycloalkyl; C$_{4-12}$cycloalkylalkyl; C$_{1-12}$-haloalkyl; C$_{1-12}$-hydroxyalky; C$_{2-12}$-alkoxyalkyl; C$_{2-12}$-alkylsulfonylalkyl; acetyl; C$_{1-12}$-alkylsulfonyl; C$_{6-12}$-aryl; C$_{7-12}$ arylalkyl; C$_{6-12}$-arylsulfonyl; C$_{5-12}$-heteroaryl; C$_{6-12}$-heteroarylalkyl; C$_{5-12}$-heteroarylsulfonyl; C$_{3-12}$-heterocyclyl; and C$_{4-12}$-heterocyclylalkyl.

In certain embodiments of Formula 3, R$^d$ is selected from: C$_{1-12}$-alkyl, C$_{1-12}$-hydroxyalkyl and C$_{1-12}$-haloalkyl.

In certain embodiments of Formula 3, R$^3$ and R$^4$ each independently is C$_{1-12}$-alkyl, C$_{2-12}$-alkynyl, cyano, C$_{0-12}$-sulfonamido, —COOH, C$_{5-12}$-heteroaryl, halo, C$_{1-12}$-alkoxy, C$_{1-12}$-halo-alkoxy or C$_{1-12}$-alkylsulfonyl.

In certain embodiments of Formula 3, R$^3$ is halo, C$_{1-12}$-alkoxy, C$_{1-12}$-haloalkoxy or hydroxy. In further embodiments, R$^3$ is methoxy, fluoro, or chloro. In particular embodiments, R$^3$ is methoxy. In certain embodiments R$^3$ is hydroxy.

In certain embodiments of Formula 3, R$^4$ is C$_{1-12}$-alkyl, C$_{2-12}$-alkynyl, cyano, C$_{0-12}$-sulfonamido, —COOH, halo, C$_{1-12}$-alkoxy, C$_{1-12}$-alkylsulfonyl or C$_{5-12}$-heteroaryl. In further embodiments, R$^4$ is methoxy, iodo, methanesulfonyl or C$_{5-12}$-heteroaryl. In particular embodiments, R$^4$ is methoxy, methyl, cyano, bromo, chloro, iodo, —C≡C—CH$_3$, —C≡CH, —COOH, —S(O)$_2$CH$_3$, —S(O)$_2$NH$_2$ or 5-tetrazolyl. In specific embodiments R$^4$ may be methoxy, while in other embodiments R$^4$ may be iodo.

In certain embodiments of Formula 3, R$^7$ and R$^d$ are hydrogen.

In certain embodiments of Formula 3, R$^4$ is C$_{5-12}$-heteroaryl. The heteroaryl may be, in certain embodiments, tetrazolyl, pyrazolyl, oxazolyl, imidazolyl, thiazolyl, thiophenyl, triazolyl, furanyl, isoxazolyl, oxadiazolyl, benzothiophenyl, pyridinyl, or pyrrolyl. More specifically, the heteroaryl may be tetrazol-5-yl, pyrazol-1-yl, 3-methylpyrazol-1-yl, oxazol-2-yl, oxazol-5-yl, imidazol-2-yl, thiazol-2-yl, thiazol-4-yl, thiophen-3-yl, 5-chloro-thiophen-2-yl, 1-methyl-imidazol-2-yl, imidazol-1-yl, pyrazol-3-yl, 2-methyl-thiazol-4-yl, furan-2-yl, 3,5-dimethyl-pyrazol-1-yl, 4,5-dihydrooxazol-2-yl, isoxazol-5-yl, [1,2,4]-oxa-diazol-3-yl, benzo[b]thiophen-3-yl, oxazol-4-yl, furan-3-yl, 4-methyl-thiophen-2-yl, thi-azol-5-yl, tetrazol-1-yl, [1, 2,4] triazol-1-yl, 2-methyl-thiazol-5-yl, 1-methyl-pyrazol-4-yl, 2-thiolyl-imidazol-1-yl, pyridin-2-yl, or 2,5-dimethyl-pyrrol-1-yl).

In certain embodiments of Formula 3, R$^3$ and R$^4$ together with the atoms to which they are attached may form a five or six-membered ring that optionally includes one or two heteroatoms selected from O, S and N; see Formula 4:

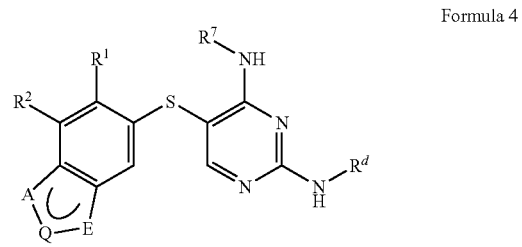

Formula 4 wherein:

R$^1$ is C$_{1-12}$-alkyl; C$_{2-12}$-alkenyl; C$_{3-12}$-cycloalkyl; or C$_{3-12}$-cycloalkenyl; or halo;

R$^2$ is hydrogen; C$_{1-12}$-alkyl; C$_{2-12}$-alkenyl; C$_{2-12}$-alkynyl; amino; halo; amido; C$_{1-12}$-haloalkyl; C$_{1-12}$-alkoxy; hydroxy; C$_{1-12}$-haloalkoxy; nitro; C$_{1-12}$-hydroxyalkyl; C$_{2-12}$-alkoxyalkyl; C$_{1-12}$-hydroxyalkoxy; C$_{3-12}$-alkynylalkoxy; C$_{1-12}$-alkylsulfonyl; C$_{6-12}$-arylsulfonyl; cyano; C$_{6-12}$-aryl; C$_{5-12}$-heteroaryl; C$_{3-12}$-heterocyclyl; C$_{4-12}$-heterocyclylalkoxy; C$_{6-12}$-aryloxy; C$_{5-12}$-heteroaryloxy; C$_{7-12}$-arylalkyloxy; C$_{6-12}$-heteroarylalkyloxy; optionally substituted phenoxy; or —(CH$_2$)$_m$—(Z)$_n$—(CO)—R$^f$ or —(CH$_2$)$_m$—(Z)$_n$—SO$_2$—(NR$^g$)$_{n'}$—R$^f$, where m, n and n' are each independently 0 or 1, Z is O or NR$^g$, R$^f$ is hydrogen, C$_{1-12}$-alkyl, hydroxy, C$_{1-12}$-alkoxy, amino, C$_{1-12}$-hydroxyalkyl or C$_{2-12}$-alkoxyalkyl, and each R$^g$ is independently hydrogen or C$_{1-12}$-alkyl;

R$^7$ is selected from: hydrogen; C$_{1-12}$-alkyl; C$_{3-12}$-cycloalkyl; C$_{4-12}$-cycloalkylalkyl; C$_{1-12}$-haloalkyl; C$_{1-12}$-haloalkoxy; C$_{1-12}$-hydroxyalky; C$_{2-12}$-alkoxyalkyl; acetyl; C$_{1-12}$-alkylsulfonyl; C$_{2-12}$-alkylsulfonylalkyl; C$_{2-12}$-aminocarbonyloxyalkyl; C$_{2-12}$-hydroxycarbonylalkyl; C$_{2-12}$-hydroxyalkyloxycarbonylalkyl; C$_{6-12}$-aryl; C$_{7-12}$-arylalkyl; C$_{6-12}$-arylsulfonyl; C$_{5-12}$-heteroaryl; C$_{6-12}$-heteroarylalkyl; C$_{5-12}$-heteroarylsulfonyl; C$_{3-12}$-heterocyclyl; and C$_{4-12}$-heterocyclylalkyl;

R$^d$ is selected from: hydrogen; C$_{1-12}$-alkyl; C$_{3-12}$-cycloalkyl; C$_{4-12}$-cycloalkylalkyl; C$_{1-12}$-haloalkyl; C$_{1-12}$-haloalkoxy; C$_{1-12}$-hydroxyalky; C$_{2-12}$-alkoxyalkyl; acetyl; C$_{1-12}$-alkylsulfonyl; C$_{2-12}$-alkylsulfonylalkyl; C$_{2-12}$-aminocarbonyloxyalkyl; C$_{2-12}$-hydroxycarbonylalkyl; C$_{2-12}$-hydroxyalkyloxycarbonylalkyl; C$_{6-12}$-aryl; C$_{7-12}$-arylalkyl; C$_{6-12}$-arylsulfonyl; C$_{5-12}$-heteroaryl; C$_{6-12}$-heteroarylalkyl; C$_{5-12}$-heteroarylsulfonyl; C$_{3-12}$-heterocyclyl; and C$_{4-12}$-heterocyclylalkyl;

Q is (CR$^9$)$_x$, one of A and E is O, S or NR$^{10}$ and the other is (CR$^9$)$_x$ or N, wherein each x is independently 1 or 2; or Q is N, one of A and E is NR$^{10}$ and the other is (CR$^9$)$_x$;

each R$^9$ is independently hydrogen, C$_{1-12}$-alkyl, halo or C$_{1-12}$-alkoxy; and R$^{10}$ is hydrogen, C$_{1-12}$-alkyl, C$_{1-12}$-hydroxyalkyl, C$_{2-12}$-alkoxyalkyl, —(CH$_2$)$_m$—(Z)$_n$—(CO)—R$^f$, or —(CH$_2$)$_m$—(Z)$_n$—SO$_2$—(NR$^g$)$_{n'}$—R$^f$.

In many such embodiments $R^3$ and $R^4$ together with the atoms to which they are attached may form: a five membered aromatic with one nitrogen, i.e. a pyrrole ring; a five membered aromatic with two nitrogens, i.e. a pyrazole or imidazole ring; a five membered aromatic with one nitrogen and one oxygen, i.e., an oxazole or isoxazole ring; a five membered aromatic with one nitrogen and one sulfur, i.e., a thiazole or isothiazole ring; a five membered aromatic with one oxygen, i.e., a furanyl ring; or a five membered aromatic with one sulfur, i.e., a thiophenyl ring.

In additional embodiments, $R^3$ and $R^4$ together with the atoms to which they are attached may form a six membered cycloalkyl, heterocyclic, aromatic or heteroaromatic ring, e.g., a heterocycle or heteroaromatic with one nitrogen (e.g., a tetrahydroquinoline or a quinoline) a six membered heterocycle or heteroaromatic with two nitrogens, e.g., a tetrahydrocinnoline/tetrahydroquinazoline/tetrahydroquinoxaline or a cinnoline/quinazoline/quinoxaline ring; a six membered heterocycle with one nitrogen and one oxygen, i.e., a benzoxazine ring; a six membered heterocycle or with one nitrogen and one sulfur, i.e., a benzothiazine ring; a six membered heterocycle with one oxygen, i.e., a chromane ring; or a six membered heterocycle with one sulfur, i.e., a thiochromane ring.

In certain embodiments of Formula 4, A is $NR^{10}$, Q and E are $CR^9$, and x=1; in certain embodiments of Formula 4, A is $NR^{10}$, Q and E are $CR^9$, and x=2.

In certain embodiments of Formula 4, E is $NR^{10}$, A and Q are $CR^9$, and x=1; in certain embodiments of Formula 4, E is $NR^{10}$, A and Q are $CR^9$, and x=2.

In certain embodiments of Formula 4, Q is $NR^{10}$, A and E are CR, and x=1; in certain embodiments of Formula 4, Q is $NR^{10}$, A and E are CR, and x=2.

In certain embodiments of Formula 4, A is O, E is N, Q is $CR^9$, and x=1; in certain embodiments of Formula 4, A is O, E is N, Q is $CR^9$, and x=2.

In certain embodiments of Formula 4, A is N, E is O, Q is $CR^9$, and x=1; in certain embodiments of Formula 4, A is N, E is O, Q is $CR^9$, and x=2.

In certain embodiments of Formula 4, A is S, E is N, Q is $CR^9$, and x=1; in certain embodiments of Formula 4, A is S, E is N, Q is $CR^9$, and x=2.

In certain embodiments of Formula 4, A is N, E is S, Q is $CR^9$, and x=1; in certain embodiments of Formula 4. A is N, E is S, Q is $CR^9$, and x=2.

In certain embodiments of Formula 4, E is S, A and Q are $CR^9$, and x=1; in certain embodiments of Formula 4, E is S, A and Q are $CR^9$, and x=2.

In certain embodiments of Formula 4, E is O, A and Q are $CR^9$, and x=1; in certain embodiments of Formula 4, E is O, A and Q are $CR^9$, and x=2.

In certain embodiments of Formula 4, A is S, E and Q are $CR^9$, and x=1; in certain embodiments of Formula 4, A is S, E and Q are $CR^9$, and x=2.

In certain embodiments of Formula 4, A is O, E and Q are $CR^9$ and x=1; in certain embodiments of Formula 4, A is O, E and Q are $CR^9$, and x=2.

In certain embodiments of Formula 4, A is $NR^{10}$, Q is N, E is $CR^9$, and x=1; in certain embodiments of Formula 4, A is $NR^{10}$, Q is N, E is $CR^9$, and x=2.

In certain embodiments of Formula 4, E is $NR^{10}$, Q is N, A is $CR^9$, and x=1; in certain embodiments of Formula 4, E is $NR^{10}$, Q is N, A is $CR^9$, and x=2.

In certain embodiments of Formula 4, $R^2$ is hydrogen.

In certain embodiments of Formula 4, $R^1$ is $C_{1-12}$-alkyl, $C_{2-12}$-alkenyl or $C_{3-12}$-cycloalkyl. In further embodiments, $R^1$ is ethyl, cyclopropyl, isopropenyl or isopropyl. In particular embodiments, $R^1$ is isopropyl. In particular embodiments, $R^1$ is ethyl. In particular embodiments, $R^1$ is cyclopropyl.

In certain embodiments of Formula 4, $R^7$ is selected from: $C_{1-12}$-alkyl, $C_{3-12}$-cycloalkyl; $C_{4-12}$-cycloalkylalkyl; $C_{1-12}$-haloalkyl; $C_{1-12}$-hydroxyalky; $C_{2-12}$-alkoxyalkyl; $C_{2-12}$-alkylsulfonylalkyl; acetyl; $C_{1-12}$-alkylsulfonyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

In certain embodiments of Formula 4, $R^7$ is selected from: $C_{1-12}$-alkyl, $C_{1-12}$-hydroxyalkyl and $C_{1-12}$-haloalkyl.

In certain embodiments of Formula 4, $R^d$ is selected from: $C_{1-12}$-alkyl, $C_{3-12}$-cycloalkyl; $C_{4-12}$-cycloalkylalkyl; $C_{1-12}$-haloalkyl; $C_{1-12}$-hydroxyalky; $C_{2-12}$-alkoxyalkyl; $C_{2-12}$-alkylsulfonylalkyl; acetyl; $C_{1-12}$-alkylsulfonyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

In certain embodiments of Formula 4, $R^d$ is selected from: $C_{1-12}$-alkyl, $C_{1-12}$-hydroxyalkyl and $C_{1-12}$-haloalkyl.

In certain embodiments of Formula 4, $R^7$ and $R^d$ are hydrogen.

In some embodiments of the present disclosure, the compounds may be of Formula 5:

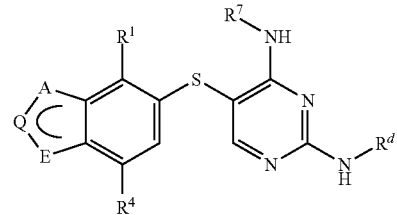

Formula 5 wherein:
- $R^1$ is: $C_{1-12}$-alkyl; $C_{2-12}$-alkenyl; $C_{3-12}$-cycloalkyl; or $C_{3-12}$-cycloalkenyl; or halo;
- $R^4$ is: hydrogen; $C_{1-12}$-alkyl; $C_{2-12}$-alkenyl; $C_{2-12}$-alkynyl; amino; halo; amigo; $C_{1-12}$-haloalkyl; $C_{1-12}$-alkoxy; hydroxy; $C_{1-12}$-haloalkoxy; nitro; $C_{1-12}$-hydroxyalkyl; $C_{2-12}$-alkoxyalkyl; $C_{1-12}$-hydroxyalkoxy; $C_{3-12}$-alkynylalkoxy; $C_{1-12}$-alkylsulfonyl; $C_{6-12}$-arylsulfonyl; cyano; $C_{6-12}$-aryl; $C_{5-12}$-heteroaryl; $C_{3-12}$-heterocyclyl; $C_{4-12}$-heterocyclylalkoxy; $C_{6-12}$-aryloxy; $C_{5-12}$-heteroaryloxy; $C_{2-12}$-arylalkyloxy; $C_{6-12}$-heteroarylalkyloxy; optionally substituted phenoxy; or —$(CH_2)_m$—$(Z)_n$—(CO)—$R^f$ or —$(CH_2)_m$—$(Z)_n$—$SO_2$—$(NR^g)_{n'}$—$R^f$, where m, n and n' are each independently 0 or 1,
- Z is O or $NR^g$, $R^f$ is hydrogen, $C_{1-12}$-alkyl, hydroxy, $C_{1-12}$-alkoxy, amino, $C_{1-12}$-hydroxyalkyl or $C_{2-12}$-alkoxyalkyl, and each $R^g$ is independently hydrogen or alkyl;
- $R^7$ is selected from hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl;

$R^d$ is selected from: hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl;

Q is $(CR^9)_x$, one of A and E is O, S or $NR^{10}$ and the other is $(CR^9)_x$ or N, wherein each x is independently 1 or 2; or Q is N, one of A and E is $NR^{10}$ and the other is $(CR^9)_x$;

each $R^9$ is independently hydrogen, $C_{3-12}$-alkyl, halo or $C_{1-12}$-alkoxy; and $R^{10}$ is hydrogen, $C_{1-12}$-alkyl, $C_{1-12}$-hydroxyalkyl, $C_{2-12}$-alkoxyalkyl, —$(CH_2)_m$—$(Z)_n$—$(CO)$—$R^f$, or —$(CH_2)_m$—$(Z)_n$—$SO_2$—$(NR^g)_n$—$R^f$.

In certain embodiments of Formula 5, A is $NR^{10}$, Q and E are $CR^9$ and x=1; in certain embodiments of Formula 5, A is $NR^{10}$, Q and E are $CR^9$ and x=2.

In certain embodiments of Formula 5 E is $NR^{10}$, A and Q are $CR^9$, and x=1; in certain embodiments of Formula 5, E is $NR^{10}$, A and Q are $CR^9$, and x=2.

In certain embodiments of Formula 5, Q is $NR^{10}$, A and E are $CR^9$, and x=1; in certain embodiments of Formula 5, Q is $NR^{10}$, A and E are $CR^9$, and x=2.

In certain embodiments of Formula 5, A is O, E is N, Q is $CR^9$, and x=1; in certain embodiments of Formula 5, A is O, E is N, Q is $CR^9$, and x=2.

In certain embodiments of Formula 5, A is N, E is O, Q is $CR^9$, and x=1; in certain embodiments of Formula 5, A is N, E is O, Q is $CR^9$, and x=2.

In certain embodiments of Formula 5, A is S, E is N, Q is $CR^9$, and x=1; in certain embodiments of Formula 5, A is N, E is O, Q is $CR^9$, and x=2.

In certain embodiments of Formula 5, A is N, E is S, Q is $CR^9$, and x=1; in certain embodiments of Formula 5, A is N, E is S, Q is $CR^9$, and x=2.

In certain embodiments of Formula 5, E is S, A and Q are $CR^9$, and x=1; in certain embodiments of Formula 5, E is S, A and Q are $CR^9$, and x=2.

In certain embodiments of Formula 5, E is O, A and Q are $CR^9$ and x=1; in certain embodiments of Formula 5, E is O, A and Q are $CR^9$, and x=2.

In certain embodiments of Formula 5, A is S, E and Q are $CR^9$, and x=1; certain embodiments of Formula 5, A is S, E and Q are $CR^9$, and x=2.

In certain embodiments of Formula 5, A is O, E and Q are $CR^9$, and x=1; in certain embodiments of Formula 5, A is O, E and Q are $CR^9$, and x=2.

In certain embodiments of Formula 5, A is $NR^{10}$, Q is N, E is $CR^9$, and x=1; in certain embodiments of Formula 5, A is $NR^{10}$, Q is N, E is $CR^9$, and x=2.

In certain embodiments of Formula 5, E is $NR^{10}$, Q is N, A is $CR^9$, and x=1; in certain embodiments of Formula 5, E is $NR^{10}$, Q is N, A is $CR^9$, and x=2.

In certain embodiments of Formula 5, $R^1$ is $C_{1-12}$-alkyl, $C_{2-12}$-alkenyl or $C_{3-12}$-cycloalkyl. Preferably, $R^1$ is ethyl, cyclopropyl, isopropenyl or isopropyl. In certain embodiments, $R^1$ is isopropyl. In particular embodiments, $R^1$ is ethyl. In particular embodiments, $R^1$ is cyclopropyl.

In certain embodiments of Formula 5, $R^7$ is selected from: $C_{1-12}$-alkyl, $C_{3-12}$-cycloalkyl; $C_{4-12}$-cycloalkylalkyl; $C_{1-12}$-haloalkyl; $C_{1-12}$-hydroxyalky; $C_{2-12}$-alkoxyalkyl; $C_{2-12}$-alkylsulfonylalkyl; acetyl; $C_{1-12}$-alkylsulfonyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

In certain embodiments of Formula 5, $R^7$ is selected from $C_{1-12}$-alkyl, $C_{1-12}$-hydroxyalkyl and $C_{1-12}$-haloalkyl.

In certain embodiments of Formula 5, $R^d$ is selected from: $C_{1-12}$-alkyl, $C_{3-12}$-cycloalkyl; $C_{4-12}$-cycloalkylalkyl; $C_{1-12}$-haloalkyl; $C_{1-12}$-hydroxyalky; $C_{2-12}$-alkoxyalkyl; $C_{2-12}$-alkylsulfonylalkyl; acetyl; $C_{1-12}$-alkylsulfonyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

In certain embodiments of Formula 5, $R^d$ is selected from $C_{1-12}$-alkyl, $C_{1-12}$-hydroxyalkyl and $C_{1-12}$-haloalkyl.

In certain embodiments of Formula 5, $R^7$ and $R^d$ are hydrogen.

In certain embodiments of Formula 1, $R^4$ is $C_{1-12}$-alkyl, $C_{2-12}$-alkynyl, cyano, $C_{0-12}$-sulfonamido, —COOH, halo, $C_{1-12}$-alkoxy, $C_{1-12}$-alkylsulfonyl or $C_{5-12}$-heteroaryl. In further embodiments, $R^4$ is methoxy, iodo, methanesulfonyl or $C_{5-12}$-heteroaryl. In particular embodiments, $R^4$ is methoxy, methyl, cyano, bromo, chloro, iodo, —C≡C—$CH_3$, —C≡CH, —COOH, —$S(O)_2CH_3$, —$S(O)_2NH_2$ or tetrazolyl. In specific embodiments $R^4$ may be methoxy, while in other embodiments $R^4$ may be iodo.

In certain embodiments of Formula 5, $R^4$ is $C_{5-12}$-heteroaryl. The $C_{5-12}$-heteroaryl may be, in certain embodiments, tetrazolyl, pyrazolyl, oxazolyl, imidazolyl, thiazolyl, thiophenyl, triazolyl, furanyl, isoxazolyl, oxadiazolyl, benzothiophenyl, pyridinyl, or pyrrolyl. More specifically, the heteroaryl may be tetrazol-5-yl, pyrazol-1-yl, 3-methylpyrazol-1-yl, oxazol-2-yl, oxazol-5-yl, imidazol-2-yl, thiazol-2-yl, thiazol-4-yl, thiophen-3-yl, 5-chloro-thio-phen-2-yl, 1-methyl-imidazol-2-yl, imidazol-1-yl, pyrazol-3-yl, 2-methyl-thiazol-4-yl, furan-2-yl, 3,5-dimethyl-pyrazol-1-yl, 4,5-dihydrooxazol-2-yl, isoxazol-5-yl, [1,2,4]-oxa-diazol-3-yl, benzo [b] thiophen-3-yl, oxazol-4-yl, furan-3-yl, 4-methyl-thiophen-2-yl, thiazol-5-yl, tetrazol-1-yl, [1,2,4] triazol-1-yl, 2-methyl-thiazol-5-yl, 1-methyl-pyrazol-4-yl, 2-thiolyl-imidazol-1-yl, pyridin-2-yl, or 2,5-dimethyl-pyrrol-1-yl).

In embodiments of the present disclosure, where any of $R^7$ or $R^d$ are $C_{3-12}$-heterocyclyl or a group that includes a heterocyclyl moiety, such heterocyclyl or heterocyclyl moiety may be piperidinyl, piperazinyl, tetrahydrofuranyl, tetrahydrothiopyranyl, or 1,1-dioxotetrahydrothio-pyranyl. More preferably, such heterocyclyl or heterocyclyl moiety may be piperidin-4-yl, 1-methyl-piperidine-4-yl, 1-methanesulfonyl-piperidin-4-yl, tetrahydropyran-4-yl, tetra-hydrothiopyran-4-yl, or 1,1-dioxotrahydrothiopyran-4-yl.

Where any of $R^1$, $R^2$, $R^3$, $R^4$, $R^5$, $R^6$, $R^7$, $R^9$, $R^{10}$, $R^c$, $R^d$, $R^f$, $R^g$, or $R^h$ is $C_{1-12}$-alkyl or contains an alkyl moiety, such alkyl is preferably lower alkyl, i.e. $C_{1-6}$-alkyl, and more preferably $C_{1-4}$-alkyl.

The present disclosure also provides methods for treating a disease or condition by using a P2X3 receptor antagonist, a P2X2/3 receptor antagonist, or both, the method comprising administering to a subject in need thereof an effective amount of a compound of any of Formulae 1 to 5. The disease may be genitorurinary disease or urinary tract disease. In other instances the disease may be a disease is associated with pain. The urinary tract disease may be: reduced bladder capacity; frequent micturition; urge incontinence; stress incontinence; bladder hyperreactivity; benign prostatic hypertrophy; prostatitis; detrusor hyperreflexia; urinary frequency; nocturia; urinary urgency; overactive bladder; pelvic hypersensitivity; urethritis; prostatitits; pelvic pain syndrome; prostatodynia; cystitis; or idiophatic bladder hypersensitivity.

The disease associated with pain may be: inflammatory pain; surgical pain; visceral pain; dental pain; premenstrual pain; central pain; pain due to burns; migraine or cluster headaches; nerve injury neuritis; neuralgias; neuropathy; poisoning, ischemic injury; interstitial cystitis; cancer pain; viral, parasitic or bacterial infection; post-traumatic injury; pain associated with irritable bowel syndrome, inflammatory bowel disease; or the like.

In certain aspects, the present disclosure also provides methods for treating cough or urge to cough associated with a respiratory disease, hypertension, heart failure, dyspnea, sleep apnea, fatigue, exercise intolerance, by altering carotid body tonicity or activity in a subject, and the like. In additional instances the disorders or disease states may include hepatocellular carcinoma, tinnitus, migraine itch, diabetes endometriosis and dysmenorrhea, peripheral artery occlusive disease (PAOD), chronic obstructive pulmonary disease (COPD), atopic dermatitis and other forms of eczema or dermatitis, bursitis, tendonitis, fibromyalgia, gout, joint replacement, lichen sclerosus, psoriasis and psoriatic arthritis, cold sores, kidney stones, gall stones, smell disorders, taste disorders including dysgeusia or burning mouth syndrome, gastro esophageal reflux disease (GERD), binge-eating disorders and obesity, or pain from sickle cell anemia and ischemia.

In some embodiments of the method for treating a disease mediated by a P2X3 receptor antagonist, a P2X2/3 receptor antagonist, or both, comprises administering to a subject in need thereof an effective amount of a compound of any one of Formulae 1 to 5 which shows selectivity for P2X3 vs P2X2/3. For example when the diseases to be treated is medicated by at least the P2X3 receptor, the compound may show greater selectivity for P2X3 than P2X2/3.

In this way the present disclosure may provide a treatment which has reduced side effects, for example reduced taste effects.

Representative compounds in accordance with the methods of the present disclosure are shown in Table 1.

TABLE 1

| Compound # | Structure | MW Found [M + H]+ |
|---|---|---|
| 1 | 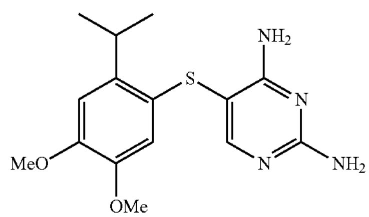 [SMILES: COc1cc(Sc2cnc(N)nc2N)c(C(C)C)cc1OC] | 321.2 |
| 2 | 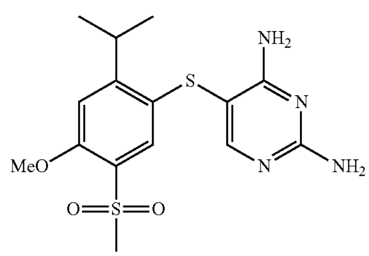 [SMILES: COc1cc(C(C)C)c(Sc2cnc(N)nc2N)cc1S(C)(=O)=O] | 369.0 |
| 3 | 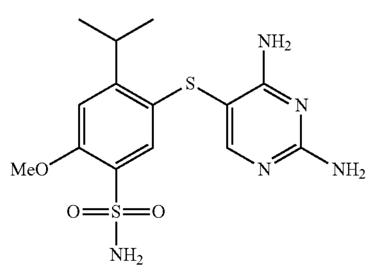 [SMILES: COc1cc(C(C)C)c(Sc2cnc(N)nc2N)cc1S(N)(=O)=O] | 370.0 |
| 4 | 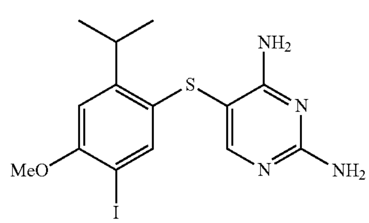 [SMILES: COc1cc(C(C)C)c(Sc2cnc(N)nc2N)cc1I] | 417.0 |

TABLE 1-continued
| Compound # | Structure | MW Found [M + H]+ |
|---|---|---|
| 5 | 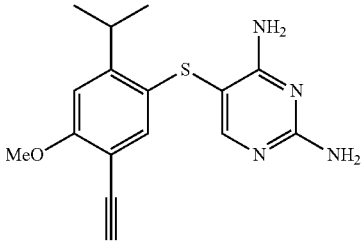 [SMILES: C#Cc1cc(Sc2cnc(N)nc2N)c(C(C)C)cc1OC] | 315.0 |
| 6 | 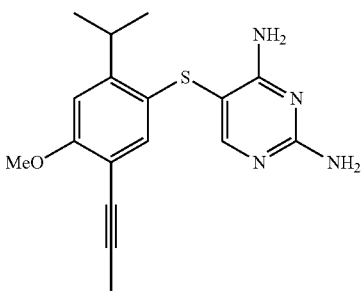 [SMILES: CC#Cc1cc(Sc2cnc(N)nc2N)c(C(C)C)cc1OC] | 329.1 |
| 7 | 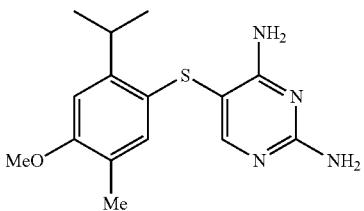 | 305.0 |
| 8 | 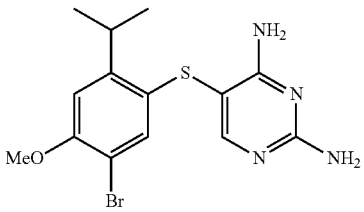 [SMILES: COc1cc(C(C)C)c(Sc2cnc(N)nc2N)cc1Br] | 368.9 |
| 9 | 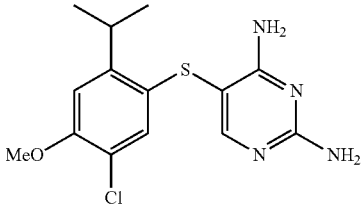 [SMILES: COc1cc(C(C)C)c(Sc2cnc(N)nc2N)cc1Cl] | 325.0 |
| 10 | 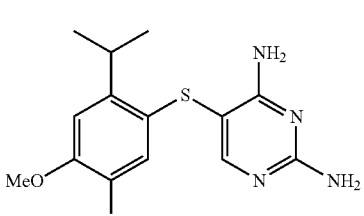 | 316.1 |

TABLE 1-continued

| Compound # | Structure | MW Found [M + H]+ |
|---|---|---|
| 11 | 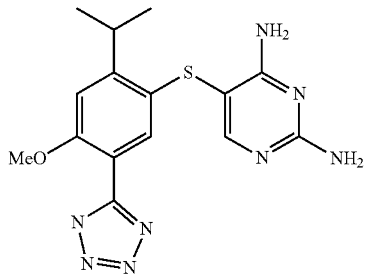 [SMILES: COc1cc(C(C)C)c(Sc2cnc(N)nc2N)cc1-c1nnn[nH]1] | 359.1 |
| 12 | 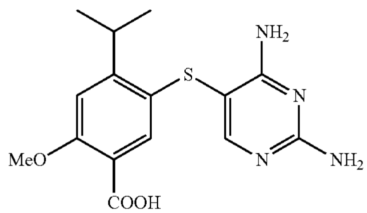 [SMILES: COc1cc(C(C)C)c(Sc2cnc(N)nc2N)cc1C(=O)O] | 335.1 |
| 13 | 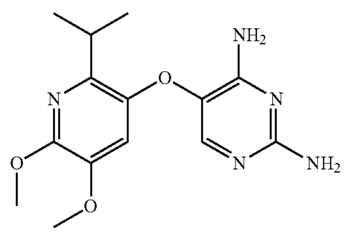 [SMILES: COc1cc(Oc2cnc(N)nc2N)c(C(C)C)nc1OC] | 306.0 |
| 14 | 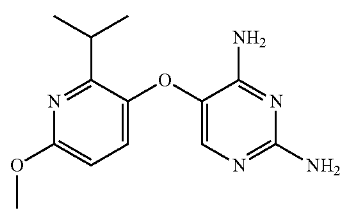 [SMILES: COc1ccc(Oc2cnc(N)nc2N)c(C(C)C)n1] | 276.1 |
| 15 | 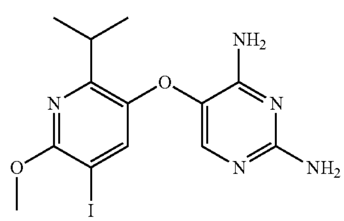 [SMILES: COc1nc(C(C)C)c(Oc2cnc(N)nc2N)cc1I] | 401.9 |
| 16 | 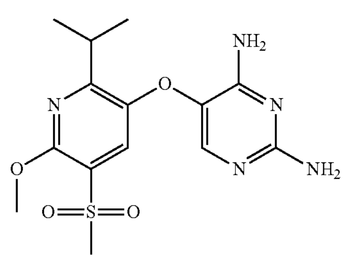 [SMILES: COc1nc(C(C)C)c(Oc2cnc(N)nc2N)cc1S(C)(=O)=O] | 354.1 |

TABLE 1-continued

| Compound # | Structure | MW Found [M + H]+ |
| --- | --- | --- |
| 17 | 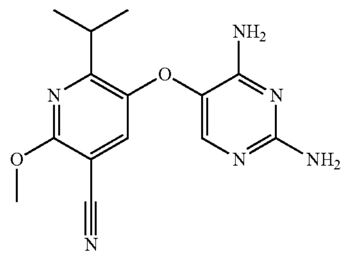 [SMILES: COc1nc(C(C)C)c(Oc2cnc(N)nc2N)cc1C#N] | 301.1 |
| 18 | 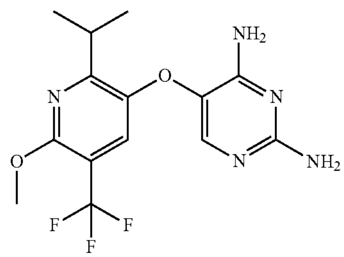 [SMILES: COc1nc(C(C)C)c(Oc2cnc(N)nc2N)cc1C(F)(F)F] | 344.2 |
| 19 | 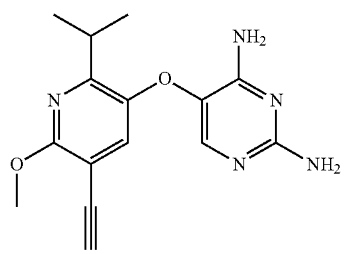 [SMILES: C#Cc1cc(Oc2cnc(N)nc2N)c(C(C)C)nc1OC] | 300.1 |
| 20 | 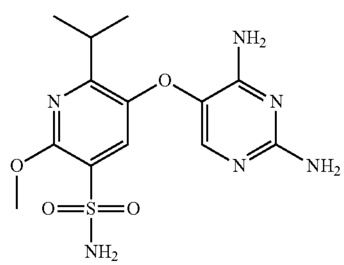 [SMILES: COc1nc(C(C)C)c(Oc2cnc(N)nc2N)cc1S(N)(=O)=O] | 355.0 |
| 21 | 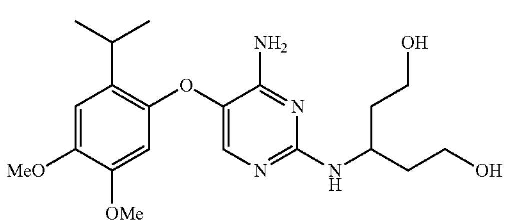 [SMILES: COc1cc(Oc2cnc(NC(CCO)CCO)nc2N)c(C(C)C)cc1OC] | 407.3 |
| 22 | 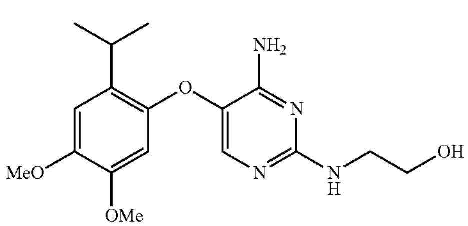 [SMILES: COc1cc(Oc2cnc(NCCO)nc2N)c(C(C)C)cc1OC] | 349.2 |

TABLE 1-continued

| Compound # | Structure | MW Found [M + H]+ |
|---|---|---|
| 23 | 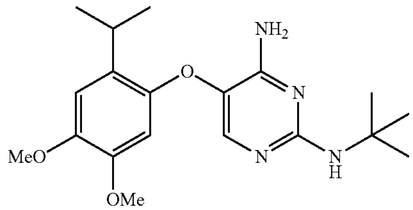 [SMILES: COc1cc(Oc2cnc(NC(C)(C)C)nc2N)c(C(C)C)cc1OC] | 361.2 |
| 24 | 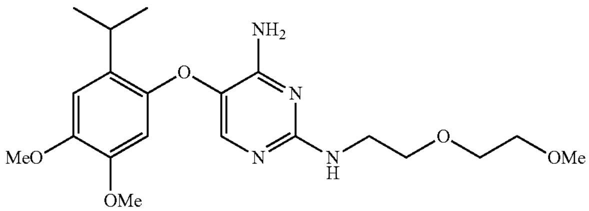 [SMILES: COCCOCCNc1ncc(Oc2cc(OC)c(OC)cc2C(C)C)c(N)n1] | 407.2 |
| 25 | 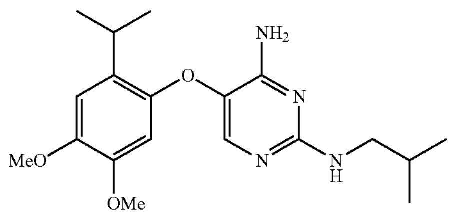 [SMILES: COc1cc(Oc2cnc(NCC(C)C)nc2N)c(C(C)C)cc1OC] | 361.2 |
| 26 | 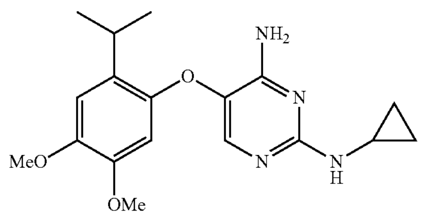 [SMILES: COc1cc(Oc2cnc(NC3CC3)nc2N)c(C(C)C)cc1OC] | 345.3 |
| 27 | 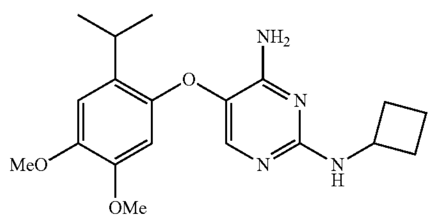 [SMILES: COc1cc(Oc2cnc(NC3CCC3)nc2N)c(C(C)C)cc1OC] | 359.2 |
| 28 | 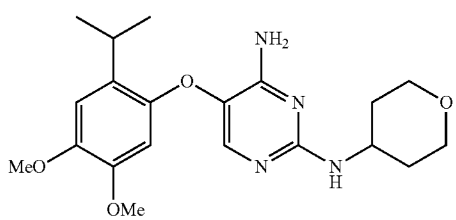 [SMILES: COc1cc(Oc2cnc(NC3CCOCC3)nc2N)c(C(C)C)cc1OC] | 389.2 |
| 29 | 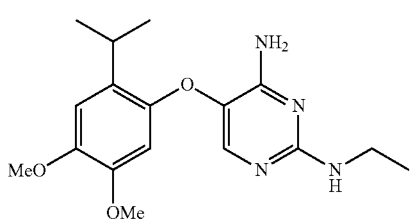 [SMILES: CCNc1ncc(Oc2cc(OC)c(OC)cc2C(C)C)c(N)n1] | 333.2 |

TABLE 1-continued

| Compound # | Structure | MW Found [M + H]+ |
|---|---|---|
| 30 | 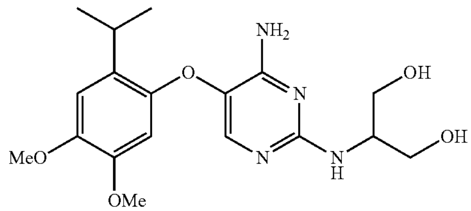 [SMILES: COc1cc(Oc2cnc(NC(CO)CO)nc2N)c(C(C)C)cc1OC] | 379.2 |
| 31 | 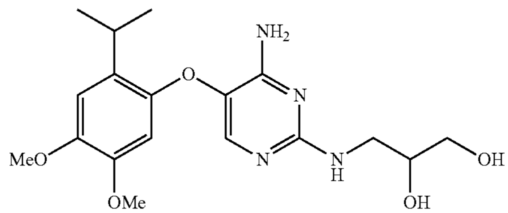 [SMILES: COc1cc(Oc2cnc(NCC(O)CO)nc2N)c(C(C)C)cc1OC] | 379.2 |
| 32 | 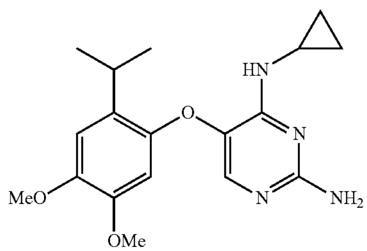 [SMILES: COc1cc(Oc2cnc(N)nc2NC2CC2)c(C(C)C)cc1OC] | 345.2 |
| 33 | 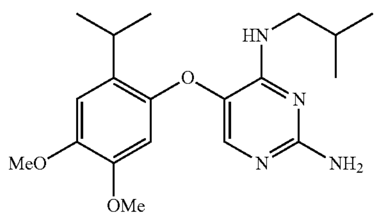 [SMILES: COc1cc(Oc2cnc(N)nc2NCC(C)C)c(C(C)C)cc1OC] | 361.2 |
| 34 | 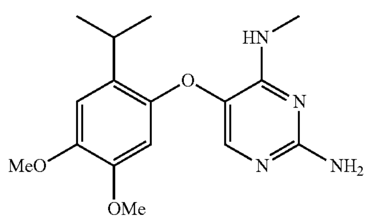 [SMILES: CNc1nc(N)ncc1Oc1cc(OC)c(OC)cc1C(C)C] | 319.3 |
| 35 | 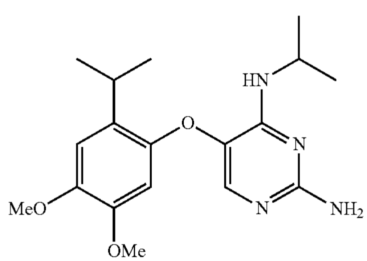 [SMILES: COc1cc(Oc2cnc(N)nc2NC(C)C)c(C(C)C)cc1OC] | 347.2 |
| 36 | 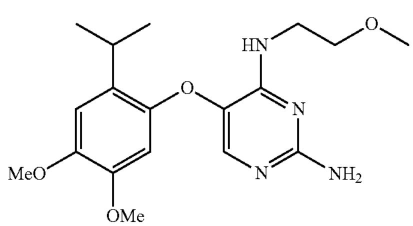 [SMILES: COCCNc1nc(N)ncc1Oc1cc(OC)c(OC)cc1C(C)C] | 363.2 |

TABLE 1-continued

| Compound # | Structure | MW Found [M + H]+ |
|---|---|---|
| 37 | 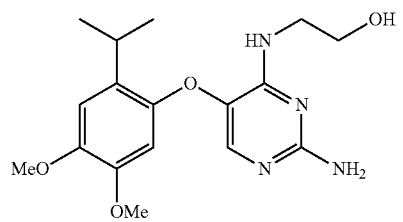 [SMILES: COc1cc(Oc2cnc(N)nc2NCCO)c(C(C)C)cc1OC] | 349.1 |
| 38 | 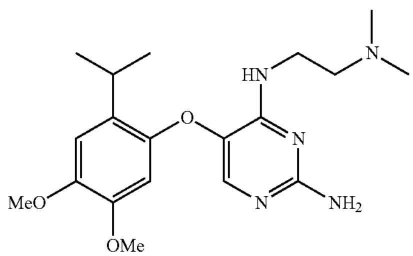 [SMILES: COc1cc(Oc2cnc(N)nc2NCCN(C)C)c(C(C)C)cc1OC] | 376.3 |
| 39 | 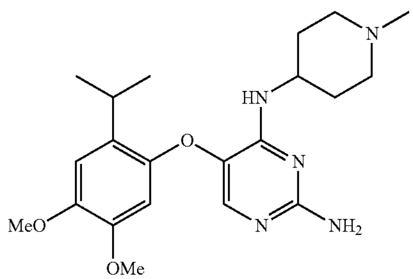 [SMILES: COc1cc(Oc2cnc(N)nc2NC2CCN(C)CC2)c(C(C)C)cc1OC] | 402.3 |
| 40 | 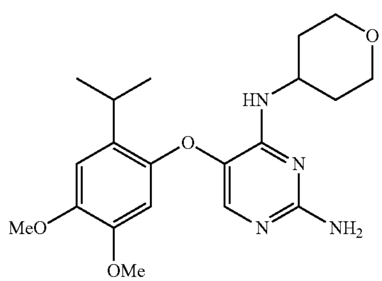 [SMILES: COc1cc(Oc2cnc(N)nc2NC2CCOCC2)c(C(C)C)cc1OC] | 389.2 |
| 41 | 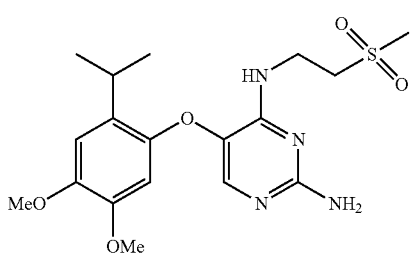 [SMILES: COc1cc(Oc2cnc(N)nc2NCCS(C)(=O)=O)c(C(C)C)cc1OC] | 411.3 |
| 42 | 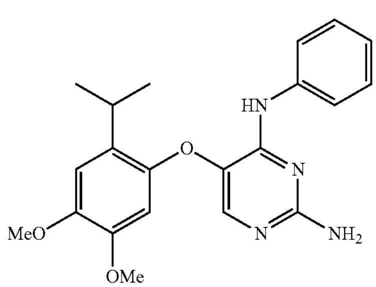 [SMILES: COc1cc(Oc2cnc(N)nc2Nc2ccccc2)c(C(C)C)cc1OC] | 381.2 |

TABLE 1-continued

| Compound # | Structure | MW Found [M + H]+ |
|---|---|---|
| 43 | 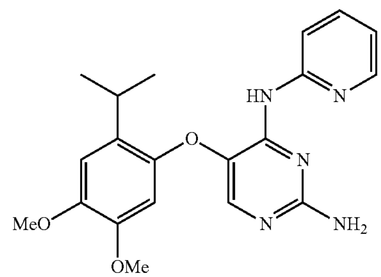 | 382.3 |
| 44 | 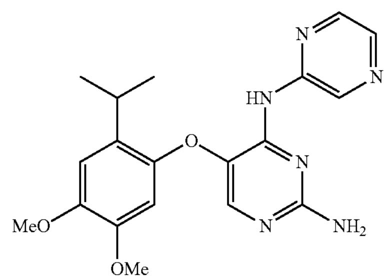 [SMILES: COc1cc(Oc2cnc(N)nc2Nc2cnccn2)c(C(C)C)cc1OC] | 383.3 |
| 45 | 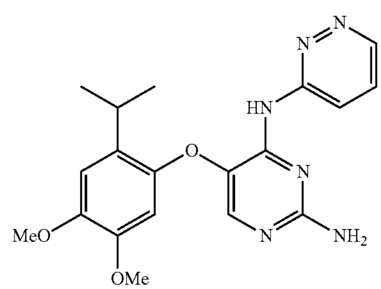 [SMILES: COc1cc(Oc2cnc(N)nc2Nc2cccnn2)c(C(C)C)cc1OC] | 383.1 |
| 46 | 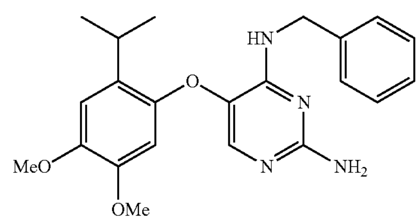 [SMILES: COc1cc(Oc2cnc(N)nc2NCc2ccccc2)c(C(C)C)cc1OC] | 395.2 |
| 47 | AF056 | |

Compounds of the present disclosure can be made by a variety of methods depicted in the illustrative synthetic reaction schemes shown and described herein.

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 1991, Volumes 1-40. The following synthetic reaction schemes are merely illustrative of some methods by which the compounds of the present disclosure can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature (RT), e.g., about 20° C.

Scheme A illustrates one synthetic procedure usable to prepare specific compounds of Formula (1):

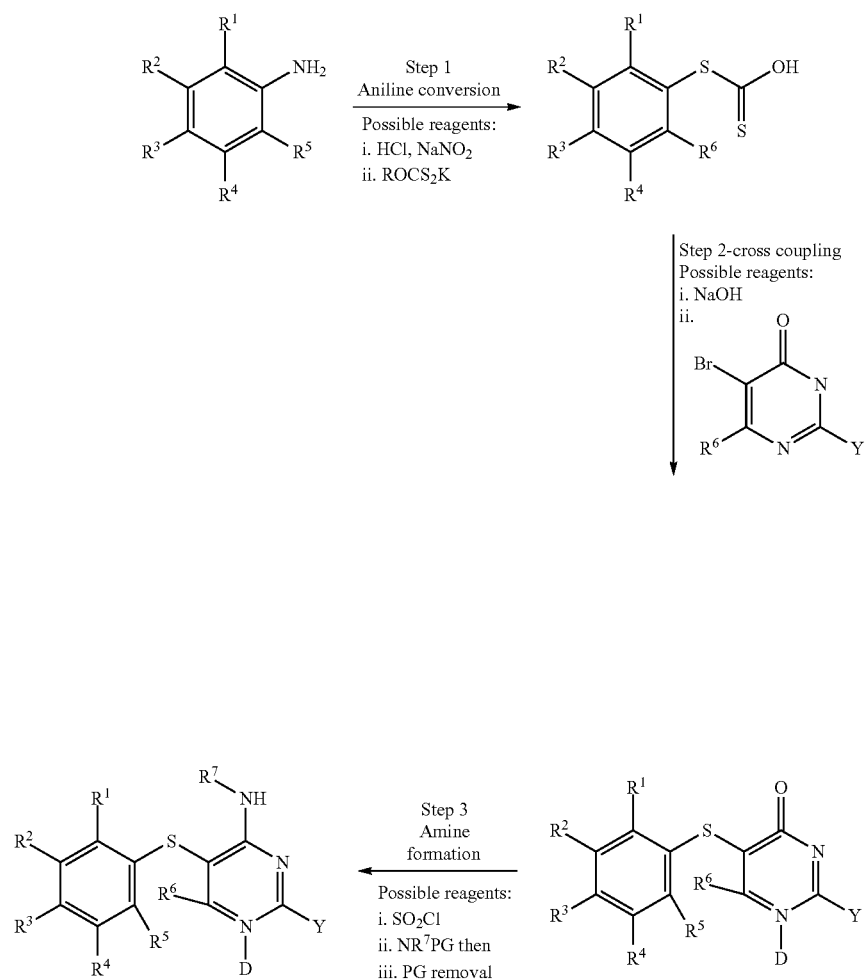

Generally speaking, Scheme A contemplates:

reaction of an optionally substituted aniline with ROCS$_2$K;

reaction of the resulting thioester with a bromo-pyrimidine oxide; and aminating the resulting polycyclic compound.

Scheme B illustrates another synthetic procedure usable to prepare specific compounds of Formula (1):
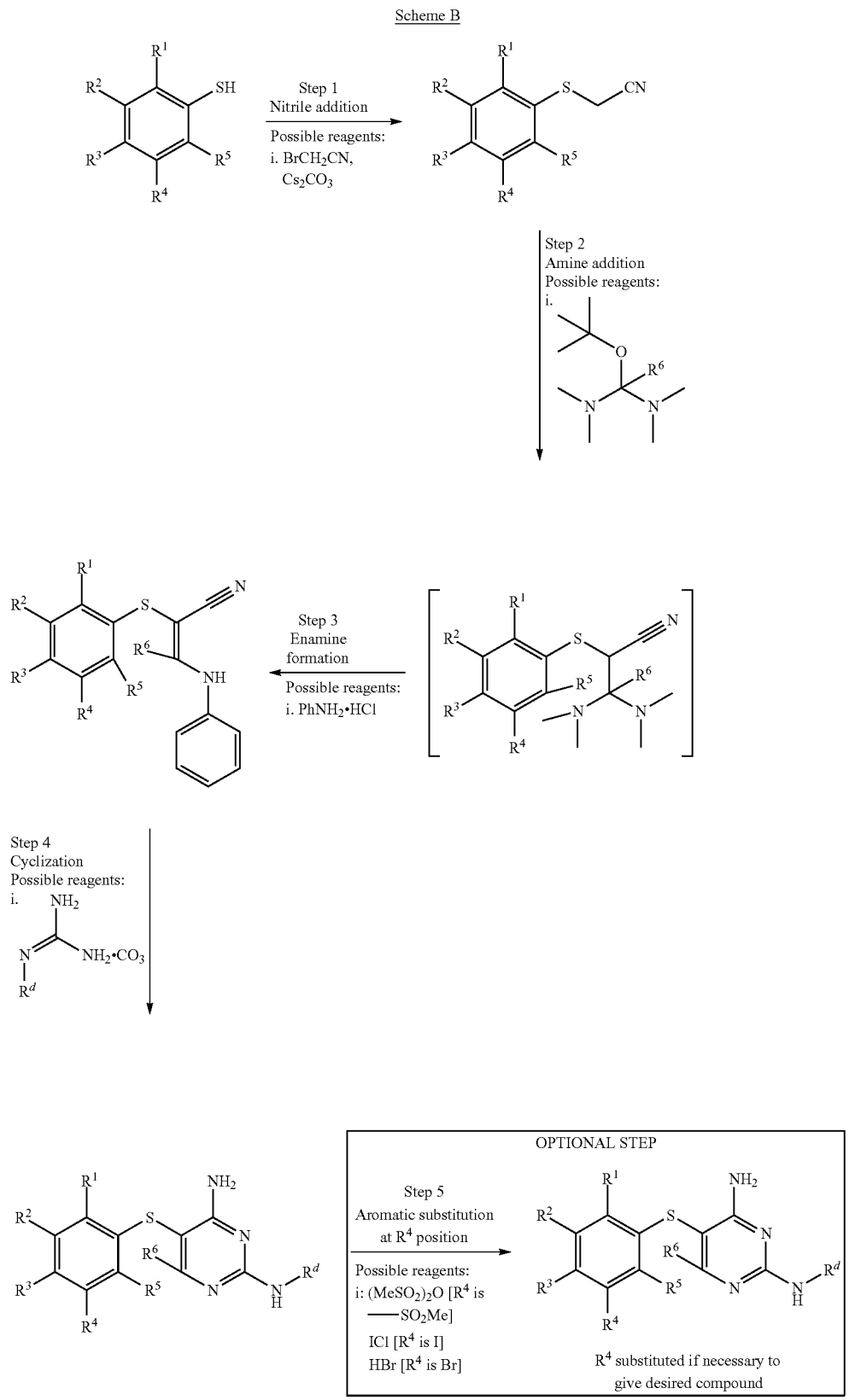

Generally speaking, Scheme B contemplates:

reaction of an optionally substituted thiophenol with BrCH$_2$CN and Cs$_2$CO$_3$;

amine addition to the resulting thioether;

enamine formation from the resulting amine; and cyclization of the resulting compound to produce a compound of Formula 1.

In Scheme B further additional, steps may be used to manipulate the substitution on the phenyl ring. For example, when R$^4$ is methyl or alkynyl, these compounds may be provided via the corresponding compound wherein R$^4$ is iodo e.g. by cross-coupling chemistry to exchange the iodo group for a methyl or alkynyl group.

Scheme C illustrates yet another synthetic procedure usable to prepare specific compounds of Formula (1):

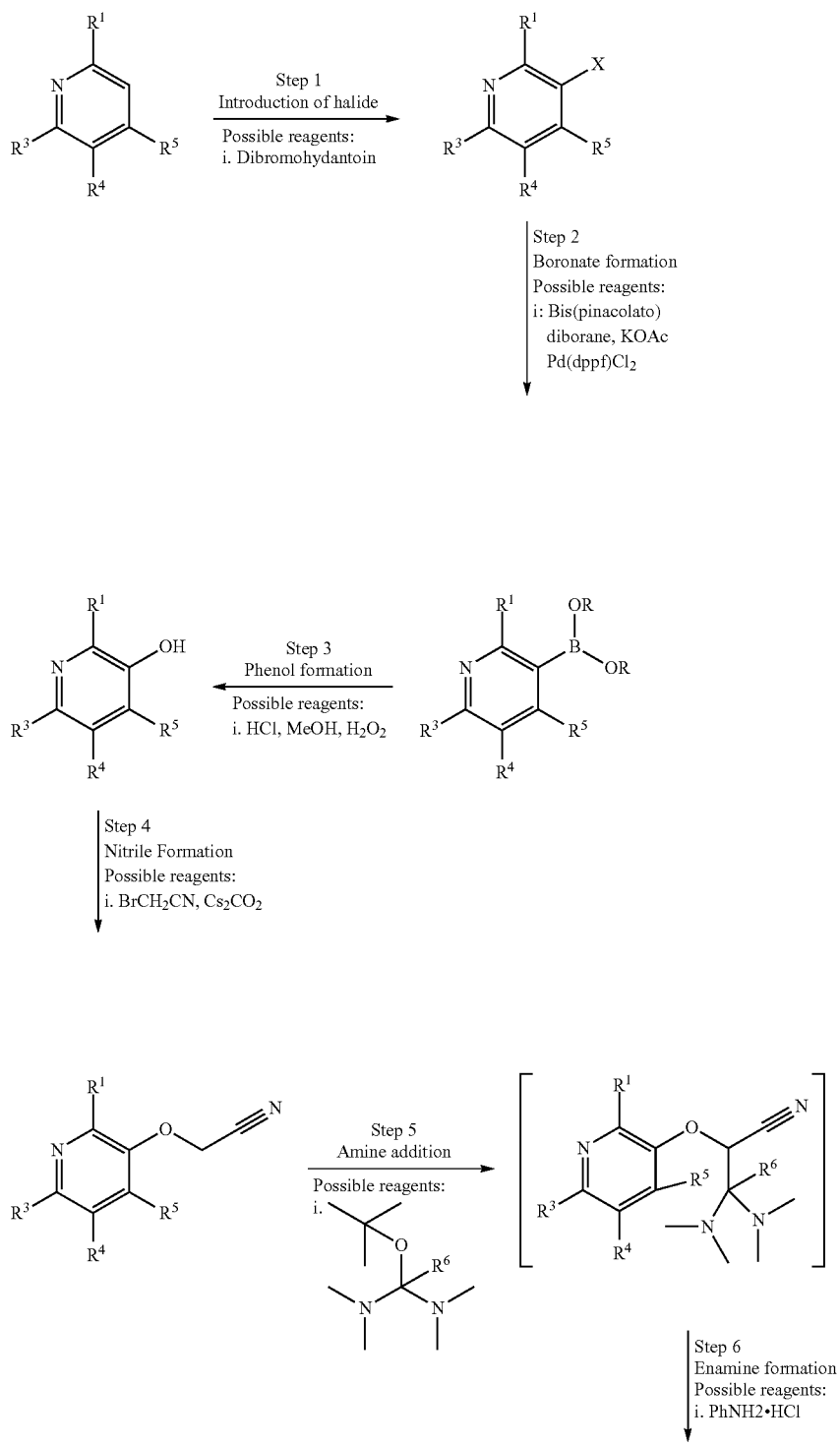

-continued

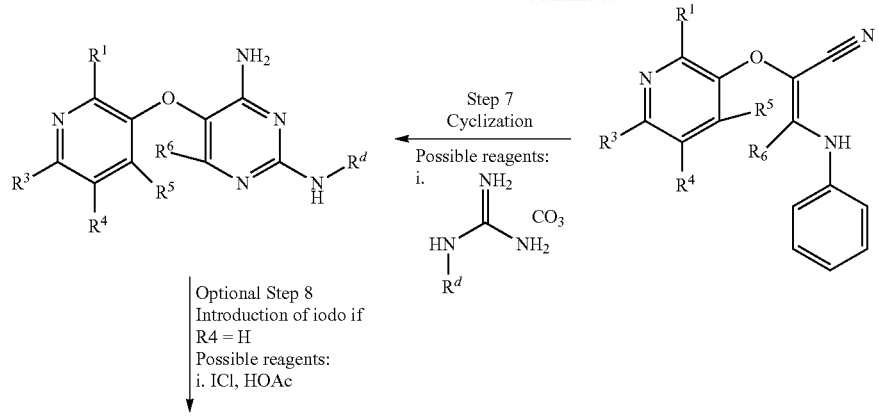

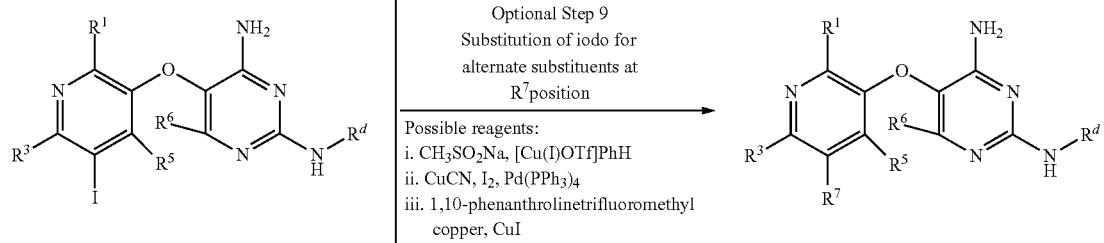

Generally speaking, Scheme C contemplates:
halogenation of an optionally substituted pyridine;
boronating the resulting halogenated pyridine;
converting the boronate to an hydroxy pyridine;
reaction of the hydroxy pyridine with $BrCH_2CN$ and $Cs_2CO_3$;

amine addition to the resulting nitrile ether;
enamine formation from the resulting amine; and
cyclization of the resulting compound to produce a compound of Formula 1.

Scheme D illustrates still another synthetic procedure usable to prepare specific compounds of Formula (1):

Scheme D

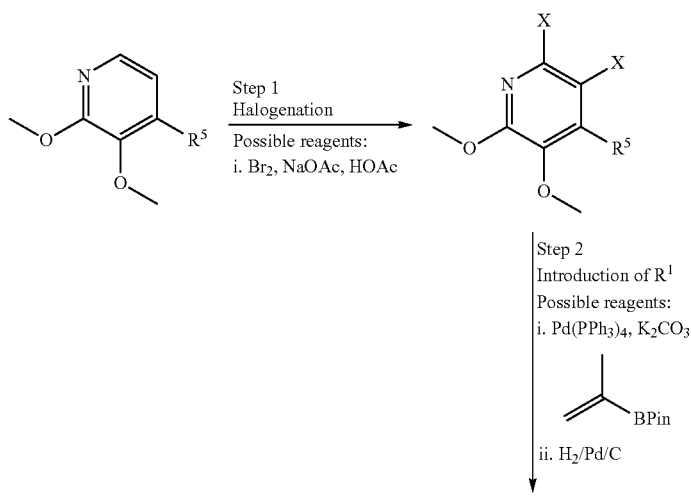

-continued
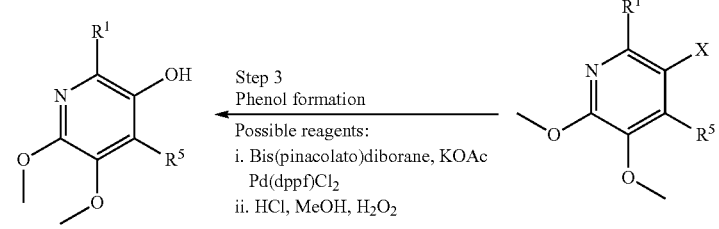
Step 3
Phenol formation
Possible reagents:
i. Bis(pinacolato)diborane, KOAc Pd(dppf)Cl₂
ii. HCl, MeOH, H₂O₂
Step 4
Nitrile Formation
Possible reagents:
i. BrCH₂CN, Cs₂CO₃
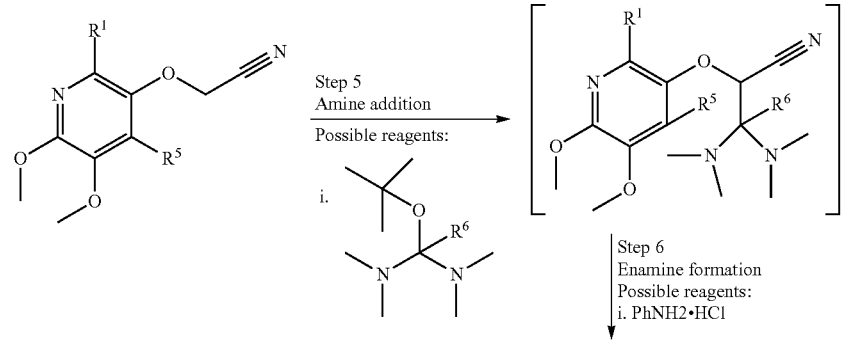
Step 5
Amine addition
Possible reagents:
i.
Step 6
Enamine formation
Possible reagents:
i. PhNH2•HCl
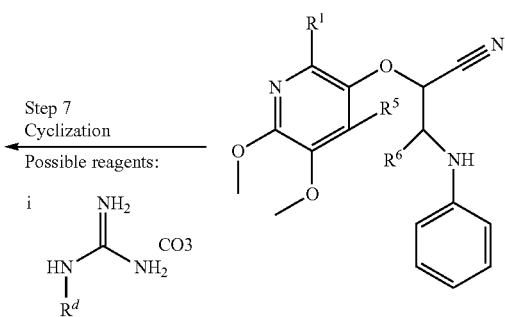
Step 7
Cyclization
Possible reagents:
i Generally speaking, Scheme D contemplates:

halogenation of a dimethoxypyridine;

introduction of $R^1$ into the halogenated dimethoxypyridine;

converting the resulting compound into an hydroxy pyridine;

reaction of the hydroxy pyridine with $BrCH_2CN$ and $Cs_2CO_3$;

amine addition to the resulting cyano ether;

enamine formation from the resulting amine; and cyclization of the resulting compound to produce a compound of Formula 1.

Scheme D is especially applicable to compounds wherein $R^4=OCH_3$. The first two steps are a variation on the general scheme set forth above.

Scheme 1 illustrates an exemplary synthetic procedure usable to prepare specific compounds of Formula 1n:

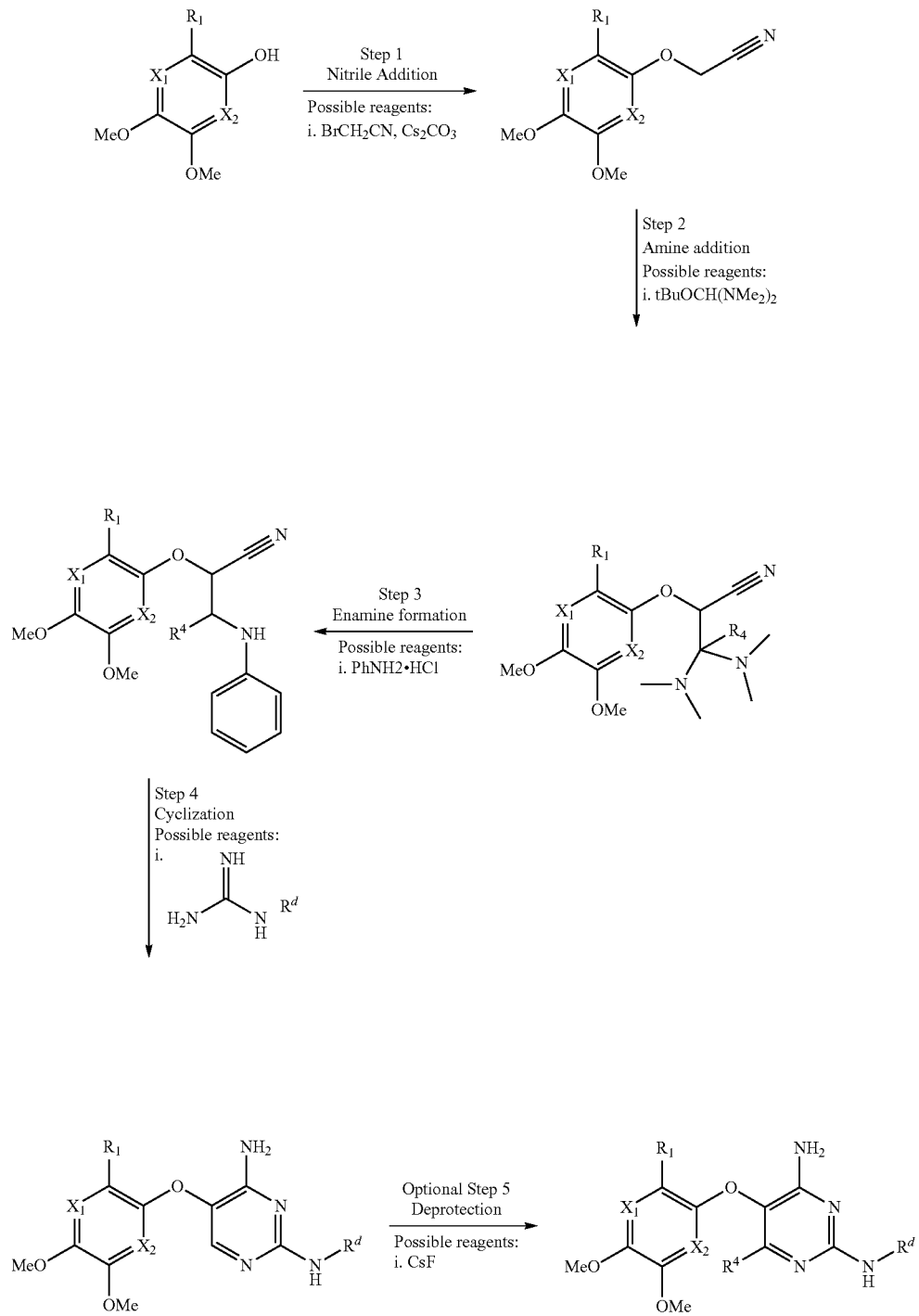

Generally speaking, Scheme 1 contemplates:

Reaction of a dimethoxyphenol with $BrCH_2CN$ and $Cs_2CO_3$;

amine addition to the resulting nitrile ether;

enamine formation from the resulting amine; and cyclization of the resulting compound to produce a compound of Formula 1.

In some cases an optional step is required to remove protecting groups to unmask $R^d$ Scheme 2 illustrates another synthetic procedure usable to prepare intermediate compounds useful in the synthesis of compounds of Formula 1n, specifically for use in Step 4 in Scheme 1:

Scheme 2

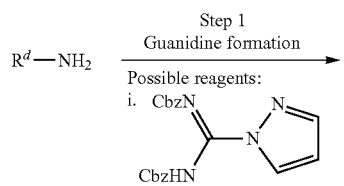

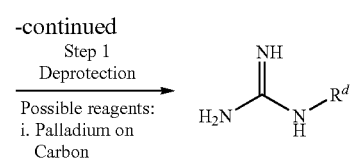

Generally speaking, Scheme 2 contemplates:

Reaction of an amine with a protected pyrazole guanidine reagent;

deprotection to give a guanidine suitable for use in Step 4 of Scheme 1.

Scheme 3 illustrates another synthetic procedure usable to prepare specific compounds of Formula 1n:

Scheme 3

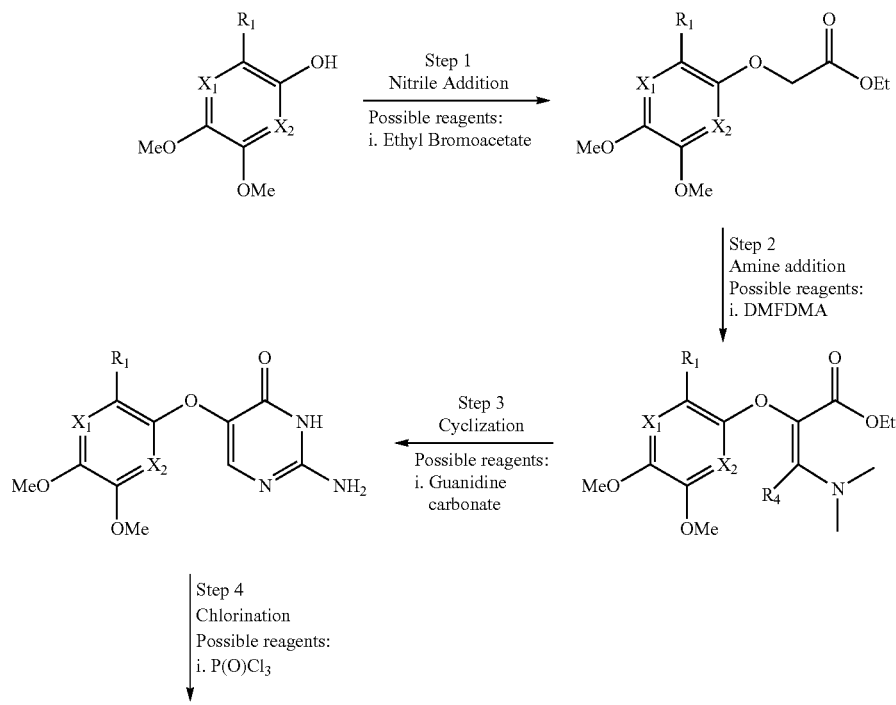

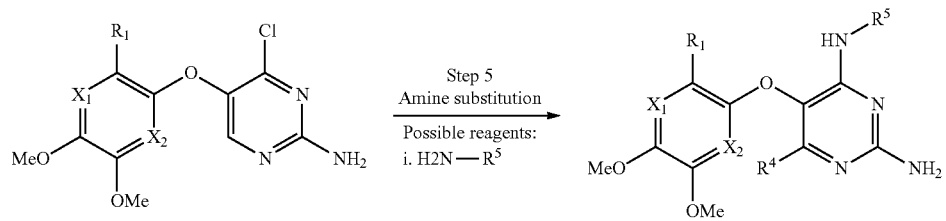

Generally speaking, Scheme 3 contemplates:

Reaction of a dimethoxyphenol with Ethyl bromoacetate and $Cs_2CO_3$;

enamine formation from the resulting amine;

cyclization of the resisting compound to give a pyrimidone;

chlorination to give a chloropyrimidine; and substitution of the chlorine to give a compound of Formula 1n.

The compounds of the present disclosure are usable for the treatment of a wide range of genitourinary diseases, conditions and disorders, including urinary tract disease slates associated with bladder outlet obstruction and urinary incontinence conditions such as reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urethritis, prostatitits, pelvic pain syndrome, prostatodynia, cystitis, and idiophatic bladder hypersensitivity, and other symptoms related to overactive bladder.

The compounds of the present disclosure are also useful for the treatment of cough or urge to cough associated with a respiratory disease, hypertension, heart failure, dyspnea, sleep apnea, altering carotid body tonicity or activity in a subject, and the like.

The compounds of the present disclosure are also expected to find utility as analgesics in the treatment of diseases and conditions associated with pain from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

The present disclosure includes pharmaceutical compositions comprising at least one compound of the present disclosure, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present disclosure will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present disclosure for a given disease.

Compounds of the present disclosure may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by in-halation or insufflation. The preferred manner of administration is generally oral using a convenient daily dosage regimen which can be adjusted according to the degree of affliction.

A compound or compounds of the present disclosure, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present disclosure may be formulated in a wide variety of oral administration dosage forms. The pharmaceutical compositions and dosage forms may comprise a compound or compounds of the present disclosure or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, e.g., in aqueous propylene glycol solutions or may contain emulsifying agents, e.g., such as lecithin, sorbitan monooleate, or acacia. Aqueous solutions can be prepared by dissolving the active component in water and adding suitable colorants, flavours, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Solid form preparations include solutions, suspensions, and emulsions, and may contain, in addition to the active component, colorants, flavours, stabilizers, buffers, artificial and natural sweeteners, dispersants, thickeners, solubilizing agents, and the like.

The compounds of the present disclosure may be formulated for parenteral administration (e.g., by injection, e.g. bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, e.g. solutions in aqueous polyethylene glycol.

Examples of oily or non-aqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present, disclosure may be formulated for topical administration to the epidermis as ointments, creams or lotions, or as a transdermal patch. Ointments and creams may, e.g., be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatine and glycerine or sucrose and acacia; and mouth-washes comprising the active ingredient in a suitable liquid carrier.

The compounds of the present disclosure may be formulated for administration as suppositories. A low melting wax, such as a mixture of fatty acid glycerides or cocoa butter is first melted and the active component is dispersed homogeneously, e.g., by stirring. The molten homogeneous mixture is then poured into convenient sized molds, allowed to cool, and to solidify.

The compounds of the present disclosure may be formulated for vaginal administration. Pessaries, tampons, creams, gels, pastes, foam or sprays containing in addition to the active ingredient such carriers as are known in the art to be appropriate.

The subject compounds may be formulated for nasal administration. The solutions or sus-pensions are applied directly to the nasal cavity by conventional means, e.g., with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved e.g. by means of a metering atomizing spray pump.

The compounds of the present disclosure may be formulated for aerosol administration, particularly to the respiratory tract and including intranasal administration. The compound will generally have a small particle size e.g. of the order of five (5) microns or less. Such a particle size may be obtained by means known in the art, e.g. by micronization. The active ingredient is provided in a pressurized pack with a suitable propellant such as a chlorofluoro-carbon (CFC), e.g., dichlorodifluoromethane, trichlorofluoromethane, or dichlorotetra-fluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, e.g. a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form e.g. in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present disclosure can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems are inserted sub-cutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by Martin, Mack Publishing Company, 19th edition, Easton, Pa. Representative pharmaceutical formulations containing a compound of the present disclosure are described herein.

EXAMPLES

The following preparations and examples are given to enable those skilled in the art to more clearly understand and to practice the present disclosure. They should not be considered as limiting the scope of the present disclosure, but merely as being illustrative and representative thereof.

Example 1

Synthesis of Compound 1

Compound 1 was made by the synthetic method outlined in Scheme E:

Scheme E

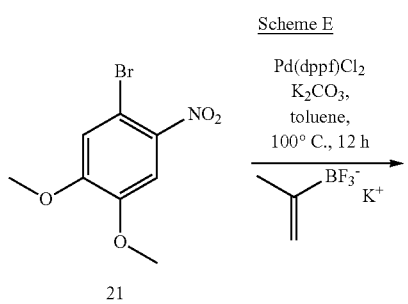

21

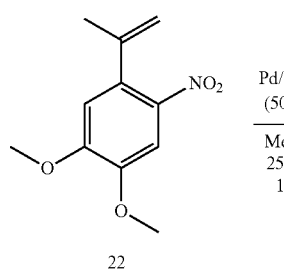

22

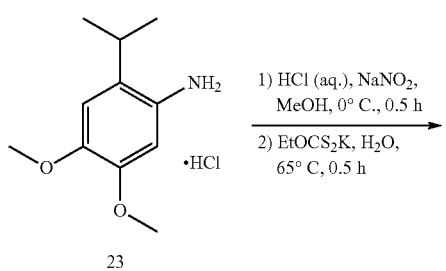

23

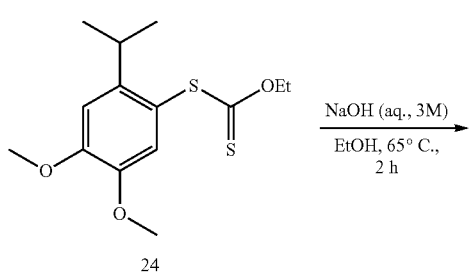

24

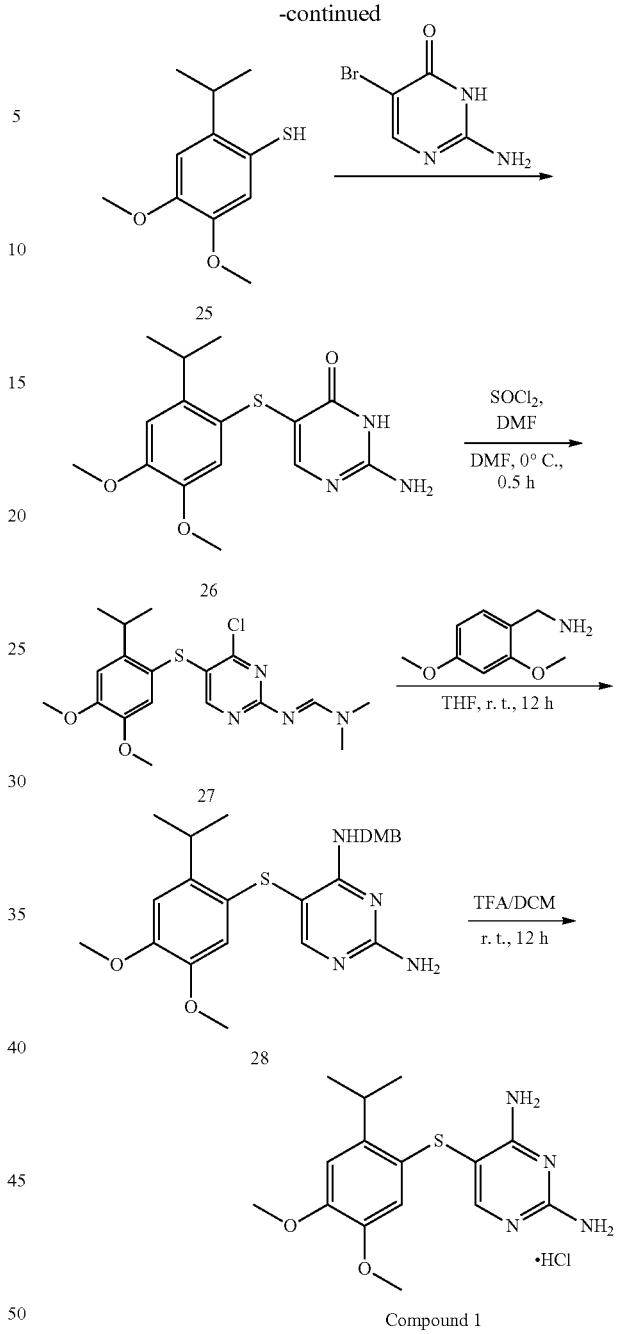

General Procedure for Preparation of Compound 22:

To a solution of Compound 21 (2.0 g, 7.6 mmol, 1.0 eq) and potassium difluoro(isopropenyl)borane fluoride (4.5 g, 30 mmol, 4.0 eq) in toluene was added $K_2CO_3$ (3.16 g, 22 mmol, 3.0 eq) and Pd(dppf)Cl$_2$ (558 mg, 763 μmol, 0.1 eq) at 25° C. under N$_2$. The mixture was heated to 100° C. and stirred for 12 hrs. The reaction mixture was directly concentrated under reduced pressure to give a residue. The residue was further purified by column chromatography eluted with petroleum ether: ethyl acetate to give Compound 22 (1.6 g, 6.4 mmol, 84% yield, 90% TLC purity) as white solid, which was used directly in the next step.

General Procedure for Preparation of Compound 23:

A mixture of Compound 22 (1.6 g, 7.1 mmol, 1.0 eq) in MeOH was hydrogenated under H$_2$ (50 psi) with catalyst Pd/C (100 mg) at 25° C. for 12 h. The mixture was filtered through celite, washed with methanol (200 mL). The filtrate was added concentrated HCl (1.0 mL), and then concentrated to give Compound 23 (1.4 g crude) as blue solid, which was used directly in the next step.

$^1$H NMR: (400 MHz MeOD-d$_4$) δ 7.00 (s, 1H), 6.92 (s, J=4.0 Hz, 1H), 3.88 (s, 3H), 3.86 (s, 3H), 3.08-3.02 (m, 1H), 1.31 (d, J=6.4 Hz, 6H).

General Procedure for Preparation of Compound 24:

To a solution of Compound 23 (1.3 g, 6.6 mmol, 1.0 eq) in MeOH (6.5 mL) and aq.HCl (1.0 M, 13 mL, 2.0 eq) was added dropwise a solution of NaNO$_2$ (716 mg, 10 mmol, 564 μL, 1.5 eq) in H$_2$O (13 mL) at 0° C., then the mixture was stirred for 0.5 h. After this time, the mixture was added to solution of ethoxycarbothioylsulfanylpotassium (2.1 g, 13 mmol, 2.0 eq) in H$_2$O (32 mL) at 65° C. Then mixture was stirred for 0.5 h at 65° C. The mixture was poured into water (150 mL). ELOAc (150 mL) was added and the organic layer was separated. The aqueous layer was extracted with EtOAc (150 mL). The extractions were combined, dried over anhydrous Na$_2$SO$_4$, and filtered. The filtrate was concentrated to give crude product, which was further purified by silica, gel column to give Compound 24 (800 mg, 36% yield) as colorless oil.

$^1$H NMR: (400 MHz CDCl$_3$) δ 6.95 (s, 1H), 6.86 (s, 1H), 4.61 (q, J=7.2 Hz, 2H), 3.94 (s, 3H), 3.86 (s, 3H), 3.41-3.83 (m, 1H), 1.35 (t, J=7.2 Hz, 3H), 1.20 (d, J=6.8 Hz, 6H).

General Procedure for Preparation of Compound 25:

To a solution of Compound 24 (700 mg, 23 mmol, 1.0 eq) in EtOH (8.0 mL) was added aq.NaOH (3 M, 8.5 mL, 11 eq) at 25° C. Then the mixture was heated to 65° C. and stirred for 2 hrs. The mixture was cooled to room temperature and 1,4-dithioerythritol (CAS: 6892-68-8, 20 mg) was added. The mixture was adjusted to pH=5 with 10% aq.HCl, then extracted with EtOAc (100 mL×2). The organic layer was dried over anhydrous Na$_2$SO$_4$, filtered. The filtrate was concentrated to give Compound 25 (500 mg, crude) as a colorless oil, which was directly used without further purification.

General Procedure for Preparation of Compound 26:

To a solution of Compound 25 (400 mg, 1.8 mmol, 1.0 eq) in DMF (5.0 mL) was added 2-amino-5-bromo-1H-pyrimidin-6-one (357 mg, 1.8 mmol, 1.0 eq) and K$_2$CO$_3$ (779 mg, 5.6 mmol, 3.0 eq) at 25° C. Then the mixture was heated to 80° C. in a sealed tube and stirred for 1 h under microwave. The mixture was filtered. The filter cake was washed with DMF (1 mL). The DMF solution was collected and combined and purified by prep-HPLC to give 26 (220 mg, 35% yield) as white solid.

$^1$H NMR: (400 MHz DMSO-d$_6$) δ 11.16 (br. s. 1H), 7.66 (s, 1H), 6.84-6.77 (m, 4H), 3.76 (s, 3H), 3.64 (s, 3H), 3.53-3.33 (m, 1H), 1.18 (d, 6.8 Hz, 6H).

LCMS: [M+H] 321.1.

General Procedure for Preparation of Compound 27:

To a solution of DMF (143 mg, 1.9 mmol, 151 μL, 4.8 eq) was added dropwise SOCl$_2$ (246 mg, 2.0 mmol, 150 μL, 5.1 eq) with cooling bath at 0° C. The resulting mixture was added to a solution of 26 (130 mg, 404 μmol, 1.0 eq) in DMF (3.0 mL) at 0° C. The mixture was stirred for 0.5 h at 0° C. The reaction was concentrated to give Compound 27 (160 mg, crude) as a colorless oil, which was directly used without further purification.

LCMS: [M+H] 395.2.

General Procedure for Preparation of Compound 28:

To a solution of Compound 27 (160 mg, 405 μmol, 1.0 eq) in THF (4.0 mL) was added 2,4-DMBNH$_2$ (2,4-Dimethoxybenzylamine, 3.4 g, 20 mmol, 50 eq) at 25° C. The resulting mixture was stirred for 12 hrs at 25° C. The mixture was diluted with brine (50 mL), and then extracted with EtOAc (100 mL). The organic layer was dried over anhydrous Na$_2$SO$_4$, filtered, and the filtrate was concentrated to give crude product, which was further purified by prep-HPLC to give Compound 28 (120 mg, 85% LCMS purity) as colorless oil, which was used directly in the next step.

LCMS: [M+H] 471.2.

General Procedure for Preparation of Compound 1:

To a solution of Compound 28 (120 mg, 255 μmol, 1.0 eq) in DCM (4.0 mL) was added TFA (6.1 g. 54 mmol, 4.0 mL, 211 eq) at 25° C., the mixture was stirred for 12 hrs at 25° C. The mixture was concentrated to give crude product, which was purified by prep-HPLC to give 1 (15 mg, 100% LCMS purity, 13% yield) as a white solid.

$^1$H NMR: (400 MHz MeOD-d$_4$) 7.78 (s, 1H), 6.95 (s, 1H), 6.88 (s, 1H), 3.86 (s, 3H), 3.78 (s, 3H), 3.61-3.53 (m, 1H), 1.26 (d, J=6.8 Hz, 6H).

LCMS: [M+H]$^+$ 321.2.

Example 2

Synthesis of Compound 2

Compound 2 was made by the synthetic method outlined in Scheme F:

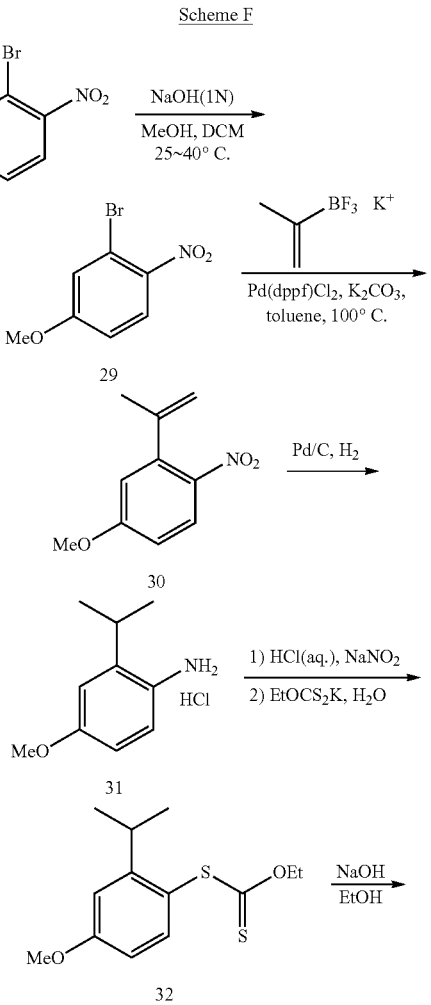

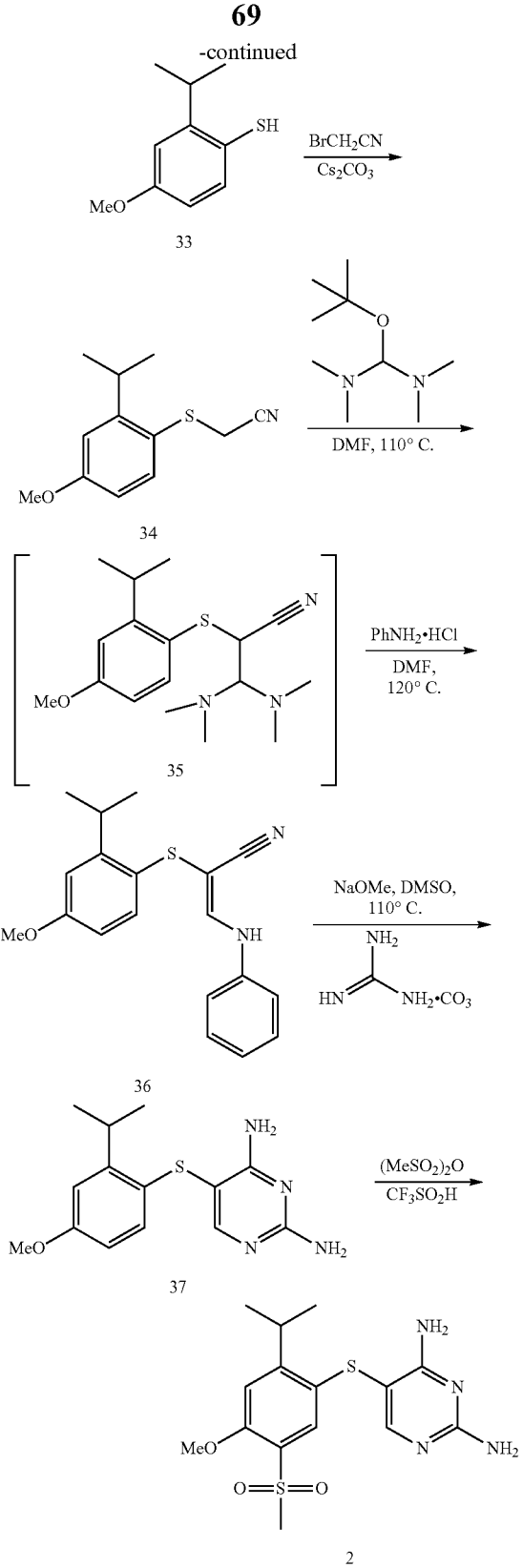

General Procedure for Preparation of Compound 29:

To a solution of 2-bromo-4-fluoro-1-nitro-benzene (60.0 g, 273 mmol, 1.00 eq) in the mixture of dichloromethane (400 mL) and methanol (440 mL) was added 1 M NaOH aqueous solution (1.00 L). Then a catalytic amount of TBAB (tetrabutylammonium bromide, 360 mg, 1.26 mmol) was added. The reaction was stirred at 40° C. for 16 h. The reaction mixture was partitioned between DCM and water. Then the aqueous layer was extracted with dichloromethane (3×300 mL). The combined organic layers were dried over $Na_2SO_4$, filtered and concentrated under reduced pressure. The crude product was purified by column chromatography on silica gel to give Compound 29 (43.1 g, 186 mmol, 68% yield) as a yellow solid.

$^1$H NMR: (400 MHz, Chloroform-d) 8.00 (d, J=9.3 Hz, 1H), 7.23 (d, J=2.6 Hz, 1H), 6.93 (dd, J=2.6, 9.3 Hz, 1H), 3.90 (s, 3H).

General Procedure for Preparation of Compound 30:

Two parallel reactions were set up as follows and subsequently combined for extraction and purification.

To a solution of 29 (40.0 g, 172 mmol, 1.00 eq) and potassium difluoro(isopropenyl)borane fluoride (51.0 g, 344 mmol, 2.00 eq) in toluene (200 mL) was added $Pd(dppf)Cl_2$ (12.6 g, 17.2 mmol, 0.10 eq) and $K_2CO_3$ (71.5 g, 517 mmol, 3.00 eq). The reaction mixture was stirred at 100° C. for 12 h under $N_2$ atmosphere.

The two reaction mixtures were combined and were partitioned between ethyl acetate (200 mL) and water (200 mL). The aqueous layer was extracted with ethyl acetate (3×200 mL). Then the combined organic layers were dried over $Na_2SO_4$, filtered and concentrated under reduced pressure. The residue was purified by column chromatography on silica gel to give Compound 30 (45.0 g, 233 mmol, 67% yield) as a brown oil.

$^1$H NMR: (400 MHz, Chloroform-d) 8.01 (d, J=8.8 Hz, 1H), 6.86 (dd, J=2.9, 9.0 Hz, 1H), 6.76 (d, J=2.6 Hz, 1H), 5.17-5.14 (m, 1H), 4.93 (s, 1H), 3.90 (s, 3H), 2.08 (s, 3H).

General Procedure for Preparation of Compound 31:

To a solution of 30 (45.0 g, 233 mmol, 1.00 eq) in methanol (800 mL) was added Pd/C (4.18 g, 1.97 mmol, 5% w.t.). The mixture was stirred at 25° C. under $H_2$ (50 psi) for 12 h. The reaction mixture was filtered through celite and washed with methanol (300 mL). To the filtrate was added 12M HCl (40.0 mL). Then the mixture was concentrated to give Compound 31 (53.7 g, crude, HCl) as a purple solid which was used for the next step directly.

$^1$H NMR: (400 MHz, DMSO-$d_6$) 10.16 (br. s., 3H), 7.38-7.32 (m, 1H), 6.91 (d, J=2.6 Hz, 1H), 6.86-6.80 (m, 1H), 3.73 (s, 3H), 3.08 (td, J=6.7, 13.6 Hz, 1H), 1.16 (d, J=7.1 Hz, 6H).

General Procedure for Preparation of Compound 32:

Two parallel reactions were set up as follows and subsequently combined for extraction and purification.

To a solution of 31 (19.4 g, 95.9 mmol, 1.00 eq) in methanol (70.0 mL) and HCl (1 M, 193 mL, 56.4 eq) was added dropwise a solution of $NaNO_2$ (7.94 g, 115 mmol, 6.25 mL, 1.20 eq) in $H_2O$ (80.0 mL) at 0° C. The mixture was stirred at 0° C. for 0.5 h. Then the mixture was added dropwise to a solution of $EtOCS_2K$ (30.7 g, 192 mmol, 2.00 eq) in $H_2O$ (500 mL) at 25° C. The mixture was stirred at 25° C. for 0.5 h. The two reaction mixtures were combined and partitioned between ethyl acetate (500 mL) and water (500 mL). The aqueous layer was extracted with ethyl acetate (3×300 mL). The combined organic layers were dried over $Na_2SO_4$, filtered and concentrated under reduced pressure. The residue was purified by column chromatography on silica gel to give Compound 32 (22.0 g, 81.4 mmol, 84% yield) as a brown oil which was used for the next step directly.

$^1$H NMR: (400 MHz, Chloroform-d) 7.43-7.38 (m, 1H), 6.93 (d, J=2.6 Hz, 1H), 6.28 (dd, J=2.6, 8.4 Hz, 1H), 4.61 (q, J=7.1 Hz, 2H), 3.86 (s, 3H), 3.38 (td, J=6.8, 13.7 Hz, 1H), 1.34 (t, J=7.1 Hz, 3H), 1.21 (d, J=7.1 Hz, 6H).

General Procedure for Preparation of Compound 33:

To a solution of 32 (22.0 g, 81.4 mmol, 1.00 eq) in EtOH (200.00 mL) was added NaOH (3 M, 298 mL, 11.0 eq). Then the mixture was stirred at 65° C. for 2 h. 1,4-dithioerythritol (200 mg) was added. The mixture was adjusted to pH=5 with 3M HCl (290 mL). Then the mixture was partitioned between ethyl acetate (300 mL) and water (300 mL). The aqueous layer was extracted with ethyl acetate (3×300 mL). The combined organic layers were dried over $Na_2SO_4$, filtered and concentrated under reduced pressure to give Compound 33 (13.3 g, crude) as a brown oil which was used for the next step directly.

$^1$H NMR: (400 MHz, DMSO-$d_6$) 7.27 (d, J=8.4 Hz, 1H), 6.78 (d, J=2.2 Hz, 1H), 6.70-6.65 (m, 1H), 4.80 (s, 1H), 3.69 (s, 3H), 3.11 (td, J=6.9, 13.5 Hz, 1H), 1.15 (d, J=6.6 Hz, 6H).

General Procedure for Preparation of Compound 34:

To a solution of 33 (13.3 g, 72.9 mmol, 1.00 eq) in $CH_3CN$ (100 mL) was added $BrCH_2CN$ (13.1 g 109 mmol 1.50 eq) and $Cs_2CO_3$ (35.6 g, 109 mmol, 1.50 eq). The mixture was stirred at 80° C. for 12 h. The reaction mixture was partitioned between ethyl acetate (100 mL) and water (100 mL). The aqueous layer was extracted with ethyl acetate (3×80 mL). The combined organic layers were dried over $Na_2SO_4$, filtered and concentrated under reduced pressure. The residue was purified by column chromatography on silica gel to give Compound 34 (10.6 g, 47.9 mmol, 65% yield) as a brown oil.

$^1$H NMR: (400 MHz, DMSO-$d_6$) 7.54 (d, J=8.8 Hz, 1H), 6.91 (d, J=3.1 Hz, 1H), 6.86 (dd, J=2.9, 8.6 Hz, 1H), 3.96 (s, 2H), 3.78 (s, 3H), 3.50 (td, J=7,0, 13.8 Hz, 1H), 1.19 (d, J=6.6 Hz, 6H).

General Procedure for Preparation of Compound 35:

To a solution of 34 (10.6 g, 47.9 mmol, 1.00 eq) in DMF (80.0 mL) was added 1-tert-butoxy-N,N,N',N'-tetramethylmethanediamine (16.7 g, 95.8 mmol, 19.9 mL, 2.00 eq). Then the mixture was stirred at 110° C. for 1 h. The reaction mixture was used directly in the next step.

General Procedure for Preparation of Compound 36:

To a solution of 35 (15.4 g, 47.9 mmol, 1.00 eq) in DMF (150 mL) was added aniline hydrochloride (31.0 g, 240 mmol, 30.4 mL, 5.00 eq). The mixture was stirred at 120° C. for 12 h. The reaction mixture was partitioned between toluene (100 mL) and water (100 mL). Then the aqueous layer was extracted with toluene (3×80 mL). The combined organic layers were dried over $Na_2SO_4$, filtered and concentrated under reduced pressure to give Compound 36 (32.3 g, crude) as brown oil which was used for the next step directly.

$^1$H NMR: (400 MHz, Chloroform-d) 7.34 (dt, J=3.5, 7.1 Hz, 5H), 7.15 (d, 7.9 Hz, 3H), 6.98 (d, J=7.9 Hz, 2H), 6.71 (s, 1H), 3.80 (s, 3H), 3.49 (d, J=6.6 Hz, 1H), 1.29 (d, J=7.1 Hz, 6H).

General Procedure for Preparation of Compound 37:

To a solution of 36 (32.3 g, 100 mmol, 1.00 eq) in DMSO (300 mL) was added $CH_3ONa$ (16.1 g, 299 mmol, 3.00 eq) and guanidine carbonate (26.9 g, 149 mmol, 1.50 eq). The mixture was stirred at 110° C. for 12 h. The reaction mixture was partitioned between ethyl acetate (200 mL) and water (200 mL). Then the aqueous layer was extracted with ethyl acetate (3×100 mL). The combined organic layer was dried over $Na_2SO_4$, filtered and concentrated under reduced pressure. The residue was purified by column chromatography on silica gel and prep-HPLC to give Compound 37 (4.00 g, 13.8 mmol, 13% yield) as a yellow solid which was used for the next step directly.

$^1$H NMR: (400 MHz, DMSO-$d_6$) 7.82 (s, 1H), 6.79 (d, J=2.6 Hz, 1H), 6.73 (s, 1H), 6.69-6.66 (m, 1H), 6.31 (br. s., 2H), 3.66 (s, 3H), 3.40-3.35 (m, 1H), 1.17 (d, J 6.6 Hz, 6H).

LCMS: [M+H]$^+$ 291.1

General Procedure for Preparation of Compound 2:

To a mixture of 37 (200 mg, 689 µmol, 1.00 eq) and methylsulfonyl methanesulfonate (480 mg, 2.76 mmol, 4.00 eq) was added $CF_3SO_3H$ (310. mg, 2.07 mmol, 182 µL, 3.00 eq). Then the mixture was stirred at 80° C. for 12 h. The mixture was adjusted to pH=8 with sat. $NaHCO_3$ (10 mL). The mixture was partitioned between ethyl acetate (30 mL) and water (30 mL). Then the aqueous layer was extracted with ethyl acetate (3×30 mL). The combined organic layers were dried over $Na_2SO_4$, filtered and concentrated under reduced pressure. The residue was purified by prep-HPLC to give Compound 2 (46.0 mg, 125 µmol, 18% yield) as a white solid.

$^1$H NMR: (400 MHz, DMSO-$d_6$) 7.84 (s, 1H), 7.19 (s, 1H), 7.12 (s, 1H), 6.36 (br. s., 2H), 3.91 (s, 3H), 3.46-3.39 (m, 1H), 3.13 (s, 3H), 1.26 (d, J=6.6 Hz, 6H).

LCMS: [M+H]$^+$ 369.0.

Example 3

Synthesis of Compound 3

Compound 3 was made by the synthetic method outlined in Scheme G:

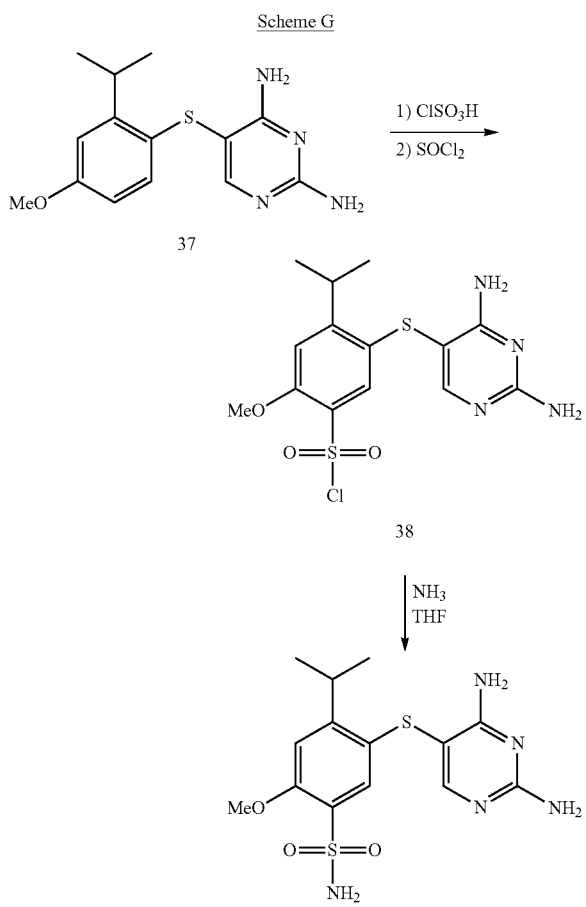

Compound 37 was prepared as outlined above in Example 2.

General Procedure for Preparation of Compound 38:

A mixture of 37 (200 mg, 689 μmol; 1.00 eq) and sulfurochloridic acid (802 mg, 6.89 mmol, 458 μL, 10.0 eq) was stirred at 20° C. for 2.5 h. Then SOCl$_2$ (164 mg, 1.38 mmol, 99.9 μL, 2.00 eq) was added. The mixture was stirred at 20° C. for 1 h. The mixture was used for the next step directly without work up and purification.

General Procedure for Preparation of Compound 3:

Compound 38 was added to a cooled solution of NH$_3$ (10 μmol/L, 1.38 mL, 20.0 eq) in THF (1.38 mL) slowly at 0° C. The reaction mixture was stirred at 20° C. for 12 h. The mixture was filtered and washed with CH$_3$OH (30 mL). The filtrate was concentrated and the residue was purified by prep-HPLC to give 3 (37.0 mg, 100 μmol, 14% yield) as a white solid.

$^1$H NMR: (400 MHz, DMSO-d$_6$) 7.87 (s, 1H), 7.22 (s, 1H), 7.06 (s, 1H), 6.96 (s, 2H), 6.41 (br. s., 2H), 3.89 (s, 3H), 3.45 (td, J=6.7, 13.6 Hz, 1H), 2.07 (s, 2H), 1.27 (d, J=7.1 Hz, 6H).

LCMS: [M+H]$^+$ 370.0.

Example 4

Synthesis of Compound 4

Compound 4 was made by the synthetic method outlined in Scheme H

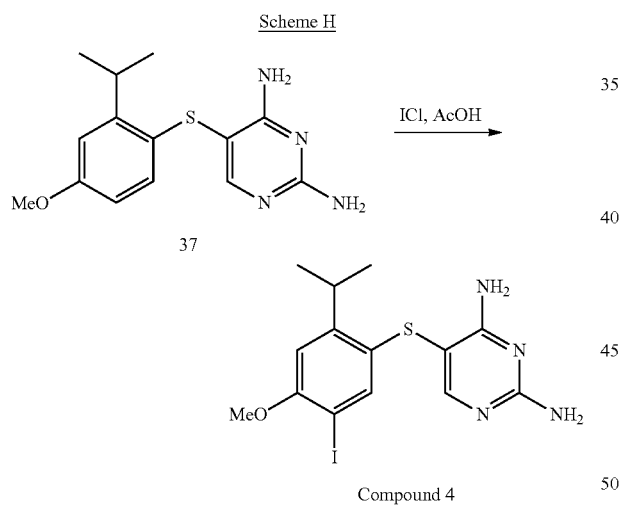

Compound 37 was prepared as outlined above in Example 2.

General Procedure for Preparation of Compound 4:

To a solution of 37 (1.50 g, 5.17 mmol, 1.00 eq) in HOAc (15.00 mL) was added ICl (1.01 g, 6.20 mmol, 316 μL, 1.20 eq) and H$_2$O (93.1 mg, 5.17 mmol, 1.80 mL, 1.00 eq). The mixture was stirred at 25° C. for 12 h. Then ICl (1.01 g, 6.20 mmol, 316 μL, 1.20 eq) was added and the mixture was stirred at 40° C. for 12 h. Another portion of ICl (1.01 g, 6.20 mmol, 316 μL, 1.20 eq) was added. The mixture was stirred at 40° C. for another 12 h. The mixture was adjusted to pH=7 with sat. NaHCO$_3$ (40 mL). Then the mixture was partitioned between ethyl acetate (50 mL) and water (50 mL). The aqueous layer was extracted with ethyl acetate (3×30 mL). The combined organic layers were dried over Na$_2$SO$_4$, filtered and concentrated. The residue was purified by column chromatography on silica gel to give 4 (1.00 g, 2.40 mmol, 46% yield).

100 mg of the solid was further purified by SFC separation to give 25 mg 4 as a white solid.

$^1$H NMR: (400 MHz, DMSO-d$_6$) 7.89 (s, 1H), 7.13 (s, 1H), 6.88 (s, 1H), 6.53 (br. s., 2H), 3.81 (s, 3H), 3.44-3.36 (m, 1H), 1.24 (d, J=6.6 Hz, 6H).

LCMS: [M+H]$^+$ 417.0.

Example 5

Synthesis of Compound 5

Compound 5 was made by the synthetic method outlined in Scheme I:

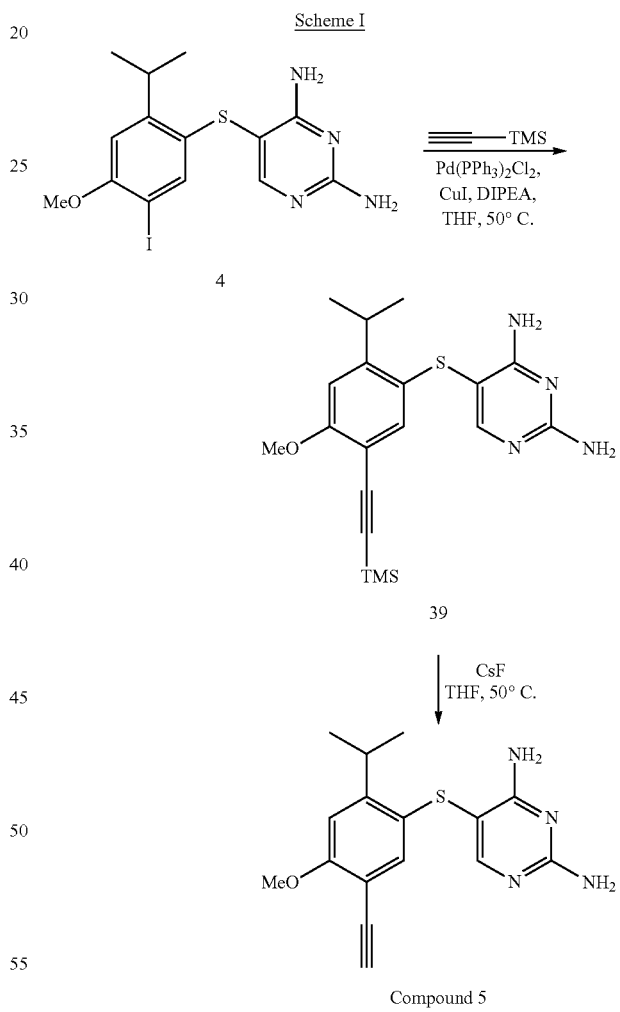

Compound 4 was prepared as outlined above in Example 4.

General Procedure for Preparation of Compound 39:

To a solution of 4 (300 mg, 721 μmol, 1.00 eq) in THF (3.00 mL) was added Pd(PPh$_3$)$_2$Cl$_2$ (202 mg, 288 μmol, 0.400 eq) and CuI (27.4 mg, 144 μmol, 0.200 eq) under N$_2$. Then ethynyl(trimethyl)silane (177 mg, 1.80 mmol, 2.50 eq) and diisopropylethylamine (745 mg, 5.77 mmol, 8.00 eq) was added. The mixture was heated to 50° C. for 12 hours under N₂. The reaction mixture was poured into aq. NH₄Cl (15% w.t., 3 mL) and extracted with ethyl acetate (4×6 mL). The combined organic layers were concentrated under reduced pressure to give brown oil. The residue was purified by prep-TLC to give 39 (110 mg, 284 μmol, 39% yield) as a light yellow solid.

¹H NMR: (400 MHz, Methanol-d₄) 7.92-7.90 (m, 1H), 6.91-6.87 (m, 2H), 3.85 (s, 3H), 3.56-3.49 (m, 1H), 1.31-1.26 (m, 6H), 0.19 (s, 9H).

General Procedure for Preparation of Compound 5:

To a mixture of 39 (95.0 mg, 246 μmol, 1.00 eq) in THF (2.00 mL) was added CsF (373 mg, 2.46 mmol, 90.6 μL, 10.0 eq) in one portion. The mixture was stirred at 50° C. for 2 h under N₂. The mixture was poured into H₂O (5 mL). The aqueous phase was extracted with ethyl acetate (4×10 mL). The combined organic phase was washed with brine (10 mL), dried over anhydrous Na₂SO₄, filtered and concentrated in vacuum to give a light yellow solid. The residue was purified by prep-HPLC to give 5 (15.0 mg, 47.7 μmol, 19% yield) as a white solid.

¹H NMR: (400 MHz, DMSO-d₆) 7.87 (s, 1H), 6.93 (s, 1H), 6.75 (s, 1H), 6.43 (br. s., 2H), 4.13 (s, 1H), 3.81 (s, 3H), 3.41 (td, J=6.8, 13.7 Hz, 1H), 1.24 (d, J=6.6 Hz, 6H).

LCMS: [M+H]⁺ 315.0.

Example 6

Synthesis of Compound 6

Compound 6 was made by the synthetic method outlined in Scheme J

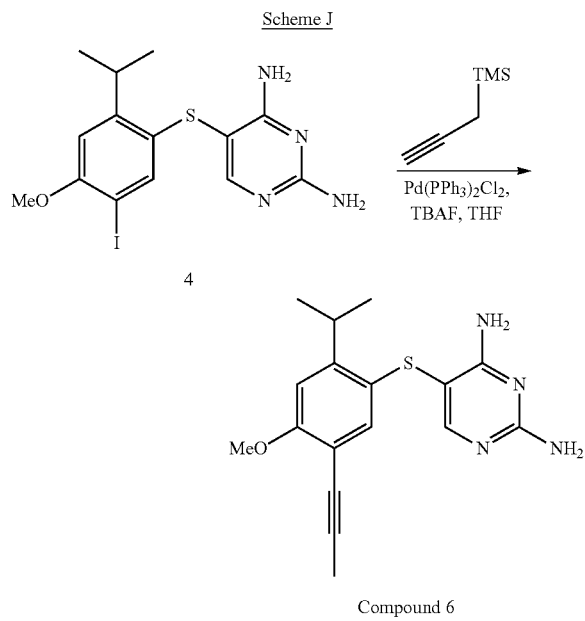

Starting material Compound 4 was prepared as outlined above in Example 4.

General Procedure for Preparation of Compound 6:

To a mixture of 4 (200 mg, 480 μmol, 1.00 eq) in THF (4.00 mL) was added trimethyl(prop-2-ynyl)silane (135 mg, 1.20 mmol, 179 μL, 2.50 eq), Pd(PPh₃)₂Cl₂ (169 mg, 240 μmol, 0.5 eq) and tetrabutyl ammonium fluoride (1 μmol/L, 1.44 mL, 3.00 eq). The mixture was de-gassed and then heated to 50° C. for 12 h under N₂. The residue was poured into H₂O (5 mL). The aqueous phase was extracted with ethyl acetate (3×8 mL). The combined organic phase was washed with brine (10 mL), dried over anhydrous Na₂SO₄, filtered and concentrated in vacuum to give a light yellow solid. The solid was purified by prep-HPLC to give 6 (16.0 mg, 48.7 μmol, 10% yield) as a light yellow solid.

¹H NMR: (400 MHz, DMSO-d₆) 7.86 (s, 1H), 6.88 (s, 1H), 6.66 (s, 1H), 6.42 (br. s., 2H), 3.78 (s, 3H), 3.43-3.36 (m, 1H), 1.99 (s, 3H), 1.24 (d, J=7.1 Hz, 6H).

LCMS: [M+H]+329.1.

Example 7

Synthesis of Compound 7

Compound 7 was made by the synthetic method outlined in Scheme K.

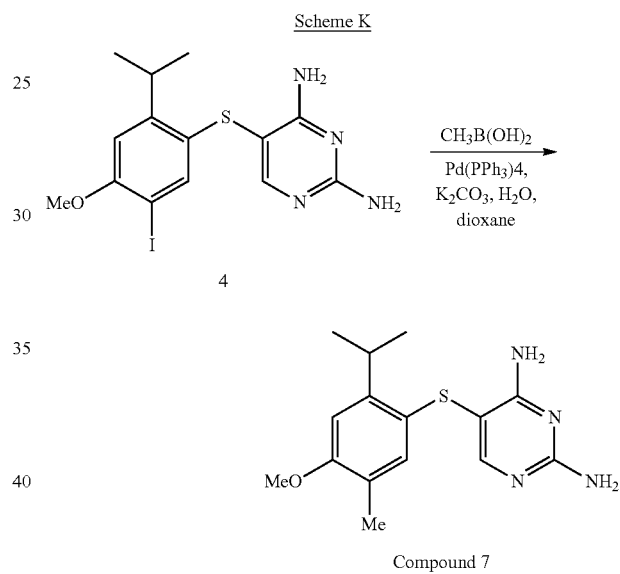

Compound 4 was prepared as outlined above in Example 4.

General Procedure for Preparation of Compound 7:

To a solution of 4 (200 mg, 480 μmol, 1.00 eq) in dioxane (14.0 mL)/H₂O (2.00 mL) was added methylboronic acid (152 mg, 2.55 mmol, 5.30 eq), K₂CO₃ (265 mg, 1.92 mmol, 4.00 eq) and Pd(PPh₃)₄ (55.5 mg, 48.0 μmol, 0.100 eq). The mixture was de-gassed and then heated to 100° C. for 12 h under N₂. The mixture was cooled to room temperature and then poured into water (10 mL). The aqueous phase was extracted with ethyl acetate (4×20 mL). The combined organic phase was dried over anhydrous Na₂SO₄, filtered and concentrated in vacuum to give crude product 7 as light yellow solid. The residue was purified by prep-HPLC and further purified by SFC separation to give 7 (26.0 mg, 85.4 μmol, 18% yield) as a white solid.

¹H NMR: (400 MHz, DMSO-d₆) 7.85 (s, 1H), 6.81 (s, 1H), 6.68 (s, 1H), 6.34 (br. s., 2H), 3.76 (s, 3H), 3.46 (quin, J=6.7 Hz, 1H), 2.00 (s, 3H), 1.21 (d, J=6.8 Hz, 6H).

LCMS: [M+H]⁺ 305.0.

Example 8

Synthesis of Compound 8

Compound 8 was made by the synthetic method outlined in Scheme L:

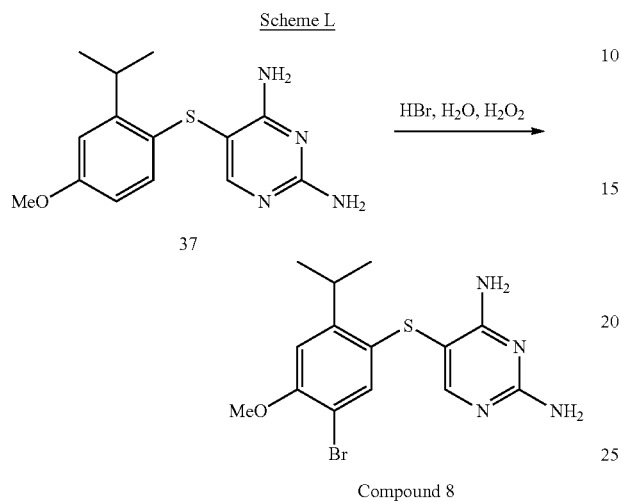

Scheme L

Starting material Compound 37 was prepared as outlined above in Example 2.

General Procedure for Preparation of Compound 8:

To a solution of 37 (200 mg, 689 µmol, 1.00 eq) in aqueous HBr (697 mg, 40% w.t., 5.00 eq) was added aqueous $H_2O_2$ (156 mg, 1.38 mmol, 30% w.t., 2.00 eq). Then the mixture was stirred at 25° C. for 12 h. Another portion of aqueous HBr (111 mg, 1.38 mmol, 74.8 µL, 2.00 eq) and aqueous $H_2O_2$ (46.9 mg, 1.38 mmol, 39.7 µL, 2.00 eq) was added. Then the mixture was stirred at 25° C. for 12 h. $H_2O$ (5 mL) and sat. $NaHSO_4$ (5 mL) were added and the mixture was partitioned between ethyl acetate (10 mL) and water (10 mL). Then the aqueous layer was extracted with ethyl acetate (3×10 mL). The combined organic layers were dried over $Na_2SO_4$, filtered and concentrated under reduced pressure. The residue was purified by prep-HPLC to give 8 (18.0 mg, 48.7 µmol, 7% yield) as a white solid.

$^1$H NMR: (400 MHz, Methanol-$d_4$) 7.90 (s, 1H), 6.99 (s, 1H), 6.92 (s, 1H), 3.84 (s, 3H), 3.51-3.46 (m, 1H), 1.28 (d, J=6.6 Hz, 6H).

LCMS: $[M+H]^+$ 368.9.

Example 9

Synthesis of Compound 9

Compound 9 was made by the synthetic method outlined in Scheme M:

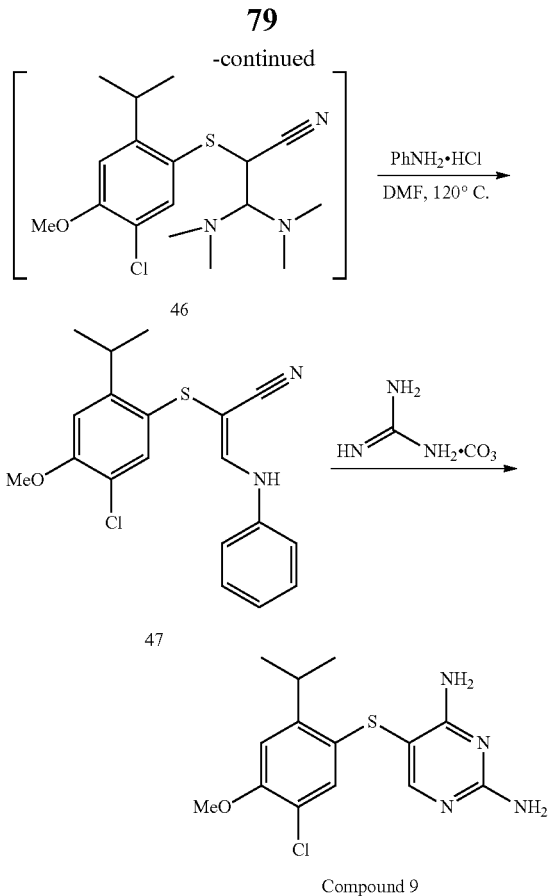

Compound 31 was prepared according to the procedure outlined in Example 2.

General Procedure for Preparation of Compound 40:

A solution of 31 (3.00 g, 14.8 mmol, 1.00 eq) and TosCl (3.69 g, 19.3 mmol, 1.30 eq) in pyridine (30 mL) was stirred at 80° C. for 5 h. The reaction mixture was partitioned between ethyl acetate (30 mL) and water (30 mL) and the aqueous layer was extracted with ethyl acetate (3×30 mL). The combined organic layer was washed with 0.5 MHCl (3×50 mL), dried over $Na_2SO_4$, filtered and concentrated under reduced pressure to give 40 (4.06 g, 12.7 mmol, 85% yield) as a brown solid which was used in the next step directly.

$^1$H NMR: (400 MHz, Chloroform-d) 7.59-7.54 (m, 2H), 7.23 (d, J=7.9 Hz, 2H), 7.10 (d, J=8.4 Hz, 1H), 6.71 (d, J=3.1 Hz, 1H), 6.68-6.63 (m, 1H), 6.12 (s, 1H) 3.79 (s, 3H) 2.88-2.77 (m, 1H), 2.40 (s, 3H), 0.96 (d, J=6.6 Hz, 6H).

General Procedure for Preparation of Compound 41:

To a solution of 40 (3.56 g, 11.15 mmol, 1.00 eq) in $CH_3CN$ (30.0 mL) was added TFA (1.75 g, 15.4 mmol, 1.14 mL, 1.38 eq) and NCS (1.49 g, 11.1 mmol) at 0° C. Then the mixture was stirred at 80° C. for 1 h. The reaction mixture was partitioned between ethyl acetate (50 mL) and water (50 mL). Then the aqueous layer was extracted with ethyl acetate (3×50 mL). The combined organic layer was dried over $Na_2SO_4$, filtered and concentrated under reduced pressure to give a crude product. The crude product was purified by column, chromatography on silica gel to give 41 (3.59 g, 10.1 mmol, 91% yield) as a brown solid which was used for the next step.

$^1$H NMR: (400 MHz, chloroform-d) 7.58-7.54 (m, 2H), 7.24-7.21 (m, 2H), 7.13 (s, 1H), 6.68 (s, 1H), 3.85 (s, 3H), 2.87 (quin, J=6.8 Hz, 1H), 2.39 (s, 3H), 0.95 (d, J=6.6 Hz, 6H).

General Procedure for Preparation of Compound 42:

To a mixture of 41 (2.70 g, 7.63 mmol, 1.00 eq) and phenol (1.53 g, 16.25 mmol, 1.43 mL, 2.13 eq) was added hydrogen bromide in HOAc (22.5 g, 97.4 mmol, 15.1 mL, 35% w.t., 12.8 eq). The mixture was stirred for 12 h at 40° C. The reaction mixture was adjusted to pH=9 by progressively adding aq. NaOH (6 μmol/L, 50 mL). Then $H_2O$ (40 mL) was added. The mixture was extracted with methyl tert-butyl ether (4×100 mL). The combined organic phases were dried over anhydrous $Na_2SO_4$, filtered and concentrated in vacuum. The residue was purified by prep-HPLC to give 42 (1.20 g, 6.01 mmol, 78% yield) as brown oil.

$^1$H NMR: (400 MHz, Chloroform-d) 6.75 (s, 1H), 6.72 (s, 1H), 3.84 (s, 3H), 3.44 (br. s., 2H), 2.93-2.84 (m, 1H), 1.25 (d, J=7.1 Hz, 6H).

General Procedure for Preparation of Compound 43:

To a solution of 42 (600 mg, 3.00 mmol, 1.00 eq) in $CH_3OH$ (25.0 mL) and HCl (1 μmol/L, 9.00 mL, 3.00 eq.) was added drop-wise a solution of $NaNO_2$ (311 mg, 4.51 mmol, 245 μL, 1.50 eq) in $H_2O$ (6.00 mL) within 0.5 h at 0° C. Then the mixture was added to a solution of potassium ethylxanthate (962 mg, 6.00 mmol, 2.00 eq) in $H_2O$ (14.00 mL) at 65° C. Then the mixture was stirred for 0.5 h at 65° C. Ethyl acetate (20 mL) was added. The organic layer was separated. The aqueous layer was extracted with ethyl acetate (3×30 mL). The extractions were combined, dried over anhydrous $Na_2SO_4$ and filtered. The filtrate was concentrated to give 43 (700 mg, 130 mmol, 77% yield) as brown oil which was used in the next step directly.

$^1$H NMR: (400 MHz, DMSO-d6) 7.45 (s, 1H), 6.96 (s, 1H), 3.99-3.83 (m, 5H), 3.38-3.36 (m, 1H), 1.35-1.19 (m, 9H).

General Procedure for Preparation of Compound 44:

To a solution of 43 (700 mg, 2.30 mmol, 1.00 eq) in EtOH (8.40 mL) was added NaOH (3 μmol/L, 8.43 mL, 11.0 eq) at 10° C. Then mixture was heated to 65° C. and stirred for 2 h. The mixture was cooled to room temperature. 1,4-dithioerythritol (70 mg, 0.45 mmol) was added. The mixture was adjusted to pH=5 with aq. HCl (1 μmol/L, 25 mL). The mixture was extracted with ethyl acetate (3×60 mL). The extractions were combined, dried over anhydrous $Na_2SO_4$ and filtered. The filtrate was concentrated to give 44 (630 mg, crude) as light yellow oil which was used in the next step directly.

$^1$H NMR: (400 MHz, Chloroform-d) 7.36-7.34 (m, 1H), 6.81 (s, 1H), 3.90 (s, 3H), 3.54-3.41 (m, 1H), 1.25 (d, J=7.1 Hz, 6H).

General Procedure for Preparation of Compound 45:

To a mixture of 44 (630 mg, 2.91 mmol, 1.00 eq) in acetonitrile (6.30 mL) was added $Cs_2CO_3$ (1.42 g, 4.37 mmol, 1.50 eq) and 2-bromoacetonitrile (349 mg, 2.91 mmol, 194 μL, 1.00 eq) in one portion. The mixture was stirred at 80° C. for 12 h. $H_2O$ (50 mL) was added and the mixture was extracted with ethyl acetate (3×50 mL). The combined organic phase was washed with brine (50 mL), dried over anhydrous $Na_2SO_4$, filtered and concentrated in vacuum to give brownish dark oil. The residue was purified by silica gel chromatography to give 45 (210 mg, 821 μmol, 28% yield) as a light yellow oil.

$^1$H NMR: (400 MHz, Chloroform-d) 7.62 (s, 1H), 6.89 (s, 1H) 3.95 (s, 3H), 3.67 (td, J=6.7, 13.9 Hz, 1H), 3.46 (s, 2H), 1.27 (d, J=7.1 Hz, 6H).

General Procedure for Preparation of Compound 46:

To a mixture of 45 (210 mg, 821 μmol, 1.00 eq) in N,N-dimethylformamide (2.10 mL) was added 1-tert-butoxy-N,N,N',N'-tetramethyl-methanediamine (286 mg, 1.64 mmol, 340 μL, 2.00 eq). The mixture was stirred at 110° C.

for 1.5 h. The mixture was used in the next step directly without work up and purification.

General Procedure for Preparation of Compound 47:

To a mixture of 46 (255 mg, 820 μmol, 1.00 eq) in N,N-dimethylformamide (2.10 mL) was added aniline (532 mg, 4.10 mmol, 521 μL, 5.00 eq, HCl) at 120° C. The mixture was stirred at 120° C. for 5 h. H$_2$O (30 mL) was added and the mixture was extracted with ethyl acetate (3×30 mL). The combined organic phase was dried over anhydrous Na$_2$SO$_4$, filtered and concentrated in vacuum to give 47 (650 mg, crude) as brownish oil which was used in the next step directly.

$^1$H NMR: (400 MHz, Chloroform-d) 7.55 (d, J=7.9 Hz, 5H), 7.00 (s, 1H), 6.99 (m, 1H), 6.86 (s, 1H), 3.95 (br. s., 1H), 3.91 (s, 3H), 3.53-3.45 (m, 1H), 1.28 (d, J=7.1 Hz, 5H).

General Procedure for Preparation of Compound 9:

To a solution of 47 (785 mg, 2.19 mmol, 1.00 eq) in dimethylsulfoxide (2.30 mL) was added guanidine carbonate (11.6 g, 64.3 mmol, 1.20 eq) and sodium methoxide (473 mg, 2.63 mmol, 2.50 eq). Then the mixture was heated to 110° C. and stirred for 12 h. H$_2$O (50 mL) was added and the mixture was extracted with ethyl acetate (3×70 mL). The combined organic phase was dried over anhydrous Na$_2$SO$_4$, filtered and concentrated to give light yellow solid. The solid was purified by prep-HPLC to give 9 (40.0 mg, 123 μmol, 5.6% yield) as a light brown solid.

$^1$H NMR: (400 MHz, DMSO-d$_6$) 7.88 (s, 1H), 7.01 (s, 1H), 6.73 (s, 1H), 6.40 (br. s., 2H), 3.84 (s, 3H), 3.44-3.37 (m, 1H), 1.25 (d, J=7.1 Hz, 6H).

LCMS: [M+H]$^+$ 325.0.

Example 10

Synthesis of Compound 10

Compound 10 was made by the synthetic method outlined in Scheme N:

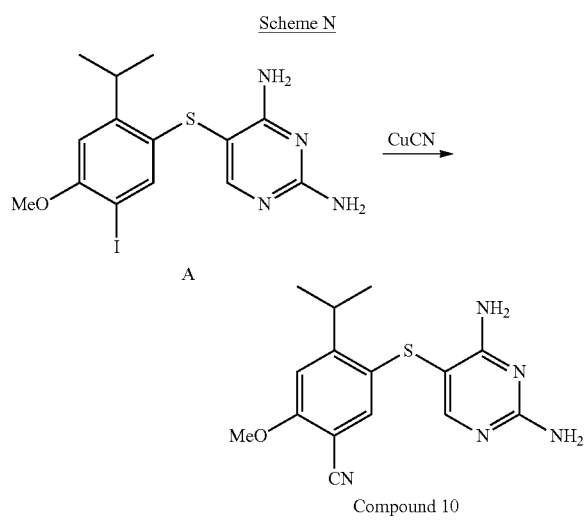

Compound 4 was prepared as outlined above in Example 4.

General Procedure for Preparation of Compound 10:

To a solution of 4 (500 mg, 1.20 mmol, 1.00 eq) in DMF (5.00 mL) was added CuCN (215 mg, 2.40 mmol, 2.00 eq). Then the mixture was stirred at 120° C. for 2 h. The mixture was cooled to room temperature, concentrated under reduced pressure and directly purified by prep-HPLC and SFC separation to give 10 (29.0 mg, 91.9 μmol, 7% yield) as a white solid.

$^1$H NMR: (400 MHz, DMSO-d6) 7.95 (br. s., 1H), 7.12 (s, 1H), 7.05 (s, 1H), 6.65 (br. s., 2H), 3.92 (s, 3H), 3.49-3.43 (m, 1H), 1.26 (d, J=6.6 Hz, 6H).

LCMS: [M+H]$^+$ 316.1.

Example 11

Synthesis of Compound 11

Compound 11 was made by the synthetic method outlined in Scheme O:

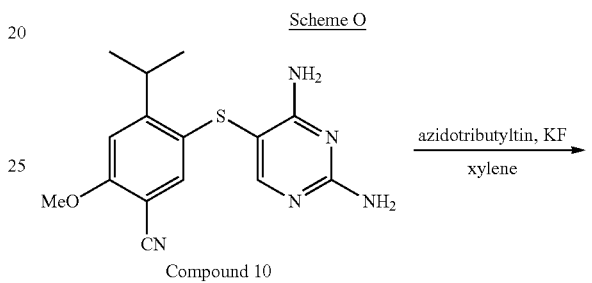

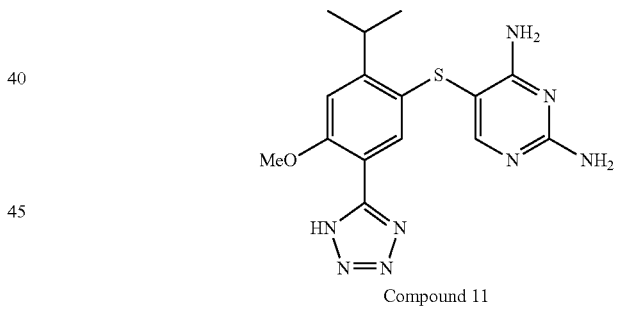

Compound 10 was prepared as outlined above in Example 10.

General Procedure for Preparation of Compound 11:

To a solution of 10 (200 mg, 634 μmol, 1.00 eq) in xylene (2.00 mL) was added azidotributyltin (3.37 g, 10.1 mmol. 16.0 eq) at 120° C. The mixture was stirred at 120° C. for 12 h. The mixture was cooled to room temperature and KF (737 mg, 12.7 mmol, 297 μL, 20.00 eq) was added. Then the mixture was concentrated under reduced pressure to give a residue which was purified by prep-HPLC to give 11 (35.0 mg, 97.6 μmol, 15% yield) as a white solid.

$^1$H NMR: (400 MHz, DMSO-d$_6$) 7.90 (br. s., 1H), 7.53 (br. s., 1H), 7.11 (br. s., 1H), 6.42 (br. s., 2H), 3.95 (br. s., 3H), 3.46 (d, J=6.1 Hz, 1H), 1.30 (d, J=5.9 Hz, 6H).

LCMS: [M+H]$^+$ 359.1 (M+1)$^+$.

Example 12

Synthesis of Compound 12

Compound 12 was made by the synthetic method outlined in Scheme P:

Scheme P

Compound 10

Compound 12

Compound 10 was prepared as outlined above in Example 10.

General Procedure for Preparation of Compound 12:

To a solution of 10 (100 mg, 317.07 μmol, 1.00 eq) in EtOH (1.0 mL) was added NaOH (317 mg, 7.93 mmol, 25.00 eq) in $H_2O$ (1.0 mL). Then the mixture was stirred at 80° C. for 12 h. The mixture was adjusted to pH=7 with aqueous HCl (1 M) and the mixture was purified by prep-HPLC to give 12 (15.0 mg, 44.8 μmol, 14% yield) as a white solid.

$^1$H NMR: (400 MHz, DMSO-$d_6$) 7.86 (br. s., 1H), 7.01 (br. s., 1H), 6.92 (br. s., 1H), 6.37 (br. s., 2H), 3.76 (br. s., 3H), 3.43 (br. s., 1H), 1.24 (d, J=6.6 Hz, 6H).

LCMS: [M+H]$^+$ 335.1.

Example 13

Synthesis of Comparative Compound 1

Comparative compound 1 was made by the synthetic method outlined in Scheme Q:

Scheme Q

1

Comparative compound 1

Compound 1 was prepared as outlined above in Example 1.

General Procedure for Preparation of Comparative Compound 1:

Batch 1:
To a solution of 1 (20.0 mg, 62.4 μmol, 1.00 eq) in dichloromethane (1.00 mL) was added a solution of m-CPBA (13.5 mg, 62.4 μmol, 80.0% purity, 1.00 eq) in dichloromethane (1.00 mL) at 0° C. The reaction mixture was stirred at 25° C. for 0.5 h.

Batch 2:
To a solution of 1 (100 mg, 312 μmol, 1.00 eq) in dichloromethane (5.00 mL) was added a solution of m-CPBA (67.3 mg, 312 μmol, 80.0% purity, 1.00 eq) in dichloromethane (1.00 mL) at 0° C. The reaction mixture was stirred at 0° C. for 0.5 h.

The above two mixtures from Batch 1 and Batch 2 were combined, washed with sat. $Na_2SO_3$ (10 mL) and sat. $Na_2CO_3$ (2×10 mL). The combined organic layers were washed with brine (20 mL), dried over anhydrous $Na_2SO_4$, filtered and concentrated in vacuum. The residue was purified by prep-TLC to give Comparative compound 1 (60.0 mg, 178 μmol, 57.1% yield) as a white solid.

$^1$H NMR: (400 MHz, Methanol-$d_4$) 7.81 (s, 1H), 7.52 (s, 1H), 6.99 (s, 1H), 3.89 (d, J=7.06 Hz, 6H), 3.04-3.13 (m, 1H), 1.28 (d, J=6.62 Hz, 3H), 0.95 (d, J=6.62 Hz, 3H).

LCMS: [M+H]$^+$ 337.0.

Example 14

Synthesis of Comparative Compound 2

Comparative compound 2 was made by the synthetic method outlined in Scheme R:

Scheme R

1

Comparative compound 2

Starting material Compound 1 was prepared as outlined above in Example 1.

General Procedure for Preparation of Comparative Compound 2:

To a solution of 1 (400 mg, 1.25 mmol, 1.00 eq) in dichloromethane (5.00 mL) was added m-CPBA (539 mg, 2.50 mmol, 80.0% purity, 2.00 eq) at 0° C. The reaction mixture was stirred at 20° C. for 12 h. Dichloromethane (10 mL) was added. The mixture was washed with sat. Na$_2$SO$_3$ (10 mL), sat. Na$_2$CO$_3$ (2×10 mL) and brine (10 mL) in sequence. Then the organic layer was dried over anhydrous Na$_2$SO$_4$, filtered and concentrated in vacuum. The residue was purified by prep-HPLC to give Comparative compound 2 (27.0 mg, 76.6 μmol, 6.1% yield) was obtained as a white solid.

$^1$H NMR: (400 MHz, Methanol-d$_4$) 8.23 (s, 1H), 7.63 (s, 1H), 7.01 (s, 1H), 3.90 (s, 6H), 3.65 (dt, J=13.56, 6.67 Hz, 1H), 1.11 (d, J=6.62 Hz, 6H)

LCMS: [M+H]$^+$ 353.1.

Example 15

Synthesis of Compound 13

Compound 13 was made by the synthetic method outlined in Scheme S:

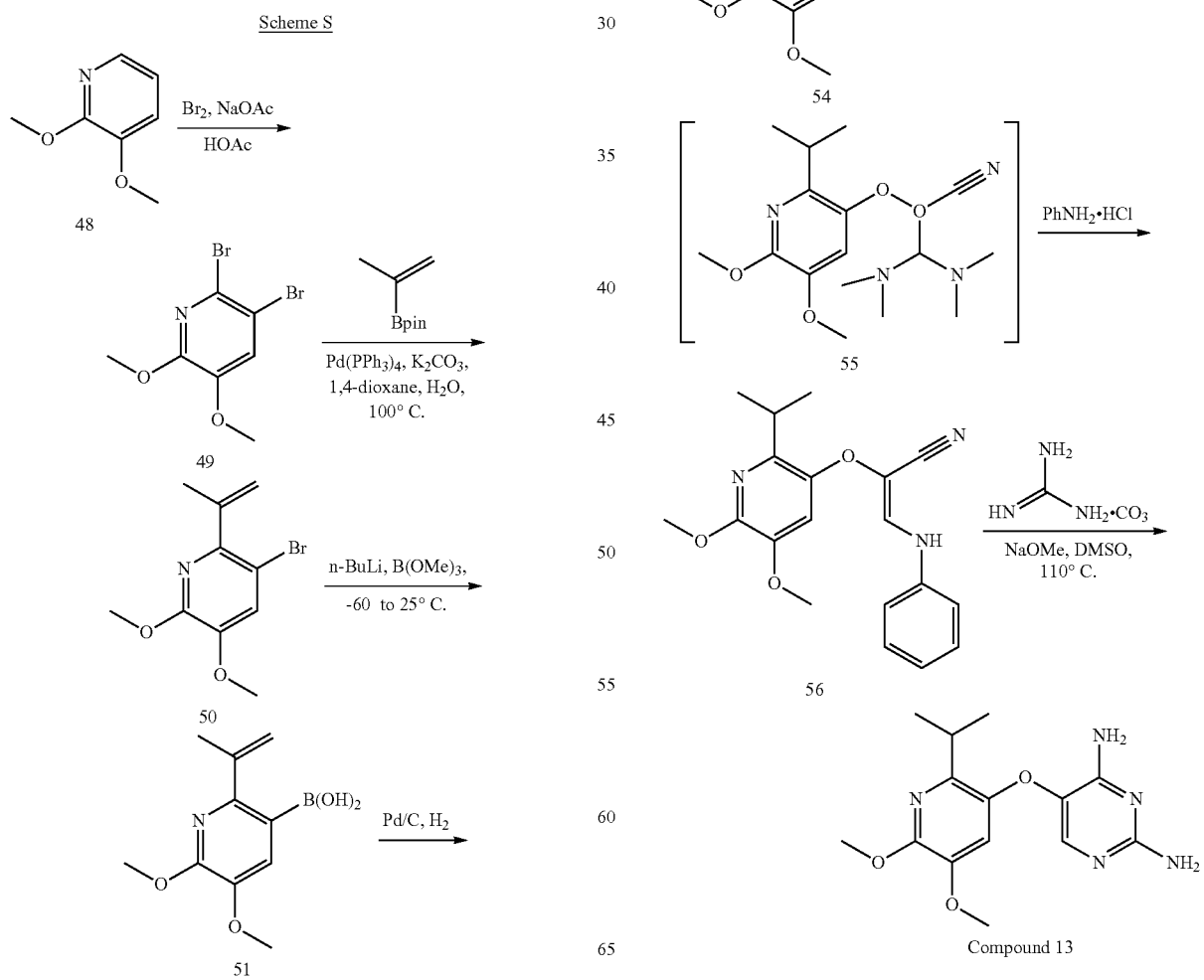

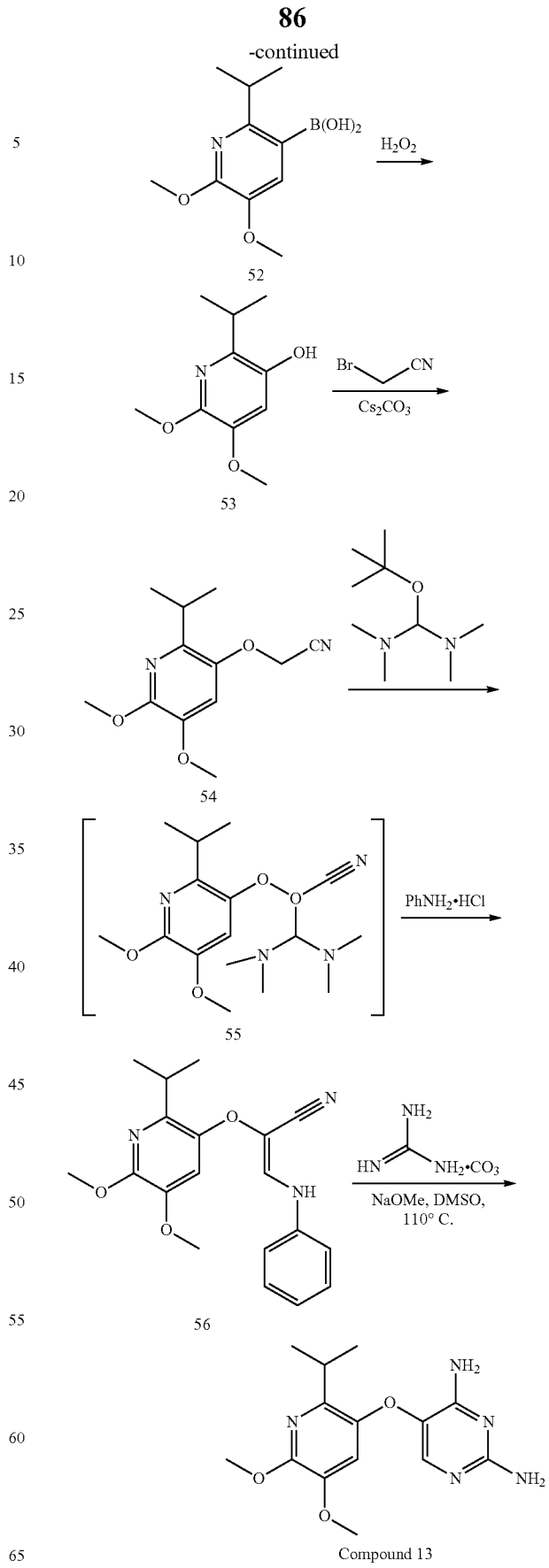

Compound 13

General Procedure for Preparation of Compound 49:

To the solution of compound 48 (5.00 g, 35.9 mmol, 1.00 eq), NaOAc (8.84 g, 107 mmol, 3.00 eq) in HOAc (65.0 mL) was added $Br_2$ (20.1 g, 125 mmol, 6.48 mL, 3.50 eq), while maintaining the inner temperature below 25° C. The mixture was stirred at 25° C. for 20 h. The mixture was poured into ice water and neutralized to pH=7 with 25% aqueous NaOH solution. The aqueous phase was extracted with $CH_2Cl_2$ (3×100 mL). The organic phases were combined and washed with brine (100 mL), dried over anhydrous $Na_2SO_4$, filtered and concentrated to give compound 49 (9.20 g, 30.9 mmol, 86.2% yield) as a brown solid, which was used in the next step without purification.

$^1$H NMR (400 MHz, Chloroform-d) δ=7.22 (s, 1H), 4.01 (s, 3H), 3.87 (s, 3H).

General Procedure for Preparation of Compound 50:

The mixture of compound 49 (9.00 g, 30.3 mmol, 1.00 eq), Isopropenylboronic acid pinacol ester (5.09 g, 30.3 mmol, 1.00 eq), $K_2CO_3$ (8.38 g, 60.6 mmol, 2.00 eq) and $Pd(PPh_3)_4$ (4.20 g, 3.64 mmol, 0.12 eq) in 1,4-dioxane (100 mL) and $H_2O$ (25.0 mL) was stirred at 100° C. under $N_2$ atmosphere for 6 h. The mixture was filtered and washed with ethyl acetate (20 mL). To the filtrate was added ethyl acetate (50 mL) and brine (30 mL). The aqueous phase was separated and extracted with ethyl acetate (3×100 mL). The organic phases were combined and dried over anhydrous $Na_2SO_4$, filtered and concentrated. The residue was purified via column chromatography on silica gel to give compound 50 (4.00 g, 15.5 mmol, 51.1% yield) as a light yellow liquid.

$^1$H NMR (400 MHz, Chloroform-d) δ=7.20 (s, 1H), 5.39 (s, 1H), 5.33 (s, 1H), 3.99 (s, 3H), 3.88 (s, 3H), 2.14 (s, 3H).

General Procedure for Preparation of Compound 51:

To the solution of compound 50 (3.00 g, 11.6 mmol, 1.00 eq) in THF (80.0 mL) was added n-BuLi (2.5 M, 9.30 mL, 2.00 eq) at −60° C. under $N_2$ atmosphere. The mixture was stirred at −60° C. for 1 h. Then $B(OMe)_3$ (3.62 g, 34.9 mmol, 3.00 eq) was added. The mixture was allowed to warm to 20° C. and stirred for 13 h. The reaction mixture was quenched with $H_2O$ (20 mL) at 0° C. and then was adjusted to pH=4 with 1 N HCl (30 mL). Two phases were separated and the aqueous phase was extracted with ethyl acetate (3×100 mL). The organic phases were combined, dried over anhydrous $Na_2SO_4$, filtered and concentrated. The residue was purified via column chromatography on silica gel to give compound 51 (1.10 g, 4.93 mmol, 42.4% yield) as yellow liquid, which was used in the next step without purification.

$^1$H NMR (400 MHz, Chloroform-d) δ=7.45 (s, 1H), 5.37 (br. s., 1H), 5.15 (br. s., 1H). 4.02 (br. s., 3H), 3.91 (s, 3H), 3.73 (s, 2H), 2.22 (br. s., 3H).

General Procedure for Preparation of Compound 52:

A mixture of compound 51 (1.10 g, 4.93 mmol, 1.00 eq) and Pd/C (524.87 mg, 4.93 mmol, 5% w.t., 1.00 eq) in MeOH (50.00 mL) was stirred at 20° C. under $H_2$ balloon for 15 h. The mixture was filtered through a pad of celite and the filter cake was washed with MeOH (150 mL). The combined filtrates were concentrated to give compound 52 (800 mg, 3.55 mmol, 72.1% yield) as a yellow liquid, which was used in the next step without purification.

$^1$H NMR (400 MHz, Chloroform-d) δ=7.75 (s, 1H), 4.22-4.15 (m, 1H), 4.11 (s, 3H), 3.95 (s, 3H), 3.78-3.73 (m, 2H), 1.35 (d, J=6.7 Hz, 6H).

General Procedure for Preparation of Compound 53:

To the solution of compound 52 (290 mg, 1.29 mmol, 1.00 eq) in $CH_3CN$ (9.00 mL) was added $H_2O_2$ (292 mg, 2.58 mmol, 30% w.t, 2.00 eq). The mixture was stirred at 20° C. for 0.5 h. To the mixture was added saturated aqueous $Na_2SO_3$ (5 mL) at 0° C. Then the mixture was stirred at 20° C. for 5 min. To the mixture was added ethyl acetate (20 mL) and $H_2O$ (5 mL). The aqueous phase was separated and extracted with ethyl acetate (3×20 mL). The organic phases were combined, dried over anhydrous $Na_2SO_4$ and concentrated to give compound 53 (240 mg, 1.22 mmol, 94.3% yield) as a yellow liquid which was used in the next step without purification.

$^1$H NMR (400 MHz, Chloroform-d) δ=6.68 (s, 1H), 4.27 (br. s., 1H), 3.98 (s, 3H), 3.83 (s, 3H), 3.12 (td, J=6.8, 13.7 Hz, 1H), 1.25 (d, J=6.7 Hz, 6H).

General Procedure for Preparation of Compound 54:

To compound 53 (120 mg, 608 μmol, 1.00 eq) in $CH_3CN$ (3.00 mL) was added $Cs_2CO_3$ (297 mg, 912 μmol, 1.50 eq) and $BrCH_2CN$ (109.47 mg, 912.65 μmol, 1.50 eq). The mixture was stirred at 80° C. for 15 h. To the reaction mixture was added ethyl acetate (10 mL) and water (4 mL). The aqueous phase was separated and extracted with ethyl acetate (3×10 mL). The organic phases were combined, dried over anhydrous $Na_2SO_4$, filtered and concentrated to give compound 54 (135 mg, 571 μmol, 94% yield) as a dark brown solid which was used in the next step without purification.

$^1$H NMR (400 MHz, DMSO-$d_6$) δ=7.28 (s, 1H), 5.16 (s, 2H), 3.84 (s, 3H), 3.78 (s, 3H), 3.22-3.25 (m, 1H), 1.15 (d, J=7.0 HZ, 6H).

General Procedure for Preparation of Compound 55:

The mixture of compound 54 (200 mg, 846 umol, 1.00 eq) and 1-tert-butoxy-N,N,N',N'-tetramethyl-methanediamine (295 mg, 1.69 mmol, 2.00 eq) in DMF (2.00 mL) was stirred at 110° C. for 3 h. The reaction mixture was used in the next step directly.

General Procedure for Preparation of Compound 56:

To the solution of compound 55 (284 mg, 846 umol, 1.00 eq) in DMF (2.00 mL) was added $PhNH_2$ (219 mg, 1.69 mmol, 2.00 eq, HCl). The mixture was stirred at 120° C. for 3 h. LCMS showed the starting material was consumed completely. To the mixture was added toluene (30 mL) and $H_2O$ (6 mL). The two phases were separated and the aqueous phase was extracted with toluene (3×15 mL). The organic phases were combined, dried over anhydrous $Na_2SO_4$, filtered and concentrated to give compound 56 (280 mg, 825 μmol, 97% yield) as dark liquid which was used in the next step without purification.

$^1$H NMR (400 MHz, Chloroform-d) δ=7.37-7.34 (m, 2H), 7.16 (d, J=5.7 Hz, 2H), 6.95 (d, J=7.9 Hz, 1H), 6.80 (s, 1H), 6.70 (d, J=7.5 Hz, 1H), 4.69 (s, 1H), 4.02 (s, 3H), 3.85 (s, 3H), 3.37-3.25 (m, 1H), 1.28 (d, J=7.1 Hz, 6H).

General Procedure for Preparation of 13:

A mixture of compound 56 (140 mg, 412 umol, 1.00 eq), guanidine carbonate (111 mg, 618 umol, 1.50 eq) and NaOMe (66.8 mg, 1.24 mmol, 3.00 eq) in DMSO (1.50 mL) was stirred at 110° C. for 1 h. One additional vial was set up as described above. All the two reaction mixtures were combined and filtered. The filtrate was purified via prep-HPLC to give compound 13 (46.00 mg, 148 μmol, 36% yield) as a yellow solid.

$^1$H NMR (400 MHz, DMSO-$d_6$) δ=7.18 (s, 1H), 6.81 (s, 1H), 6.44 (br. s., 2H), 5.72 (s, 2H), 3.86 (s, 3H), 3.68 (s, 3H). 3.24 (td, J=6.7, 13.6 Hz, 1H), 1.16 (d, J=6.6 Hz, 6H).

LCMS: 98.2% purity, m/z=306.0 (M+1)$^+$.

Example 16

Synthesis of Compound 14

Compound 14 was made by the synthetic method outlined in Scheme T:

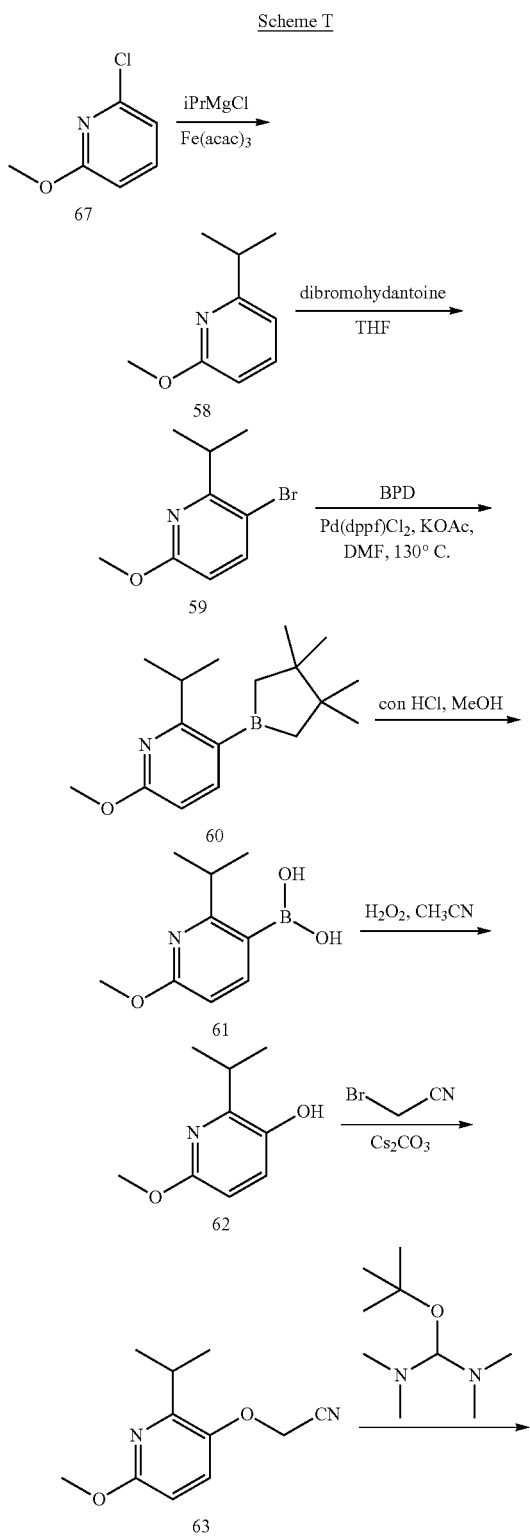

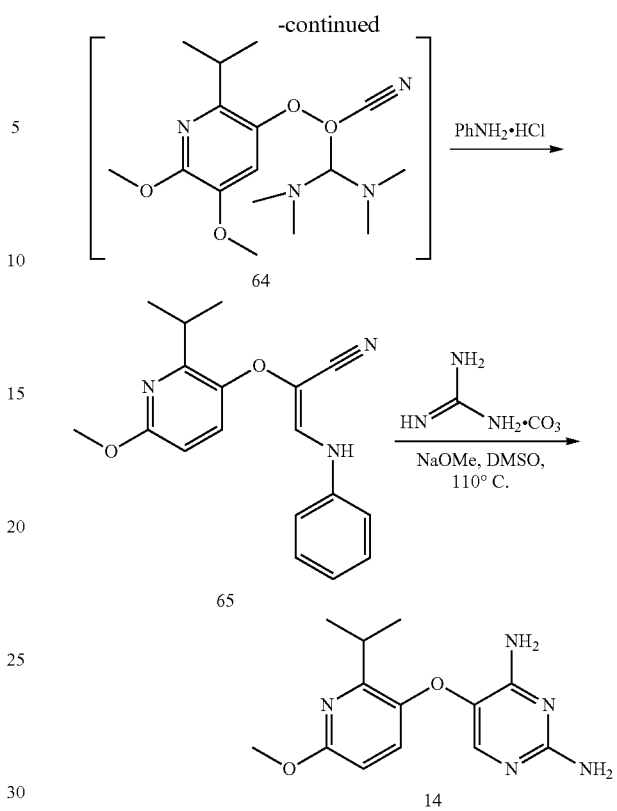

General Procedure for Preparation of Compound 58:

To the solution of Compound 57 (10.0 g, 69.6 mmol, 1.00 eq) in THF (200 mL) and NMP (20.0 mL) was added Fe(acac)$_3$ (1.23 g, 3.48 mmol, 0.05 eq). Then i-PrMgCl (2 M, 41.79 mL, 1.20 eq) was added dropwise at −30° C. within 30 min. The mixture was stirred at 0° C. for 1 h. The reaction mixture was quenched with saturated aqueous NH$_4$Cl (80 mL) at 0° C. Then the two phases were separated and the aqueous phase was extracted with methyl t-butyl ether (80 mL). The combined organic phases were washed with water (4×50 mL). Then the organic phase was dried over anhydrous Na$_2$SO$_4$, filtered and concentrated to give compound 58 (7.10 g, 46.9 mmol, 67% yield) as a yellow liquid which was used for the next step without purification.

$^1$H NMR (400 MHz, Chloroform-d) δ=7.48 (t, J=7.7 Hz, 1H), 6.72 (d, J=7.1 Hz, 1H), 6.54 (d, J=7.9 Hz, 1H), 3.93 (s, 3H), 2.95 (td, J=6.8, 13.7 Hz, 1H), 1.28 (d, J=7.1 Hz, 6H).

General Procedure for Preparation of Compound 59:

To the solution of compound 58 (8.50 g, 56.2 mmol, 1.00 eq) in THF (85.0 mL) was added 1,3-dibromo-5,5-dimethyl-imidazolidine-2,4-dione (16.1 g, 56.2 mmol, 1.00 eq). The mixture was stirred at 20° C. for 3 h. To the mixture was added water (50 mL) and ethyl acetate (30 mL). The two phases were separated and the aqueous phase was extracted with ethyl acetate (3×40 mL). The combined organic phases were dried over anhydrous Na$_2$SO$_4$, filtered and concentrated. The residue was purified via column chromatography on silica gel to give Compound 59 (7.10 g, 30.8 mmol, 54.9% yield) as a colorless liquid.

$^1$H NMR (400 MHz, Chloroform-d) δ=7.58 (d, J=8.8 Hz, 1H), 6.42 (d, J=8.4 Hz, 1H), 3.89 (s, 3H), 3.42 (td, J=6.8, 13.3 Hz, 1H), 1.23 (d, J=7.1 Hz, 6H).

General Procedure for Preparation of Compound 60:

The mixture of compound 59 (7.10 g, 30.8 mmol, 1.00 eq), BPD (Bis(pinacolato)diboron, 11.7 g, 46.3 mmol, 1.50 eq), Pd(dppl)Cl$_2$ (1.13 g, 1.54 mmol, 0.05 eq) and KOAc (6.06 g, 61.7 mmol, 2.00 eq) in DMF (71.0 mL) was stirred at 130° C. under N$_2$ atmosphere for 0.5 h. To the mixture was added water (30 mL) and ethyl acetate (30 mL). The two phases were separated and the aqueous phase was extracted with ethyl acetate (2×30 mL). The combined organic phases were dried over anhydrous Na$_2$SO$_4$, filtered and concentrated. The residue was purified via column chromatography on silica gel to give compound 60 (4.30 g, 15.5 mmol, 50% yield) as a yellow liquid.

$^1$H NMR (400 MHz, Chloroform-d) δ=7.90 (d, J=8.2 Hz, 1H), 6.50 (d, J=8.2 Hz, 1H), 3.95 (s, 3H), 3.74 (td, J=6.7, 13.3 Hz, 1H), 1.37-1.31 (m, 12H), 1.24 (d, J=6.7 Hz, 6H).

General Procedure for Preparation of Compound 61:

To a solution of compound 60 (4.60 g, 16.6 mmol, 1.00 eq) in MeOH (8.00 mL) was added HCl (12 M, 46.1 mL, 33.3 eq). The mixture was stirred at 65° C. for 2 h. The mixture was cooled to room temperature, and was adjusted to pH=5 with 10 N NaOH (60 mL). To the mixture was added ethyl acetate (100 mL). The aqueous phase was separated and extracted with ethyl acetate (3×50 mL). The organic phases were combined and dried over anhydrous Na$_2$SO$_4$. Then filtered and concentrated to give 61 (3.20 g, 16.4 mmol, 99% yield) as a yellow liquid which was used for the next step without purification.

$^1$H NMR (400 MHz, Chloroform-d) δ=8.29 (d, J=8.4 Hz, 1H), 6.68-6.63 (m, 1H), 4.13 (td, J=6.6, 13.2 Hz, 1H), 4.03 (s, 3H), 1.37 (d, J=7.1 Hz, 6H).

General Procedure for Preparation of Compound 62:

To a solution of compound 61 (3.20 g, 16.4 mmol, 1.00 eq) in CH$_3$CN (50.0 mL) was added hydrogen peroxide (3.72 g, 32.8 mmol 30% w.t., 2.00 eq). The mixture was stirred at 20° C. for 0.5 h. To the mixture was added saturated Na$_2$SO$_3$ solution (50 mL) at 0° C. Then the mixture was stirred at 20° C. for 10 min. To the mixture was added ethyl acetate (100 mL) and H$_2$O (10 mL). The aqueous phase was separated and extracted with ethyl acetate (3×50 mL). The organic phases were combined, washed with brine (50 mL) and dried over anhydrous Na$_2$SO$_4$. Then the solution was filtered and concentrated to give 62 (2.50 g, 14.95 mmol, 91% yield) as a yellow liquid which was used for the next step without purification.

$^1$H NMR (400 MHz, Chloroform-d) δ=7.05 (d, J=8.8 Hz, 1H), 6.45 (d, J=8.8 Hz, 1H), 4.45 (br. s., 1H), 3.89 (s, 3H), 3.31-3.20 (m, 1H), 1.27 (d, J=6.6 Hz, 6H).

General Procedure for Preparation of Compound 63:

To compound 62 (2.50 g, 14.95 mmol, 1.00 eq) in CH$_3$CN (30.00 mL) was added Cs$_2$CO$_3$ (7.31 g, 22.43 mmol, 1.50 eq) and BrCH$_2$CN (2.69 g, 22.4 mmol, 1.50 eq). The mixture was stirred at 80° C. for 13 h. To the reaction mixture was added ethyl acetate (60 mL) and water (30 mL). The aqueous phase was separated and extracted with ethyl acetate (3×50 mL). The organic phases were combined and washed with brine (50 mL). Then the solution was dried over anhydrous Na$_2$SO$_4$, filtered and concentrated to give 63 (2.90 g, 14.1 mmol, 94% yield) as a dark brown solid which was used for the next step without purification.

$^1$H NMR (400 MHz, DMSO-d$_6$) δ=7.56 (d, J=8.8 Hz, 1H), 6.67 (d, J=8.8 Hz, 1H), 5.14 (s, 2H), 3.82 (s, 3H), 3.36-3.27 (m, 1H), 1.17 (d, J=7.1 Hz, 6H).

General Procedure for Preparation of Compound 64:

A mixture of compound 63 (2.90 g, 14.1 mmol, 1.00 eq) and 1-tert-butoxy-N,N,N',N'-tetramethyl-methanediamine (4.90 g, 28.1 mmol, 5.83 mL, 2.00 eq) in DMF (30.0 mL) was stirred at 110° C. for 2 h. The reaction mixture was used in the next step directly.

General Procedure for Preparation of Compound 65:

To the solution of compound 64 (4.31 g, 14.07 mmol, 1.00 eq) in DMF (30.00 mL) was added PhNH$_2$ (4.56 g, 35.2 mmol, 4.47 mL, 2.50 eq, HCl). The mixture was stirred at 120° C. for 3 h. To the mixture was added toluene (80 mL) and H$_2$O (30 mL). The two phases were separated and the aqueous was extracted with toluene (3×30 mL). The organic phases were combined, washed with brine (30 mL). Then the solution was dried over anhydrous Na$_2$SO$_4$, filtered and concentrated to give compound 65 (5.00 g, crude) as a dark liquid which contained PhNH$_2$ and DMF. The crude product was used for the next step without purification.

$^1$H NMR. (400 MHz, Chloroform-d) δ=7.33 (t, J=7.3 Hz, 3H), 7.18-7.13 (m, 3H), 6.94 (d, J=7.9 Hz, 2H), 6.76 (t, J=7.3 Hz, 2H), 6.69 (d, J=7.9 Hz, 2H), 6.54 (d, J=8.8 Hz, 1H), 3.93 (s, 3H), 3.46-3.38 (m, 1H), 1.30 (d, J=7.1 Hz, 6H).

General Procedure for Preparation of Compound 14:

A mixture of compound 65 (2.50 g, 8.08 mmol, 1.00 eq), guanidine carbonate (2.18 g, 12.1 mmol, 1.50 eq) and NaOMe (1.31 g, 24.2 mmol, 3.00 eq) in DMSO (25.00 mL) was stirred at 110° C. for 1 h. One additional reaction was set up with the same amounts and conditions, and the two reaction mixtures were combined at the end of the heating period. To the mixture was added ethyl acetate (100 mL) and water (40 mL). The two phases were separated and the aqueous phase was extracted with ethyl acetate (2×50 mL). The organic phases were combined and washed with brine (30 mL), dried over anhydrous Na$_2$SO$_4$, filtered and concentrated. The residue was purified via prep-HPLC to give compound 14 (1.20 g, 4.36 mmol, 27% yield) as a light yellow solid.

$^1$H NMR (400 MHz, DMSO-d$_6$) δ=7.26 (s, 1H), 7.08 (d, J=8.8 Hz, 1H), 6.58 (d, J=8.8 Hz, 1H), 6.44 (br. s., 2H), 5.80 (s, 2H), 3.82 (s, 3H), 3.43-3.35 (m, 1H), 1.21 (d, J=6.6 Hz, 6H).

LCMS: 99.7% purity, m/z=276.1 (M+1)$^+$.

Example 17

Synthesis of Compound 15

Compound 15 was made by the synthetic method outlined in Scheme U:

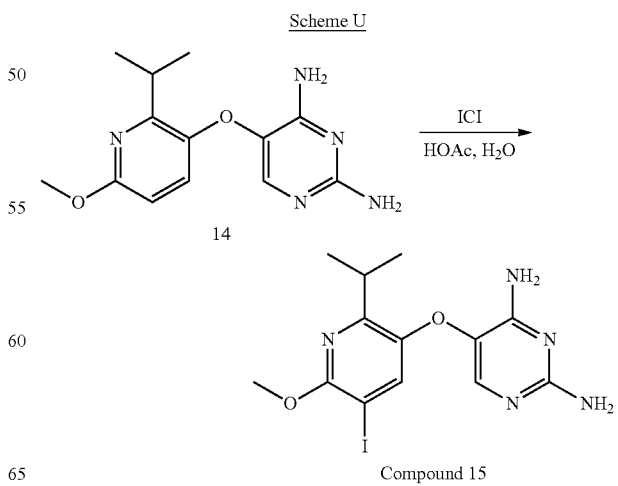

Starting material Compound 14 was prepared as outlined above in Example 16.

General Procedure for Preparation of Compound 15:

To a solution of 14 (250 mg, 908 umol, 1.00 eq) in HOAc (2.5 mL) was added a solution of ICl (295 mg, 1.82 mmol, 2.00 eq) in HOAc (2.5 mL). Then H$_2$O (4.00 mL) was added. The mixture was stirred at 90° C. for 2 h. Then a second portion of ICl (442 mg, 2.72 mmol, 3.00 eq) was added. The mixture was stirred at 90° C. for 4 h. The reaction mixture was adjusted to pH=8 with 1 N NaOH (2 mL) and saturated NaHCO$_3$ (3 mL). The mixture was extracted with ethyl acetate (3×15 mL). The combined organic phases were washed with saturated Na$_2$CO$_3$ (10 mL) and brine (10 mL), dried over anhydrous Na$_2$SO$_4$, filtered and concentrated. The residue was purified via prep-TLC (CH$_2$Cl$_2$:CH$_3$OH=20:1) to give compound 15 (40.0 mg, 99.7 umol, 11% yield) as a yellow solid.

$^1$H NMR (400 MHz, DMSO-d$_6$) δ=7.38 (s, 1H), 7.33 (s, 1H), 6.47 (br. s., 2H), 5.89 (s, 2H), 3.86 (s, 3H), 3.40-3.34 (m, 1H), 1.22 (d, J=6.6 Hz, 6H).

LCMS: 97.4% purity, m/z=401:9 (M+1)$^+$.

Example 18

Synthesis of Compound 16

Compound 16 was made by the synthetic method outlined in Scheme V:

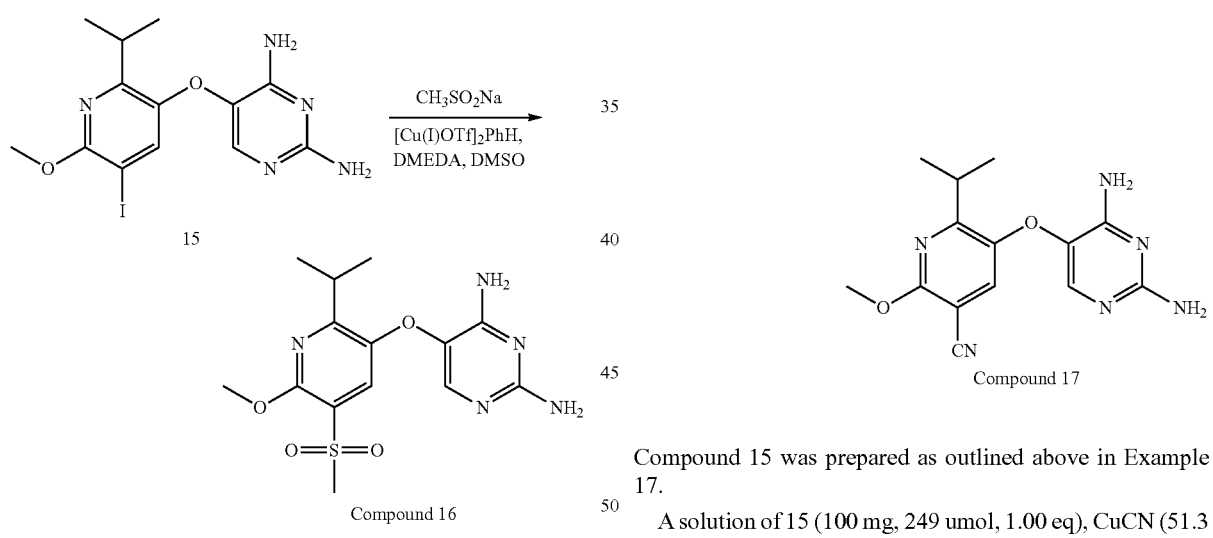

Compound 16

Compound 15 was prepared as outlined above in Example 17.

To a solution of 15 (400 mg, 997 umol, 1.00 eq), CH$_3$SO$_2$Na (254 mg, 2.49 mmol, 2.50 eq) and copper (I) trifluoromethanesulfonate-benzene complex (75.28 mg, 150 umol, 0.15 eq) in DMSO (8.00 mL) was added DMEDA (26.4 mg, 299 umol, 32.2 uL, 0.30 eq). The mixture was stirred at 120° C. under N$_2$ atmosphere for 4 h. To the mixture was added ethyl acetate (20 mL) and H$_2$O (10 mL). The two phases were separated and the aqueous phase was extracted with ethyl acetate (3×15 mL). The combined organic phases were washed with brine (10 mL), dried over anhydrous Na$_2$SO$_4$, filtered and concentrated. The residue was purified via prep-HPLC to give compound 16 (280 mg, 40% yield, 99.8% purity) as a white solid.

$^1$H NMR (400 MHz, DMSO-d$_6$) δ=7.51 (br. s., 1H), 7.28 (s, 1H), 6.53 (br. s., 2H), 5.98 (br. s., 2H), 4.02 (s, 3H), 3.59-3.48 (m, 1H), 3.25 (s, 3H), 1.27 (d, J=6.6 Hz, 6H).

LCMS: 99.8% purity, m/z=354.1 (M+1)$^+$.

Example 19

Synthesis of Compound 17

Compound 17 was made by the synthetic method outlined in Scheme W:

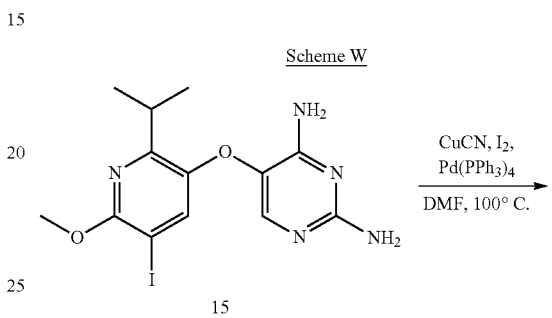

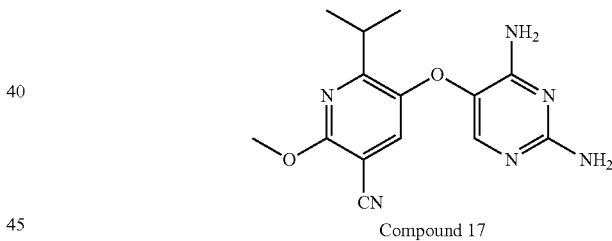

Compound 17

Compound 15 was prepared as outlined above in Example 17.

A solution of 15 (100 mg, 249 umol, 1.00 eq), CuCN (51.3 mg, 573 umol, 2.30 eq), Pd(PPh$_3$)$_4$ (57.6 mg, 49.8 umol, 0.20 eq), I$_2$ (25.3 mg, 99.7 umol, 0.40 eq) in DMF (2.00 mL) was stirred at 100° C. under N$_2$ atmosphere for 12 h. To the reaction mixture was added ethyl acetate (10 mL), saturated NH$_4$Cl (3 mL) and NH$_3$.H$_2$O (0.5 mL). The two phases were separated and the aqueous phase was extracted with ethyl acetate (3×5 mL). The combined organic phases were dried over anhydrous Na$_2$SO$_4$, filtered and concentrated. The residue was purified via prep TLC and then purified via prep-HPLC to give Compound 17 (15.0 mg, 48.9 umol, 20% yield, 97.9% purity) as a white solid.

$^1$H NMR (400 MHz, DMSO-d$_6$) δ=7.50 (s, 1H), 7.44 (s, 1H), 6.46 (br. s., 2H), 5.90 (s, 2H), 3.97 (s, 3H), 3.46 (quin, J=6.7 Hz, 1H), 1.24 (d, J=6.6 Hz, 6H).

LCMS: 97.9% purity, m/z=301.1 (M+1)$^+$.

Example 20

Synthesis of Compound 18

Compound 18 was made by the synthetic method outlined in Scheme X:

Scheme X

Compound 18

Starting material Compound 15 was prepared as outlined above in Example 17.

A solution of 15 (100 mg, 249 umol, 1.00 eq), 1,10-phenanthrolinetrifluoromethyl copper (624 mg, 1.99 mmol, 8.00 eq) and CuI (94.9 mg, 498 umol, 2.00 eq) in DMF (2.00 mL) was stirred at 80° C. under $N_2$ atmosphere for 6 h. The mixture was filtered and ethyl acetate (10 mL) and $H_2O$ (4 mL) were added to the filtrate. The two phases were separated and the aqueous phase was extracted with ethyl acetate (3×10 mL). The combined organic phases were dried over anhydrous $Na_2SO_4$, filtered and concentrated. The residue was purified via prep-HPLC to give compound 18 (13.0 mg, 37.3 umol, 15% yield, 98.5% purity) as a white solid.

$^1$H NMR (400 MHz, DMSO-$d_6$) δ=7.46 (s, 1H), 7.16 (s, 1H), 6.51 (br. s., 2H), 5.93 (br. s., 2H), 3.96 (s, 3H), 3.54-3.42 (m, 1H), 1.26 (d, J=6.6 Hz, 6H).

LCMS: 98.5% purity, m/z=344.2 (M+1)$^+$.

Example 21

Synthesis of Compound 19

Compound 19 was made by the synthetic method outlined in Scheme Y:

Scheme Y

Compound 19

Compound 15 was prepared as outlined above in Example 17.

General Procedure for Preparation of Compound 66:

To a solution of 15 (100 mg, 249 umol, 1.00 eq), Pd(PPh$_3$)$_2$ Cl$_2$ (35.0 mg, 49.8 umol, 0.20 eq) and CuI (4.75 mg, 24.9 umol, 0.10 eq) in THF (2.00 mL) was added ethynyl (trimethyl)silane (49.0 mg, 498 umol, 2.00 eq) and DIPEA (258 mg, 2.00 mmol, 8.00 eq). The mixture was stirred at 50° C. for 12 h. To the mixture was added ethyl acetate (4 mL) and saturated NH$_4$Cl (2 mL). The two phases were separated and the aqueous phase was extracted with ethyl acetate (3×3 mL). The combined organic phases were washed with brine (2 mL), dried with anhydrous Na$_2$SO$_4$, filtered and concentrated. The residue was purified via prep-TLC to give compound 66 (80.0 mg, 215 umol, 86% yield) as a light yellow solid.

$^1$H NMR (400 MHz, METHANOL-d4) δ=7.24 (s, 1H), 7.12 (s, 1H), 3.96 (s, 3H), 3.43-3.36 (m, 1H), 1.26 (d, J=6.7 Hz, 6H), 0.21 (s, 9H).

General Procedure for Preparation of Compound 19:

To the solution of 66 (75.0 mg, 201 umol, 1.00 eq) in THF (1.60 mL) was added CsF (153 mg, 1.01 mmol, 5.00 eq). The mixture was stirred at 50° C. for 5 h. Another portion of CsF (153 mg, 1.01 mmol, 5.00 eq) was added in. The mixture was stirred at 50° C. for 13 h. To the mixture was added ethyl acetate (10 mL) and saturated NH$_4$Cl (5 mL). The two phases were separated and the aqueous phase was extracted with ethyl acetate (4×10 mL). The combined organic phase was washed with brine (10 mL), dried over anhydrous Na$_2$SO$_4$, filtered and concentrated. The residue was purified via prep-HPLC to give compound 19 (26.0 mg, 84.9 umol, 42% yield, 97.7% purity) as a white solid.

$^1$H NMR (400 MHz, DMSO-$d_6$) δ=7.38 (s, 1H), 7.02 (s, 1H), 6.46 (br. s., 2H), 5.88 (s, 2H), 4.33 (s, 1H), 3.89 (s, 3H), 3.40 (quin, J=6.8 Hz, 1H), 1.22 (d, J=7.1 Hz, 6H).

LCMS: 97.7% purity, m/z=300.1 (M+1)$^+$.

Example 22

Synthesis of Compound 20

Compound 20 was made by the synthetic method outlined in Scheme Z:

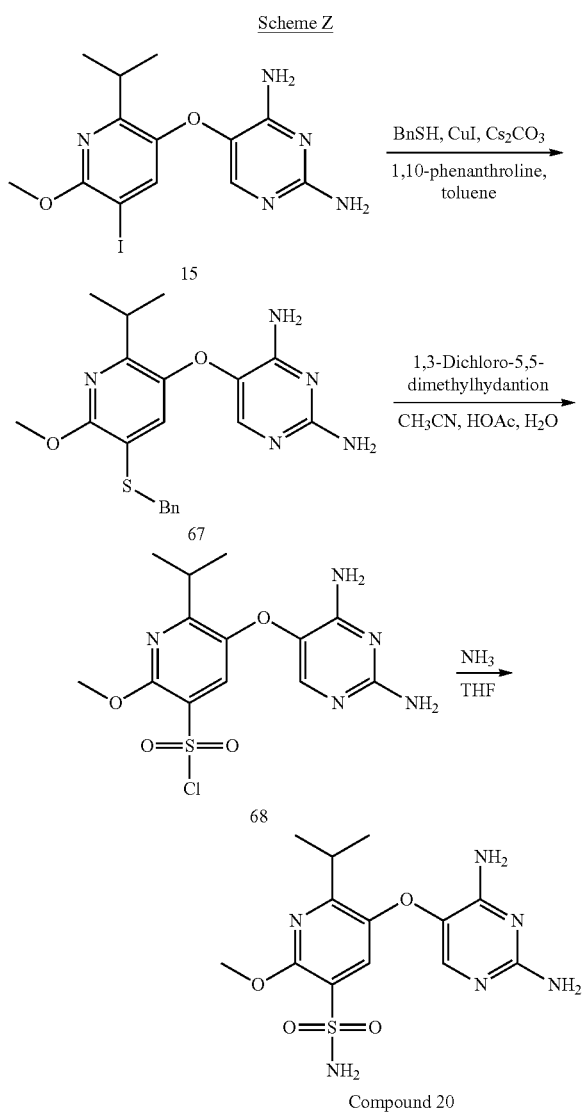

Compound 15 was prepared as outlined above in Example 17.

General Procedure for Preparation of Compound 67:

To the mixture of 15 (1.00 g, 2.49 mmol, 1.00 eq), CuI (213 mg, 1.12 mmol, 0.45 eq), 1,10-phenanthroline (202 mg, 1.12 mmol, 0.45 eq) and Cs₂CO₃ (1.22 g, 3.74 mmol, 1.50 eq) was added toluene (20.0 mL) and phenylmethanethiol (3.09 g, 24.9 mmol, 2.92 mL, 10.0 eq). The mixture was stirred at 80° C. under N₂ atmosphere for 12 h. To the mixture was added water (10 mL) and ethyl acetate (20 mL). The two phases were separated and the aqueous phase was extracted with ethyl acetate (3×20 mL). The organic phases were combined, dried over anhydrous Na₂SO₄, filtered and concentrated. To the residue was added petroleum (20 mL) and ethyl actetate (3 mL). The mixture was stirred at 15° C. for 30 min. During this time a pink solid precipitated. The solid was filtered and further purified via prep-HPLC to give compound 67 (520 mg, 1.31 mmol, 52% yield) as a yellow solid.

¹H NMR (400 MHz, DMSO-d₆) δ=7.30-7.16 (m, 6H), 7.01 (s, 1H), 6.40 (br. s., 2H), 5.85 (s, 2H).

General Procedure for Preparation of Compound 68:

To the solution of 67 (300 mg, 755 umol, 1.00 eq) in HOAc (4.20 mL) and H₂O (1.40 mL) was added 1,3-dichloro-5,5-dimethylhydantoin (297 mg, 1.51 mmol, 2.00 eq) at 0-5° C. The mixture was stirred at 0-5° C. for 1 h, and then stirred at 20° C. for 3 h. The reaction mixture was used in the next step directly without purification.

General Procedure for Preparation of Compound 20:

To a solution of NH₃ (1.03 g, 60.4 mmol, 80.0 eq) in THF (6.00 mL) was added dropwise the solution of 68 (282 mg, 755 umol, 1.00 eq) in HOAc (4.20 mL) and H₂O (1.40 mL) at 0° C. The mixture was stirred at 20° C. for 12 h. To the mixture was added ethyl acetate (15 mL) and water (6 mL). The two phases were separated and the aqueous phase was extracted with ethyl acetate (2×10 mL). The organic phases were combined and concentrated. The residue was purified via prep-HPLC to, give 20 (92.0 mg, 259 umol, 34% yield, 99.7% purity) as a white solid.

¹H NMR (400 MHz, DMSO-d₆) δ=7.45 (s, 1H), 7.27 (s, 3H), 6.52 (br. s., 2H), 5.94 (s, 2H), 3.97 (s, 3H), 3.51 (td, J=6.6, 13.5 Hz, 1H), 1.26 (d, J=6.6 Hz, 6H.

LCMS: 99.7% purity, m/z=355.0 (M+1).

Example 23

Synthesis of Compound 21

Compound 21 was made by the synthetic method outlined in Scheme 4:

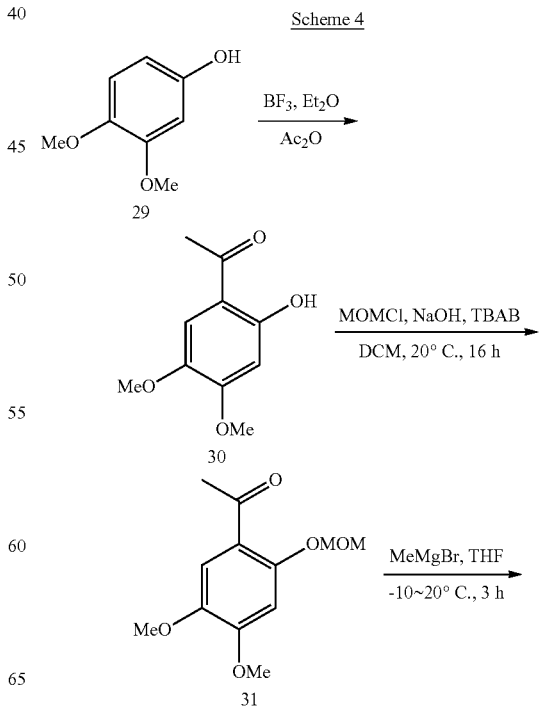

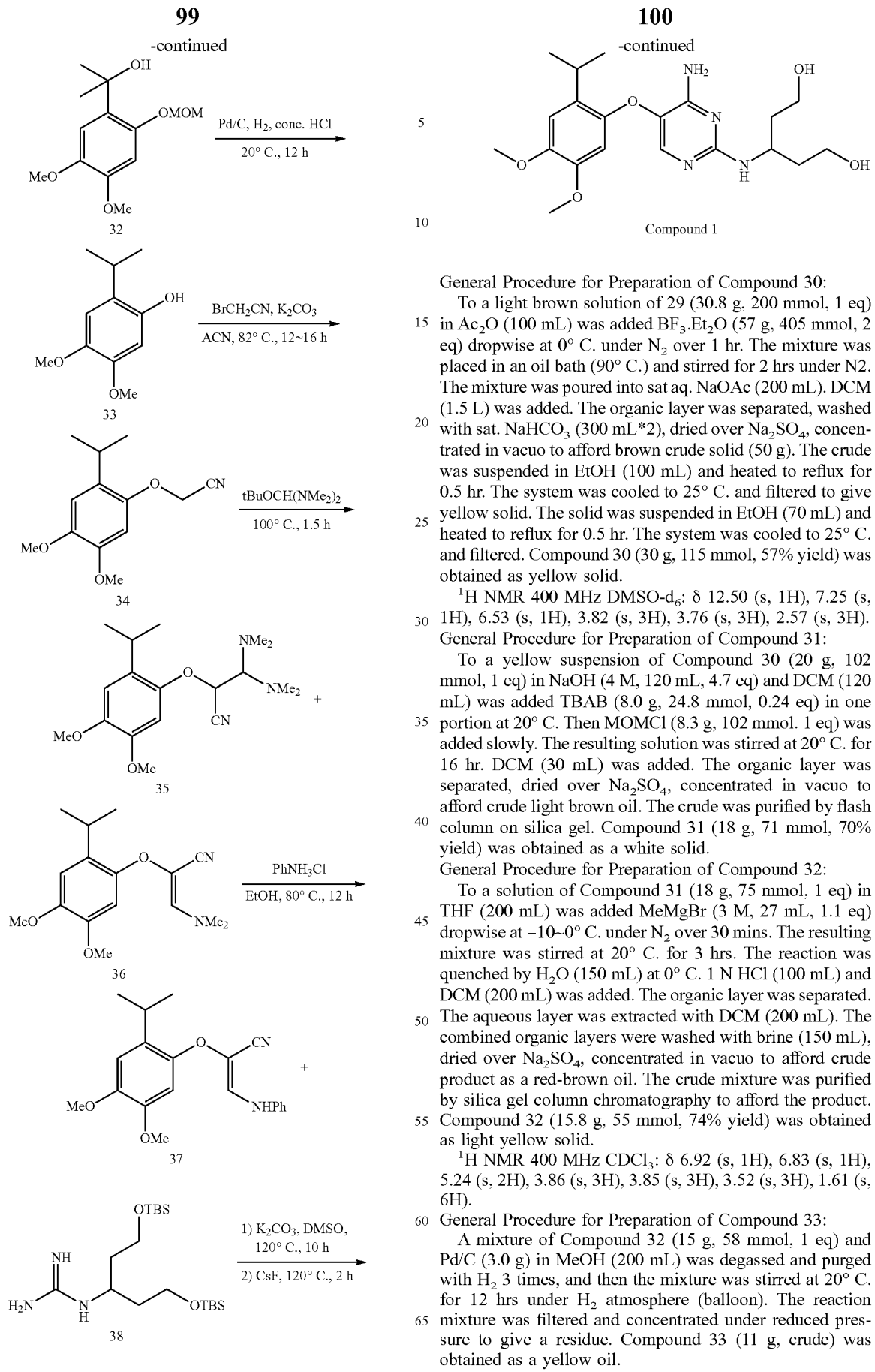

Compound 1

General Procedure for Preparation of Compound 30:
To a light brown solution of 29 (30.8 g, 200 mmol, 1 eq) in Ac$_2$O (100 mL) was added BF$_3$.Et$_2$O (57 g, 405 mmol, 2 eq) dropwise at 0° C. under N$_2$ over 1 hr. The mixture was placed in an oil bath (90° C.) and stirred for 2 hrs under N2. The mixture was poured into sat aq. NaOAc (200 mL). DCM (1.5 L) was added. The organic layer was separated, washed with sat. NaHCO$_3$ (300 mL*2), dried over Na$_2$SO$_4$, concentrated in vacuo to afford brown crude solid (50 g). The crude was suspended in EtOH (100 mL) and heated to reflux for 0.5 hr. The system was cooled to 25° C. and filtered to give yellow solid. The solid was suspended in EtOH (70 mL) and heated to reflux for 0.5 hr. The system was cooled to 25° C. and filtered. Compound 30 (30 g, 115 mmol, 57% yield) was obtained as yellow solid.

$^1$H NMR 400 MHz DMSO-d$_6$: δ 12.50 (s, 1H), 7.25 (s, 1H), 6.53 (s, 1H), 3.82 (s, 3H), 3.76 (s, 3H), 2.57 (s, 3H).

General Procedure for Preparation of Compound 31:
To a yellow suspension of Compound 30 (20 g, 102 mmol, 1 eq) in NaOH (4 M, 120 mL, 4.7 eq) and DCM (120 mL) was added TBAB (8.0 g, 24.8 mmol, 0.24 eq) in one portion at 20° C. Then MOMCl (8.3 g, 102 mmol. 1 eq) was added slowly. The resulting solution was stirred at 20° C. for 16 hr. DCM (30 mL) was added. The organic layer was separated, dried over Na$_2$SO$_4$, concentrated in vacuo to afford crude light brown oil. The crude was purified by flash column on silica gel. Compound 31 (18 g, 71 mmol, 70% yield) was obtained as a white solid.

General Procedure for Preparation of Compound 32:
To a solution of Compound 31 (18 g, 75 mmol, 1 eq) in THF (200 mL) was added MeMgBr (3 M, 27 mL, 1.1 eq) dropwise at –10~0° C. under N$_2$ over 30 mins. The resulting mixture was stirred at 20° C. for 3 hrs. The reaction was quenched by H$_2$O (150 mL) at 0° C. 1 N HCl (100 mL) and DCM (200 mL) was added. The organic layer was separated. The aqueous layer was extracted with DCM (200 mL). The combined organic layers were washed with brine (150 mL), dried over Na$_2$SO$_4$, concentrated in vacuo to afford crude product as a red-brown oil. The crude mixture was purified by silica gel column chromatography to afford the product. Compound 32 (15.8 g, 55 mmol, 74% yield) was obtained as light yellow solid.

$^1$H NMR 400 MHz CDCl$_3$: δ 6.92 (s, 1H), 6.83 (s, 1H), 5.24 (s, 2H), 3.86 (s, 3H), 3.85 (s, 3H), 3.52 (s, 3H), 1.61 (s, 6H).

General Procedure for Preparation of Compound 33:
A mixture of Compound 32 (15 g, 58 mmol, 1 eq) and Pd/C (3.0 g) in MeOH (200 mL) was degassed and purged with H$_2$ 3 times, and then the mixture was stirred at 20° C. for 12 hrs under H$_2$ atmosphere (balloon). The reaction mixture was filtered and concentrated under reduced pressure to give a residue. Compound 33 (11 g, crude) was obtained as a yellow oil.

General Procedure for Preparation of Compound 34:

A mixture of Compound 33 (12.6 g, 64 mmol, 1 eq), 2-bromoacetonitrile (23 g, 193 mmol, 3 eq) and $K_2CO_3$ (26.6 g, 193 mmol, 3 eq) in ACN (150 mL) was stirred at reflux (82° C.) for 16 hrs. The mixture was cooled and filtered. The filtrate was concentrated in vacuo to afford the crude. The crude was purified by silica gel column to afford the product. Compound 33 (10.8 g, 46 mmol, 71% yield) was obtained as light grey solid.

$^1$H NMR 400 MHz $CDCl_3$: δ 6.77 (s, 1H), 6.59 (s, 1H), 4.72 (s, 2H), 3.87 (s, 6H), 3.30-3.20 (m, 1H), 1.21 (d, J=6.8 Hz, 6H).

General Procedure for Preparation of Compound 35 and 36:

A mixture of Compound 33 (10.8 g, 45.9 mmol, 1 eq) and t-BuOCH(NMe$_2$)$_2$ (16 g, 91.8 mmol, 2 eq) was heated to 100° C. for 1.5 hrs under $N_2$. The mixture was concentrated in oil pump to afford the crude mixture of Compound 35 and Compound 36 as a brown solid, which was used without purification.

General Procedure for Preparation of Compound 37:

The solution of aniline (20.1 g, 155 mmol, 3.00 eq, HCl) in EtOH (200 mL) was added to the crude mixture of Compound 35 and Compound 36 (15 g, 51.7 mmol, 1.00 eq). Then the reaction was stirred at 80° C. for 12 hrs. The reaction mixture was concentrated to dryness. Ethyl acetate (600 mL) was added, and washed with $H_2O$ (200 mL). The organic layers were washed with brine and dried over $Na_2SO_4$, filtered, concentrated in vacuum. The crude product was purified by silica gel chromatography to give Compound 37 (7 g, 36% yield) as a brown solid.

General Procedure for Preparation of Compound 1:

A mixture of Compound 37 (180 mg, 532 umol, 1.00 eq) and Compound 38 (415 mg, 1.06 mmol, 2.00 eq. Synthesis described below) and $K_2CO_3$ (147 mg, 1.06 mmol, 2.00 eq) in DMSO (2 mL) was stirred at 120° C. for 10 hrs. CsF (80.8 mg, 532 umol, 1.00 eq) was then added to the mixture. The reaction was stirred at 120° C. for an additional 2 hrs. The reaction was cooled, and the crude product was purified by prep-HPLC to afford Compound 1 (18 mg, 8% yield) as a yellow oil.

$^1$H NMR 400 MHz MeOD, δ 6.94 (s, 1H), 6.80 (s, 1H), 6.72 (s, 1H), 3.85 (s, 3H), 3.79 (s, 3H), 3.68-3.65 (m, 5H), 3.11-3.04 (m, 1H), 1.89-1.83 (m, 2H), 1.79-1.76 (m, 2H), 1.22 (d, J=7.2 Hz, 6H).

MS: [M+H] 407.3

Example 24

Synthesis of Compound 2

Compound 2 was made by the synthetic method outlined in Scheme 5:

Scheme 5

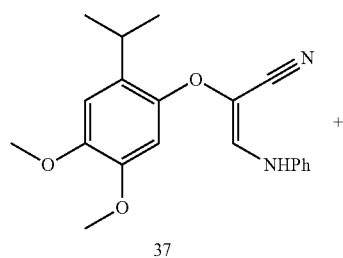

37

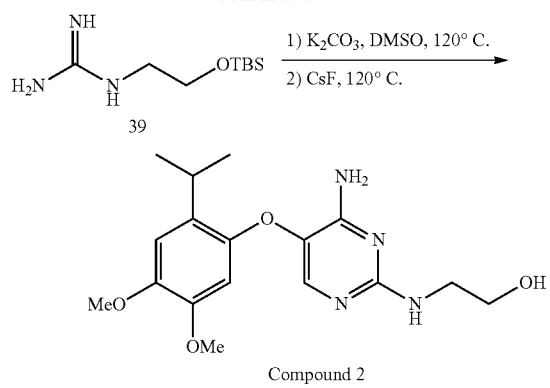

Compound 2

Compound 37 was prepared as outlined above in Example 1.

General Procedure for Preparation of Compound 2:

To a mixture of Compound 37 (300 mg, 887 umol, 1.00 eq) and $K_2CO_3$ (245 mg, 1.77 mmol, 2.00 eq) in DMSO (3 mL) was added Compound 39 (385 mg, 1.77 mmol, 2.00 eq). The reaction was stirred at 120° C. for 10 hrs. The mixture was cooled and CsF (30 mg, 198 umol, 0.22 eq) was added. The reaction was heated and stirred at 120° C. for 2 hrs. The reaction was cooled, and the crude product purified by prep-HPLC purification to give Compound 2 (78 mg, 24% yield) as a light yellow solid.

$^1$H NMR 400 MHz $CDCl_3$: δ 7.41 (s, 1H), 6.80 (s, 1H), 6.41 (s, 1H), 5.14-5.12 (m, 1H), 4.99 (s, 2H), 3.89 (s, 3H), 3.81-3.79 (m, 2H), 3.78 (s, 3H), 3.53-3.49 (m, 2H), 3.28-3.23 (m, 1H), 1.24 (d, J=6.8 Hz, 6H).

MS: [M+H] 349.2

Example 25

Synthesis of Compound 3

Compound 3 was made by the synthetic method outlined in Scheme 6:

Scheme 6

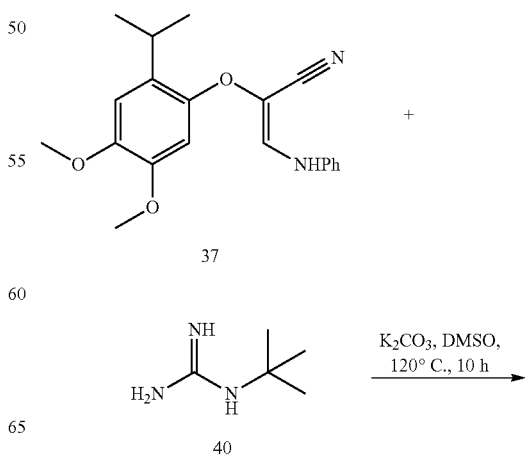

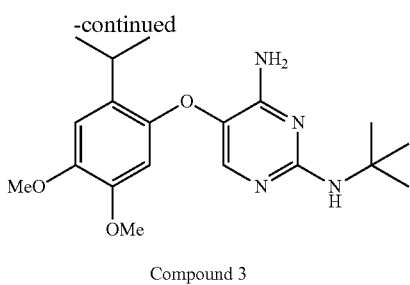

Compound 3

Compound 37 was prepared as outlined above in Example 1.

General Procedure for Preparation of Compound 3:

To a mixture of Compound 37 (200 mg, 591 umol, 1.00 eq) and K$_2$CO$_3$ (163 mg, 1.18 mmol, 2.00 eq) in DMSO (2 mL) was added Compound 40 (136 mg, 1.18 mmol, 2.00 eq). The reaction was stirred at 120° C. for 10 hrs. The crude product was purified by prep-HPLC to give Compound 3 (53.8 mg, 24% yield) as a light yellow solid.

$^1$H NMR 400 MHz CDCl$_3$: δ 7.47 (s, 1H), 6.80 (s, 1H), 6.42 (s, 1H), 4.81-4.75 (m, 3H), 3.89 (s, 3H), 3.77 (s, 3H), 3.30-3.25 (m, 1H), 1.42 (s, 9H), 1.25 (d, J=7.2 Hz, 6H).

MS: [M+H] 361.2

Example 26

Synthesis of Compound 4

Compound 4 was made by the synthetic method outlined in Scheme 7:

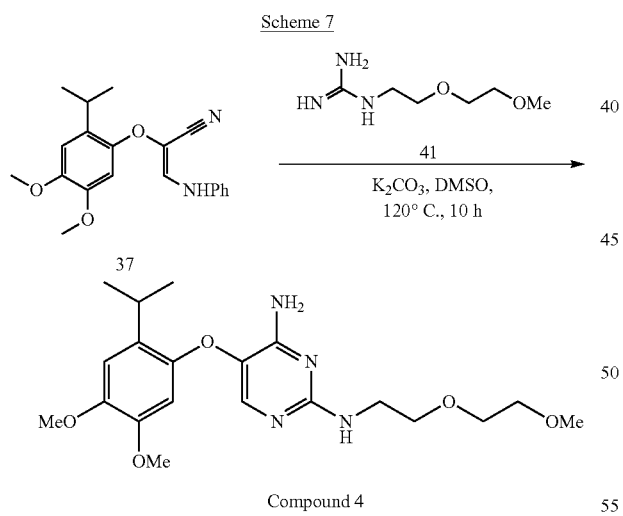

Compound 37 was prepared as outlined above in Example 1.

General Procedure for Preparation of Compound 4:

The mixture of Compound 37 (200 mg, 591 umol, 1.00 eq) and K$_2$CO$_3$ (163 mg, 1.18 mmol, 2.00 eq) in DMSO (2 mL) was added Compound 41 (191 mg, 1.18 mmol, 2.00 eq). The reaction was stirred at 120° C. for 10 hrs. The reaction was cooled, and the crude product was purified by prep-HPLC to give Compound 4 (76.9 mg, 31% yield) as a brown solid.

$^1$H NMR 400 MHz CDCl$_3$: δ 7.50 (s, 1H), 6.79 (s, 1H), 6.39 (s, 1H), 5.38-5.35 (m, 1H), 4.95 (s, 2H), 3.88 (s, 3H), 3.75 (s, 3H), 3.67-3.62 (m, 4H), 3.58-3.54 (m, 4H), 3.39 (s, 3H), 3.30-3.25 (m, 1H), 1.25 (d, J=6.8 Hz, 6H).

MS: [M+H] 407.2

Example 27

Synthesis of Compound 5

Compound 5 was made by the synthetic method outlined in Scheme 8:

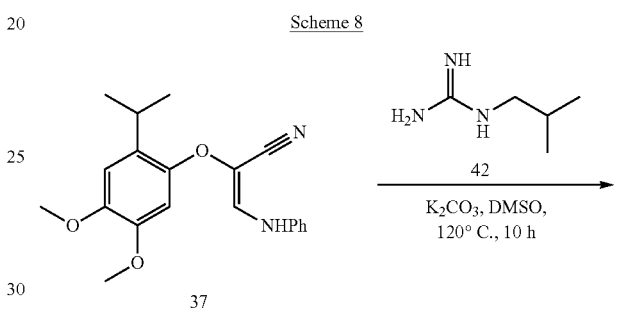

Compound 5

Compound 37 was prepared as outlined above in Example 1.

General Procedure for Preparation of Compound 5:

The mixture of Compound 37 (200 mg, 591 umol, 1.00 eq) and K$_2$CO$_3$ (163 mg, 1.18 mmol, 2.00 eq) in DMSO (2 mL) was added Compound 42 (136 mg, 1.18 mmol, 2.00 eq). The reaction was stirred at 120° C. for 10 hrs. The reaction was cooled and the crude product was purified by prep-HPLC purification to give Compound 5 (62.4 mg, 28% yield) as a light yellow solid.

$^1$H NMR 400 MHz CDCl$_3$: δ 7.50 (s, 1H), 6.79 (s, 1H), 6.40 (s, 1H), 4.85 (s, 2H), 4.77-4.73 (m, 1H), 3.89 (s, 3H), 3.76 (s, 3H), 3.33-3.26 (m, 1H), 3.17 (t, J=6.0 Hz, 2H), 1.89-1.83 (m, 1H), 1.25 (d, J=6.8 Hz, 6H), 0.97 (d, J=6.4 Hz, 6H).

MS: [M+H] 361.2

Example 28

Synthesis of Compound 6

Compound 6 was made by the synthetic method outlined in Scheme 9:

Scheme 9

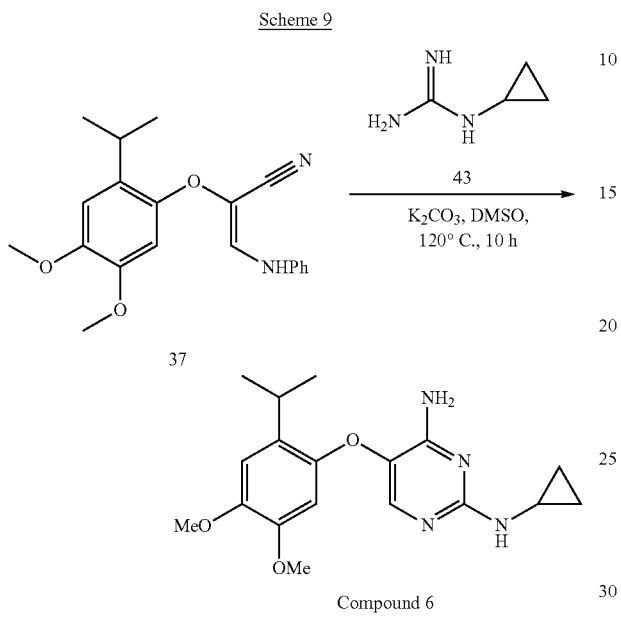

Compound 37 was prepared as outlined above in Example 1.
General Procedure for Preparation of Compound 6:
To a mixture of Compound 37 (200 mg, 591 umol, 1.00 eq) and K₂CO₃ (163 mg, 1.18 mmol, 2.00 eq) in DMSO (2 mL) was added Compound 43 (117 mg, 1.18 mmol, 2.00 eq). Then the reaction was stirred at 120° C. for 10 hrs. The reaction was cooled and the crude product was purified by prep-HPLC to give Compound 6 (25.1 mg, 12% yield) as a light yellow solid.
$^1$H NMR 400 MHz CDCl₃: δ 7.54 (s, 1H), 6.80 (s, 1H), 6.41 (s, 1H), 4.96-4.92 (m, 3H), 3.89 (s, 3H), 3.76 (s, 3H), 3.31-3.24 (m, 1H), 2.73-2.69 (m, 1H), 1.25 (d, J=7.2 Hz, 6H), 0.80-0.76 (m, 2H), 0.55-0.51 (m, 2H).
MS: [M+H] 345.3

Example 29

Synthesis of Compound 7

Compound 7 was made by the synthetic method outlined in Scheme 10:

Scheme 10

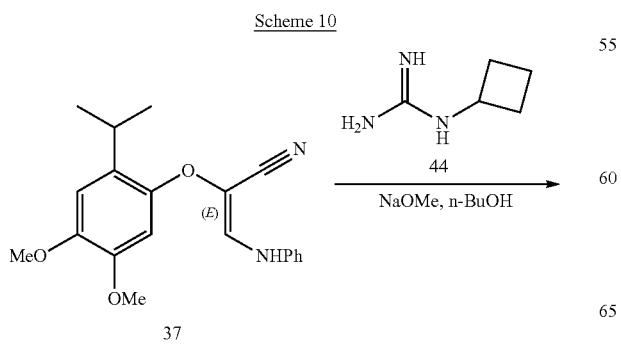

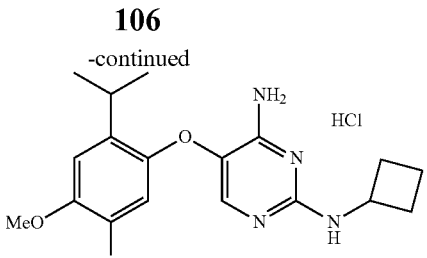

Compound 7

Compound 37 was prepared as outlined above in Example 1.
General Procedure for Preparation of Compound 7:
A mixture of Compound 37 (200 mg, 591 umol, 1 eq), 1-cyclobutylguanidine (Compound 44, 130 mg, 1.1 mmol, 1.9 eq) and NaOMe (40 mg, 738 umol, 1.25 eq) in n-BuOH (8 mL) was stirred at 120° C. for 12 hrs. The reaction was cooled, and solvent was removed in vacuo to afford a crude mixture. The mixture was purified by prep-HPLC (TFA) and prep-HPLC (HCl). Compound 7 (7 mg, 17 umol, 3% yield) was obtained as light brown gum as the HCl salt.
$^1$H NMR 400 MHz MeOD: δ 6.94 (s, 1H), 6.76 (s, 1H), 6.71 (s, 1H), 4.30 (br, 1H), 3.85 (s, 3H), 3.78 (s, 3H), 3.07-3.05 (m, 1H), 2.40-2.37 (m, 2H), 2.03-2.00 (m, 2H), 1.80-1.78 (m, 2H), 1.21 (d, J=6.8 Hz, 6H).
MS: [M+H] 359.2

Example 30

Synthesis of Compound 8

Compound 8 was made by the synthetic method outlined in Scheme 11:

Scheme 11

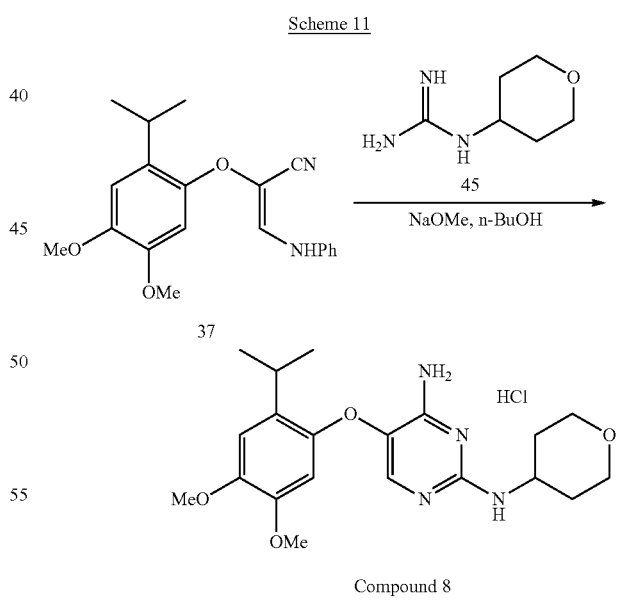

Compound 37 was prepared as outlined above in Example 1.
General Procedure for Preparation of Compound 8:
A mixture of Compound 37 (200 mg, 591 umol, 1 eq), 1-tetrahydropyran-4-ylguanidine (Compound 45, 170 mg, 1.2 mmol, 2 eq) and NaOMe (32 mg, 591 umol, 1 eq) in n-BuOH (8 mL) was stirred at 120° C. for 12 hrs. The reaction was cooled, and the solvent was removed in vacuo. The crude mixture was purified by prep-HPLC twice (TFA and HCl). Compound 8 (10.5 mg, 24 umol, 4% yield) was obtained as light brown gum.

$^1$H NMR 400 MHz MeOD: δ 6.94 (s, 1H), 6.80 (s, 1H), 6.72 (s, 1H), 4.01-3.95 (m, 3H), 3.85 (s, 3H), 3.78 (s, 3H), 3.53-3.50 (m, 2H), 3.09-3.05 (m, 1H), 2.00-1.99 (m, 2H), 1.65-1.55 (m, 2H), 1.21 (d, J=68 Hz, 6H).

MS: [M+H] 389.2

Example 31

Synthesis of Compound 9

Compound 9 was made by the synthetic method outlined in Scheme 13:

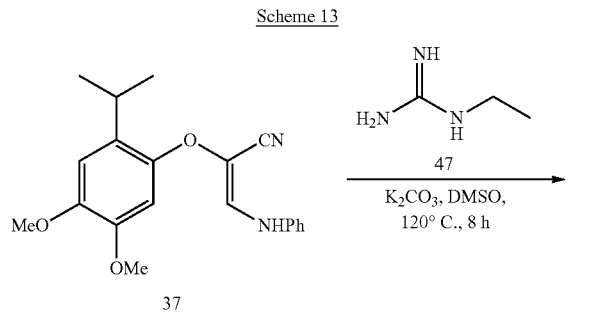

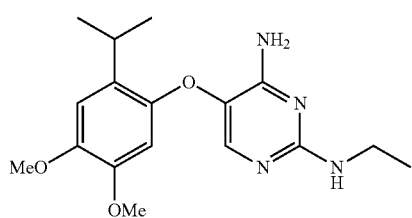

Compound 9

Compound 37 was prepared as outlined above in Example 1.

General Procedure for Preparation of Compound 9:

A mixture of Compound 37 (30 mg, 88.7 umol, 1.00 eq) and Compound 47 (21.9 mg, 177 umol, eq, HCl) and K$_2$CO$_3$ (24.5 mg, 177 umol, 2.00 eq) in DMSO (2 mL) was stirred at 120° C. for 8 hrs under N$_2$. The reaction mixture was concentrated to dryness. The crude product was purified by prep-HPLC purification to give Compound 9 (10 mg, 34% yield) as a brown solid.

$^1$H NMR 400 MHz CDCl$_3$: δ 7.52 (s, 1H), 6.80 (s, 1H), 6.40 (s, 1H), 4.85 (s, 2H), 4.66-4.64 (m, 1H), 3.89 (s, 3H), 3.75 (s, 3H), 3.41-3.34 (m, 2H), 3.31-3.26 (m, 1H), 1.26-1.20 (m, 9H).

MS: [M+H] 333.2

Example 32

Synthesis of Compound 10

Compound 10 was made by the synthetic method outlined in Scheme 14:

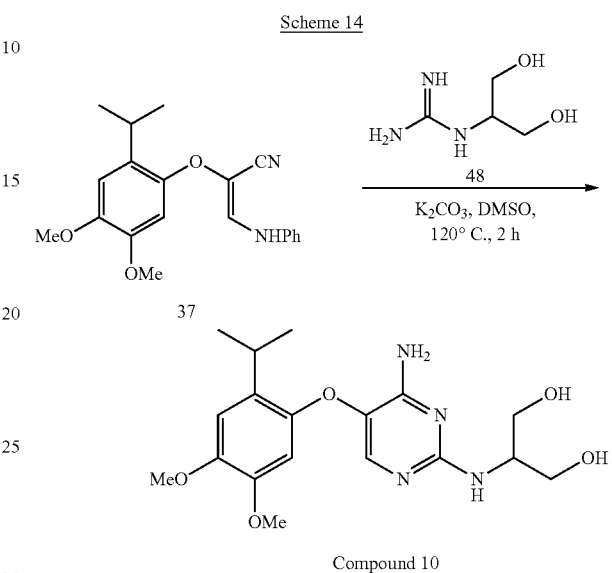

Compound 37 was prepared as outlined above in Example 1.

General Procedure for Preparation of Compound 10:

To a mixture of Compound 37 (300 mg, 887 umol, 1.00 eq) and K$_2$CO$_3$ (245 mg, 1.77 mmol, 2.00 eq) in DMSO (3 mL) was added Compound 48 (236 mg, 1.77 mmol, 2.00 eq). The mixture was stirred at 120° C. for 2 hrs. The reaction was cooled and the crude product was purified by prep-HPLC to afford Compound 10 (100 mg, 27% yield) as a yellow oil.

$^1$H NMR 400 MHz MeOD: δ 6.94 (s, 1H), 6.88 (s, 1H), 6.73 (s, 1H), 3.85 (s, 3H), 3.78 (s, 3H), 3.75-3.70 (m, 5H), 3.11-3.04 (m, 1H), 1.22 (d, J=6.8 Hz, 6H).

MS: [M+H] 379.2

Example 33

Synthesis of Compound 11

Compound 11 was made by the synthetic method outlined in Scheme 15:

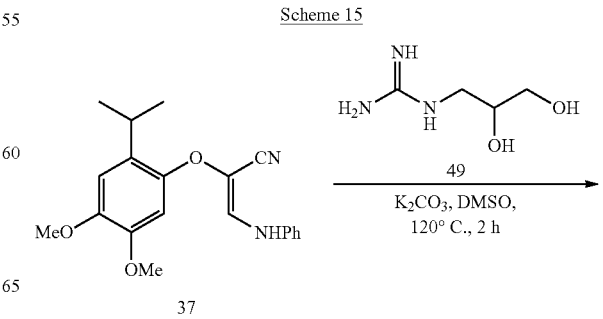

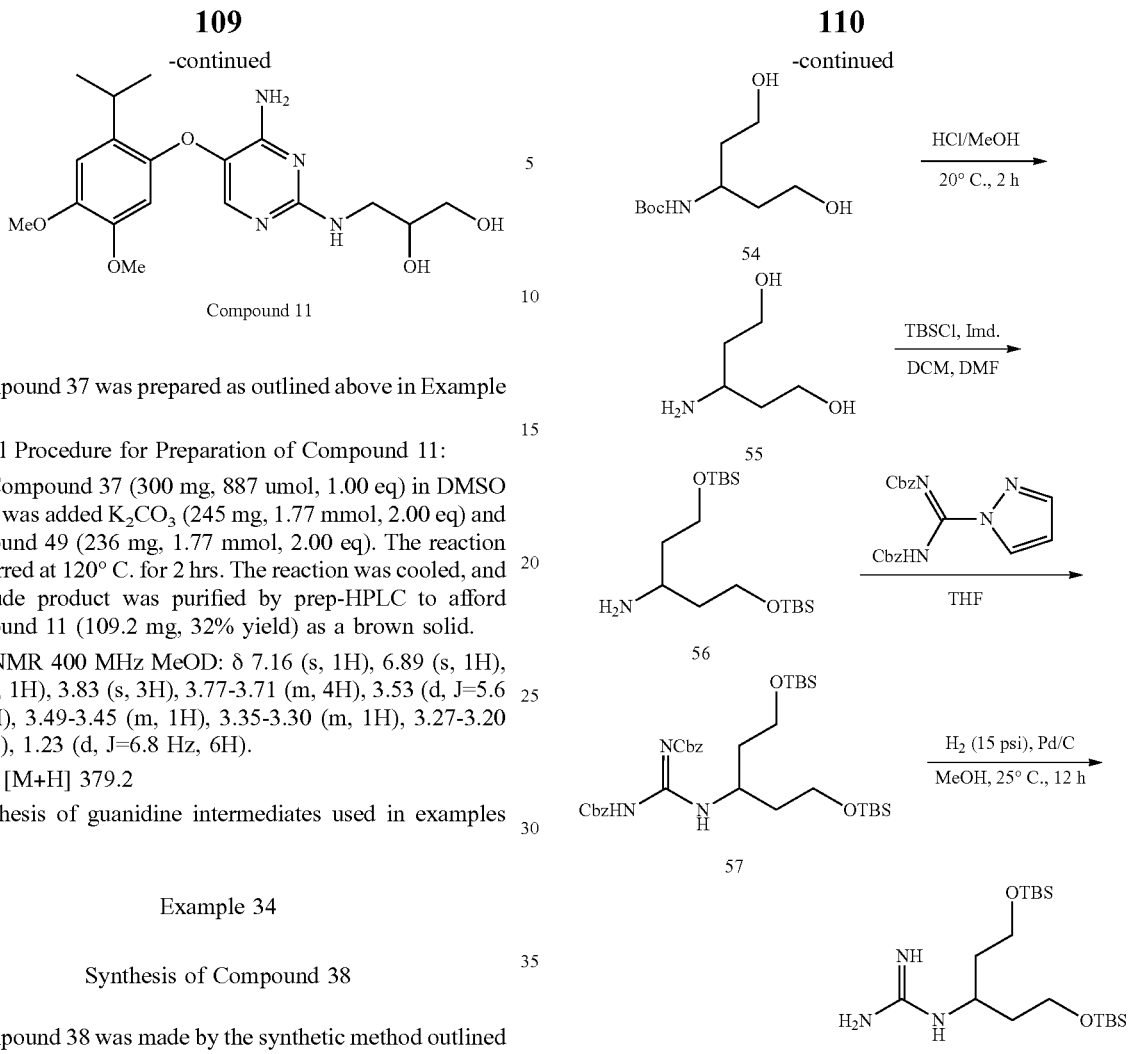

Compound 37 was prepared as outlined above in Example 1.

General Procedure for Preparation of Compound 11:

To Compound 37 (300 mg, 887 umol, 1.00 eq) in DMSO (4 mL) was added $K_2CO_3$ (245 mg, 1.77 mmol, 2.00 eq) and Compound 49 (236 mg, 1.77 mmol, 2.00 eq). The reaction was stirred at 120° C. for 2 hrs. The reaction was cooled, and the crude product was purified by prep-HPLC to afford Compound 11 (109.2 mg, 32% yield) as a brown solid.

$^1$H NMR 400 MHz MeOD: δ 7.16 (s, 1H), 6.89 (s, 1H), 6.49 (s, 1H), 3.83 (s, 3H), 3.77-3.71 (m, 4H), 3.53 (d, J=5.6 Hz, 2H), 3.49-3.45 (m, 1H), 3.35-3.30 (m, 1H), 3.27-3.20 (m, 1H), 1.23 (d, J=6.8 Hz, 6H).

MS: [M+H] 379.2

Synthesis of guanidine intermediates used in examples 27-38:

Example 34

Synthesis of Compound 38

Compound 38 was made by the synthetic method outlined in Scheme 16:

General Procedure for Preparation of Compound 51:

A mixture of Compound 50 (24.55 g, 140.97 mmol, 1.00 eq) and $NH_4HCO_3$ (23 g, 291 mmol, 2.1 eq) in MeOH (100 mL) was stirred at 20° C. for 40 hrs. The solvent was then removed in vacuo. The residue was azeotropical distilled with i-PrOH (100 mL*2) in vacuo to afford the product. Compound 51 (25 g, crude) was obtained as light yellow oil.

$^1$H NMR 400 MHz $CDCl_3$: δ 7.70 (br. s, 1H), 7.05 (br. s, 1H), 4.39 (s, 1H), 3.62 (s, 3H), 3.50 (s, 3H), 3.19 (s, 2H).

General Procedure for Preparation of Compound 52:

$H_2SO_4$ (28.7 g, 293 mmol, 2 eq) was added over 15 min to i-PrOH (85 mL) at 0~5° C. This solution was added over 30 mins to a solution of t-$BuNH_2 \cdot BH_3$ (12.5 g, 144 mmol, 1 eq) in THF (100 mL) keeping the temperature below −5° C. Then Compound 51 (25 g, 144 mmol, 1 eq) was added at 0° C. over 15 mins. The resulting mixture was allowed warm to 20° C. while stirring overnight (16 hrs). The reaction was quenched with $H_2O$ (150 mL) at 0~10° C. Then the pH value was adjusted to 9 by 5 N NaOH. DCM (200 mL) was added. The organic layer was separated. The aqueous layer was extracted with DCM (100 mL*3). The organic layer was combined and washed with brine (200 mL*3), dried over $Na_2SO_4$, and concentrated in vacuo to afford the crude Compound 52 (14.5 g, 74 mmol, 51% yield) as a light brown oil.

$^1$H NMR 400 MHz CDCl$_3$: δ 3.69 (s, 6H), 3.66-3.60 (m, 1H), 2.54-2.49 (m, 2H), 2.43-2.39 (m, 2H).

General Procedure for Preparation of Compound 53:

To a solution of Compound 52 (11.3 g, 58 mmol, 1 eq) and TEA (14.7 g, 145 mmol, 2.5 eq) in DCM (100 mL) was added Boc$_2$O (15.2 g, 70 mmol, 1.2 eq) portionwise at 20° C. The resulting mixture was stirred at 20° C. for 4 hrs. The reaction mixture was washed with 1 N HCl (25 mL*2) and H$_2$O (25 mL), dried over Na$_2$SO$_4$, concentrated in vacuo to afford the crude product. The crude was purified by column to give Compound 53 (12.9 g, 44.5 mmol, 76% yield) as a white solid.

$^1$H NMR 400 MHz CDCl$_3$: δ 5.33-5.30 (m, 1H), 4.31 (br, 1H), 3.69 (s, 6H), 2.72-2.61 (m, 4H), 1.43 (s, 9H).

General Procedure for Preparation of Compound 54:

To a solution of Compound 53 (5.0 g, 18 mmol, 1 eq) in EtOH (50 mL) was added NaBH$_4$ (2.7 g, 72 mmol, 4 eq) at 55° C. portionwise. The resulting mixture was stirred at this temperature for 5 hrs. The solvent was removed in vacuo. The residue was purified by silica gel column. Compound 54 (3.1 g, 14 mmol, 78% yield) was obtained as a colorless oil.

General Procedure for Preparation of Compound 55:

A solution of Compound 54 (3.1 g, 14 mmol, 1 eq) in HCl/MeOH (4 N, 30 mL) was stirred at 20° C. for 2 hrs. The solvent was removed in vacuo to afford the product. Compound 55 (2.25 g, 13.7 mmol, 97% yield) was obtained as colorless oil.

$^1$H NMR 400 MHz MeOD: δ 3.82-3.70 (m, 4H), 3.54-3.51 (m, 1H), 1.93-1.80 (m, 4H).

General Procedure for Preparation of Compound 56:

To a solution of Compound 55 (500 mg, 3.2 mmol, 1 eq) and imidazole (874 mg, 13 mmol, 4 eq) in DCM (15 mL) and DMF (5 mL) was added TBSCl (1.21 g, 8.0 mmol, 2.5 eq) at 20° C. The resulting mixture was stirred at 20° C. for 12 hrs. A new major spot formed. The mixture was diluted with DCM (20 mL), then washed with brine (15 mL*3), dried over Na$_2$SO$_4$, and concentrated in vacuo to afford Compound 56 (1.09 g, 2.8 mmol, 88% yield) as a light yellow oil.

$^1$H NMR 400 MHz CDCl$_3$: δ 5.30 (br, 2H), 3.84-3.72 (m, 4H), 3.39-3.35 (m, 1H), 1.83-1.80 (m, 4H), 0.88 (s, 18H), 0.06 (s, 12H).

General Procedure for Preparation of Compound 57:

A solution of Compound 56 (1.09 g, 2.8 mmol, 1 eq) and N,N-di-CBZ-1H-pyrazole-1-carbamidine (1.12 g, 3.0 mmol, 1.05 eq) in THF (15 mL) was stirred at 10° C. for 12 hrs. The solvent was removed in vacuo. The crude was purified by silica column chromatography to give the Compound 57 (640 mg, 972 umol, 34% yield) as a light yellow oil.

General Procedure for Preparation of Compound 38:

To a solution of compound 57 (640 mg, 1 mmol) in methanol (50 mL) was added Pd/C (100 mg) at 25° C. under H$_2$ (15 psi). The reaction was stirred for 12 hrs at 25° C. The mixture was filtered thought Bucher funnel and the filtrate was concentrated in vacuo to obtain compound 38 (400 mg, crude) as white solid, which was used directly.

$^1$H NMR 400 MHz MeOD: δ 3.88-3.70 (m, 5H), 1.86-1.62 (m, 4H), 0.92 (s, 18H), 0.10 (s, 12H).

Example 35

Synthesis of Compound 39

Compound 39 was made by the synthetic method outlined in Scheme 17:

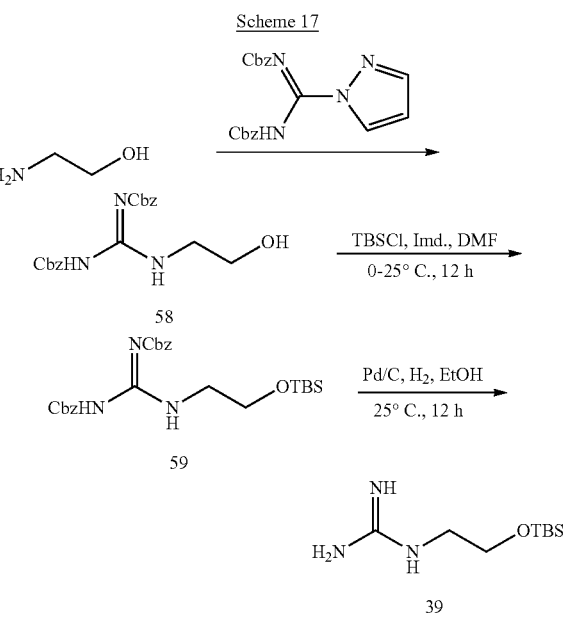

General Procedure for Preparation of Compound 58:

To a solution of ethanoloamine (180 mg, 7.9 mmol, 1.00 eq) was added and N,N-di-CBZ-1H-pyrazole-1-carbamidine (3.0 g, 7.9 mmol, 1.00 eq) at 15° C. The mixture was stirred at 15° C. for 16 hrs. The reaction mixture was concentrated in vacuo. The crude was purified by silica gel column chromatography to give Compound 58 (2.1 g) as a white solid.

$^1$H NMR 400 MHz CDCl$_3$: δ 11.75 (s, 1H), 8.70 (s, 1H), 7.39-7.28 (m, 10H), 5.21 (s, 2H), 5.14 (s, 2H), 3.80-3.77 (m, 2H), 3.63-3.59 (m, 2H).

General Procedure for Preparation of Compound 59:

To a solution of Compound 58 (1.90 g, 5.1 mmol, 1.0 eq) in DCM (20 mL) was added imidazole (1.05 g, 15 mmol, 3.0 eq) and TBSCl (1.16 g, 7.6 mmol, 1.50 eq) at 0° C. The mixture was stirred at 0-25° C. for 12 hrs. The reaction mixture was quenched by addition H$_2$O (20 mL) at 25° C., and then diluted with ethyl acetate (20 mL) and extracted with ethyl acetate (20 mL*3). The combined organic layers were dried over Na$_2$SO$_4$, filtered and concentrated under reduced pressure to give a residue. The residue was purified by prep-TLC to obtain Compound 59 (2.20 g, 4.08 mmol, 79% yield) as a colorless oil.

$^1$H NMR 400 MHz CDCl$_3$: δ 7.33-7.19 (m, 10H), 5.11 (s, 2H), 5.06 (s, 2H), 3.67-3.64 (m, 2H), 3.52-3.48 (m, 2H), 0.85 (s, 9H), 0.00 (s, 6H).

General Procedure for Preparation of Compound 39:

A mixture of Compound 59 (2.0 g, 4.12 mmol, 1.0 eq) and Pd/C (1.0 g) in EtOH (20 mL) was degassed and purged with H$_2$ 3 times, and then the mixture was stirred at 25° C. for 12 hrs under H$_2$ (15 psi). The reaction mixture was filtered. The filtrate was concentrated under reduced pressure to give Compound 39 (896 mg, crude) as a white solid.

$^1$H NMR 400 MHz CDCl$_3$: δ 3.73-3.71 (m, 2H), 3.31-3.26 (m, 2H), 0.88 (s, 9H), 0.06 (s, 6H).

Example 36

Synthesis of Compound 40

Compound 40 was made by the synthetic method outlined in Scheme 18:

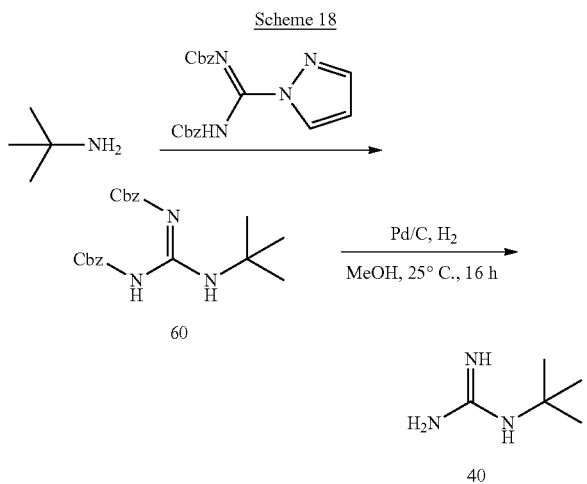

General Procedure for Preparation of Compound 60:

To a solution of tert-butylamine (638 mg, 8.72 mmol, 1.10 eq) was added N,N-di-CBZ-1H-pyrazole-1-carbamidine (3.0 g, 7.93 mmol, 1.00 eq) at 70° C. The mixture was stirred at 70° C. for 16 hrs. The reaction mixture was cooled and concentrated in vacuo. The residue was purified by silica gel column chromatography to give Compound 60 (2.2 g) as white solid.

$^1$H NMR 400 MHz CDCl$_3$: δ 11.84 (s, 1H), 8.36 (s, 1H), 7.43-7.28 (m, 10H), 5.19-5.18 (2s, 4H), 1.47 (s, 9H).

General Procedure for Preparation of Compound 40:

To a solution of compound 60 (2.00 g, 5.22 mmol) in MeOH (5.00 mL) was added Pd/C (25.0 mg) at 25° C. under H$_2$ balloon, the reaction was stirred at 25° C. for 16 h. The reaction was filtered and concentrated in vacuum to afford compound 40 (900 mg, crude) as white solid which was used without further purification.

$^1$H NMR 400 MHz MeOD: δ 1.41 (s, 9H)

Example 37

Synthesis of Compound 41

Compound 41 was made by the synthetic method outlined in Scheme 19:

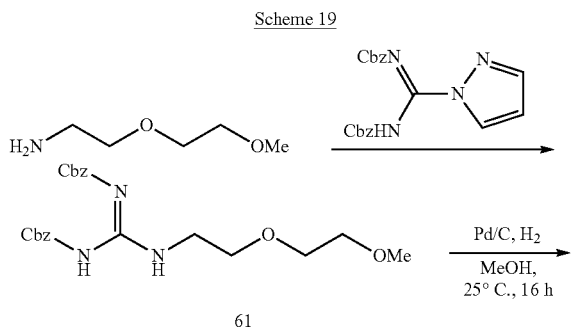

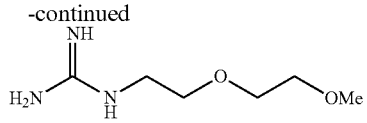

General Procedure for Preparation of Compound 61:

To a solution of 2-(2-methoxyethoxy)ethan-1-amine (1.04 g, 8.72 mmol, 1.10 eq) was added N,N-di-CBZ-1H-pyrazole-1-carbamidine (3.00 g, 7.93 mmol, 1.00 eq) at 15° C. The mixture was stirred at 15° C. for 16 hrs. The reaction mixture was concentrated in vacuo. The residue was purified by silica gel column, to give Compound 61 (2.2 g) as colorless oil.

$^1$H NMR 400 MHz CDCl$_3$: δ 11.74 (s, 1H), 8.65 (s, 1H), 7.42-7.28 (m, 10H), 5.20 (s, 2H), 5.14 (s, 2H), 3.68-3.64 (m, 6H), 3.59-3.58 (m, 2H), 3.41 (s, 3H).

General Procedure for Preparation of Compound 41:

To a solution of compound Compound 61 (1.00 g, 2.33 mmol) in MeOH (5.00 mL) was added Pd/C (3.39 mg) at 25° C. under H$_2$ balloon, the reaction was stirred at 25° C. under H$_2$ (15 psi) for 16 h. The reaction was filtered and concentrated in vacuum to afford Compound 41 (300 mg, 71% yield) as a yellow oil which was used directly without further purification.

MS: [M+H] 162.1

Example 38

Synthesis of Compound 42

Compound 42 was made by the synthetic method outlined in Scheme 20:

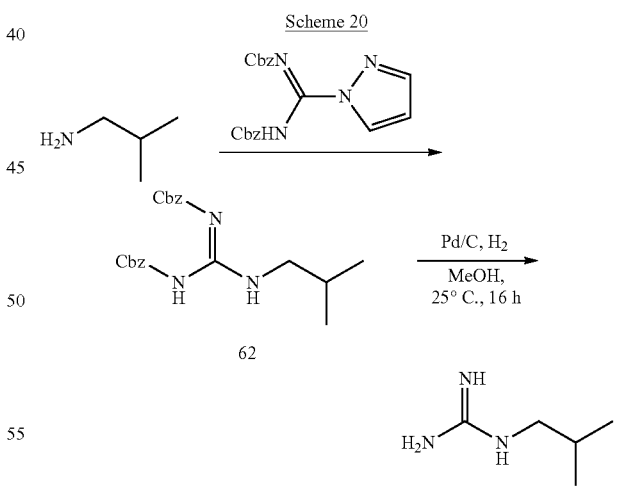

General Procedure for Preparation of Compound 62:

To a solution of isobutylamine (638 mg, 8.72 mmol, 1.10 eq) was added added N,N-di-CBZ-1H-pyrazole-1-carbamidine (3.00 g, 7.93 mmol, 1.00 eq) at 15° C. The mixture was stirred at 15° C. for 16 hrs. The residue was purified by silica gel column chromatography to give 62 (2.6 g) as a white solid.

115

$^1$H NMR 400 MHz CDCl$_3$: δ 11.80 (s, 1H), 8.42 (s, 1H), 7.43-7.28 (m, 10H), 5.21 (s, 2H), 5.16 (s, 2H), 3.31-3.28 (m, 2H), 1.93-1.84 (m, 1H), 0.99 (d, J=6.4 Hz, 6H).

General Procedure for Preparation of Compound 42:

To a solution of compound 62 (1.00 g, 2.61 mmol) in MeOH (5.00 mL) was added Pd/C (100 mg) at 25° C. under H$_2$ balloon, the reaction was stirred at 25° C. under H$_2$ (15 psi) for 16 h. The reaction was filtered and concentrated in vacuum to afford compound 42 (300 mg, 89% yield) as a yellow oil that was used without further purification.

$^1$H NMR 400 MHz MeOD: δ 2.98 (d, J=8.0 Hz, 2H), 1.81-1.58 (m, 1H), 0.96 (d, J=8.0 Hz, 6H).

MS: [M+H] 116.2

Example 39

Synthesis of Compound 43

Compound 43 was made by the synthetic method outlined in Scheme 21:

Scheme 21

General Procedure for Preparation of Compound 63:

To a solution of cyclopropylamine (498 mg, 8.72 mmol, 1.10 eq) was added added N,N-di-CBZ-1H-pyrazole-1-carbamidine (3.00 g, 7.93 mmol, 1.00 eq) at 15° C. The mixture was stirred at 15° C. for 16 hrs. The residue was purified by silica gel column chromatography to give 62 (2.0 g) as a white solid.

$^1$H NMR 400 MHz CDCl$_3$: δ 11.74 (s, 1H), 8.65 (s, 1H), 7.42-7.28 (m, 10H), 5.20 (s, 2H), 5.14 (s, 2H), 3.68-3.58 (m, 8H), 3.41 (s, 3H).

General Procedure for Preparation of Compound 43:

To a solution of compound 63 (1.50 g, 3.93 mmol) in MeOH (5.00 mL) was added Pd/C (100 mg) at 25° C. under H$_2$ balloon, the reaction was stirred at 25° C. under H$_2$ (15 psi) for 16 h. The reaction was filtered and concentrated in vacuum to afford compound 43 (400 mg, 80% yield) as a yellow oil that was used without further purification.

$^1$H NMR MeOD, 400 MHz: δ 2.55-2.50 (M, 1H), 0.88 (d, J=4.0 Hz, 2H), 0.64 (s, 2H)

116

Example 40

Synthesis of Compound 44

Compound 44 was made by the synthetic method outlined in Scheme 22:

Scheme 22

General Procedure for Preparation of Compound 64:

To a solution of compound N,N-di-CBZ-1H-pyrazole-1-carbamidine (5.0 g, 13.2 mmol) in THF (20 mL) was added cyclobutylamine (1.1 g, 15.8 mmol) at 25° C. The reaction was stirred for 12 hrs at 25° C. The mixture was concentrated in vacuo to get a residue. The residue was purified by silica gel column to obtain compound 64 (2.5 g, 44% yield) as a white solid.

General Procedure for Preparation of Compound 44:

To a solution of compound 64 (1.0 g, 2.6 mmol) in methanol (50 mL) was added Pd/C (100 mg) at 25° C. under H$_2$ (15 psi). The reaction was stirred for 12 hrs at 25° C. The mixture was filtered thought Bucher funnel and the filtrate was concentrated in vacuo to obtain compound 44 (550 mg, crude) as a white solid, which was used without further purification.

$^1$H NMR 400 MHz DMSO-d$_6$: δ 7.85-7.50 (m, 4H), 4.05-3.85 (m, 1H), 2.75-2.25 (m, 2H), 1.90-1.86 (m, 2H), 1.71-1.55 (m, 2H).

Example 41

Synthesis of Compound 45

Compound 45 was made by the synthetic method outlined in Scheme 23:

Scheme 23

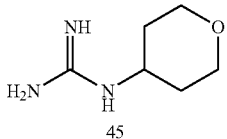

General Procedure for Preparation of Compound 65:

To a solution of N,N-di-CBZ-1H-pyrazole-1-carbamidine (3 g, 7.9 mmol) in THF (20 mL) was added tetrahydro-2H-pyran-4-amine (0.9 g, 9.5 mmol) at 25° C. The reaction was stirred for 12 hrs at 25° C. The mixture was concentrated in vacuo to give a residue. The residue was purified by silica gel column to obtain compound 65 (1.4 g, 38% yield) as a white solid.

General Procedure for Preparation of Compound 45:

To a solution of compound 65 (1.3 g, 3.16 mmol) in methanol (50 mL) was added Pd/C (100 mg) at 25° C. under H$_2$ (15 psi). The reaction was stirred for 12 hrs at 25° C. The mixture was filtered thought Bucher funnel and the filtrate was concentrated in vacuo to obtain compound 45 (700 mg, crude) as white solid, which was used without further purification.

$^1$H NMR 400 MHz DMSO-d$_6$: δ 7.70-7.60 (m, 4H), 3.84-3.82 (m, 2H), 3.60-3.52 (m, 1H), 3.43-3.30 (m, 2H), 1.78-1.75 (m, 2H), 1.43-1.35 (m, 2H).

Example 42

Synthesis of Compound 46

Compound 46 was made by the synthetic method outlined in Scheme 24:

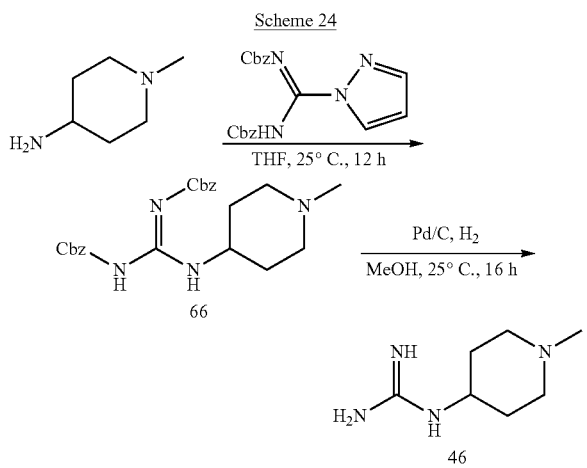

General Procedure for Preparation of Compound 66:

To a solution of N,N-di-CBZ-1H-pyrazole-1-carbamidine (3.0 g, 7.9 mmol) in THF (20 mL) was added 1-methylpiperidin-4-amine (1.1 g, 9.5 mmol) at 25° C. The reaction was stirred for 12 hrs at 25° C. The mixture was concentrated in vacuo to give a residue. The residue was purified by silica gel column chromatography to obtain compound 66 (2.0 g, 43% yield) as a white solid.

General Procedure for Preparation of Compound 46:

To a solution of Compound 66 (2.0 g, 4.7 mmol) in methanol (50 mL) was added Pd/C (200 mg) at 25° C. under H$_2$ (15 psi). The reaction was stirred for 12 hrs at 25° C. The mixture was filtered thought Bucher funnel and the filtrate was concentrated in vacuo to obtain compound 46 (1.0 g, crude) as a white solid, which was used directly without further purification.

$^1$H NMR 400 MHz DMSO-d$_6$: δ 7.96-7.67 (m, 4H), 3.70-3.65 (m, 1H), 3.54-3.49 (m, 2H), 2.87 (s, 3H), 2.32-2.27 (m, 2H), 2.13-2.11 (m, 2H), 1.78-1.75 (m, 2H).

Example 43

Synthesis of Compound 48

Compound 48 was made by the synthetic method outlined in Scheme 25:

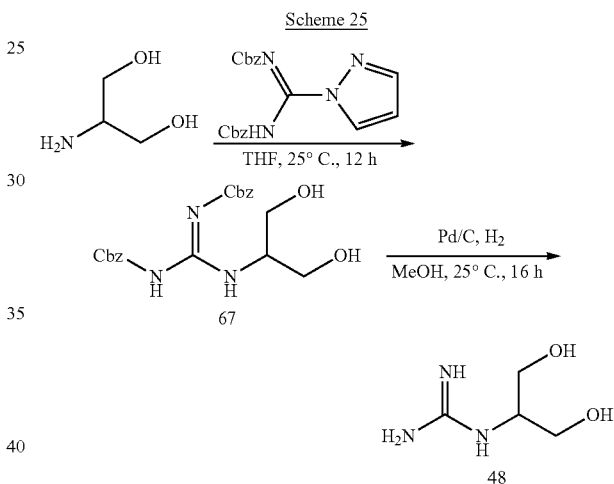

General Procedure for Preparation of Compound 67:

To a solution of 2-aminopropane-1,3-diol (3.00 g, 32.9 mmol, 1.00 eq) in THF (60 mL) was added N,N-di-CBZ-1H-pyrazole-1-carbamidine (11.2 g, 29.6 mmol, 0.90 eq). Then the reaction was stirred at 25° C. for 16 hrs and 75% Compound 67. The reaction mixture was concentrated to dryness. The crude product was purified by silica gel chromatography to give Compound 47 (8 g, 58% yield) as white solid.

$^1$H NMR 400 MHz CDCl$_3$: δ 11.73 (s, 1H), 8.97 (d, J=6.4 Hz, 1H), 7.40-7.32 (m, 10H), 5.21 (s, 2H), 5.12 (s, 2H), 4.19-4.11 (m, 1H), 3.86-3.82 (m, 4H), 3.02 (br. s, 2H).

General Procedure for Preparation of Compound 48:

A mixture of Compound 67 (5.0 g, 12.46 mmol, 1.00 eq) and Pd/C (500 mg) in dichloromethane (20 mL) and methanol (60 mL) was hydrogenated under 25 Psi of hydrogen pressure for 10 hrs at 25° C. The suspension was filtered through a pad of Celite and the pad cake was washed with methanol (500 mL). The combined filtrates were concentrated to dryness to give Compound 48 (1.7 g, crude) as a yellow oil which was used without further purification.

Example 44

Synthesis of Compound 49

Compound 49 was made by the synthetic method outlined in Scheme 26:

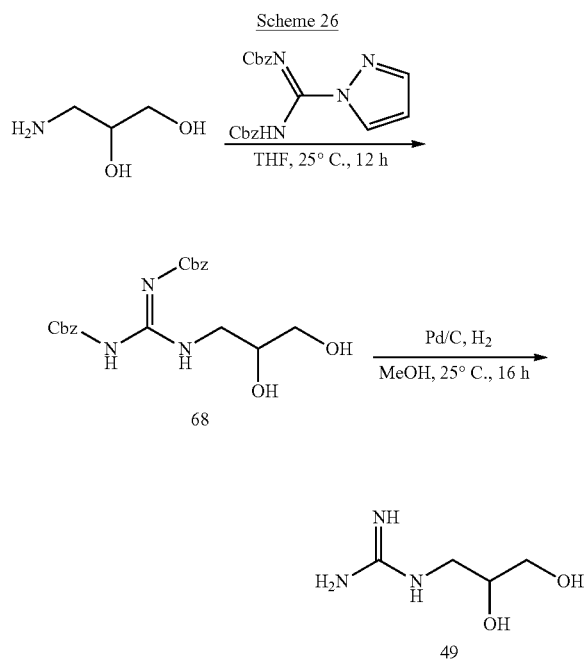

General Procedure for Preparation of Compound 68:

To the solution of 3-aminopropane-1,2-diol (3.0 g, 32.9 mmol, 2.54 mL, 1.00 eq) in THF (60 mL) was added N,N-di-CBZ-1H-pyrazole-1-carbamidine (11.2 g, 29.6 mmol, 0.90 eq). Then the reaction was stirred at 25° C. for 15 hrs. The reaction mixture was concentrated to dryness. The crude product was purified by silica gel chromatography to give Compound 68 (12 g, 86%) as white solid.

$^1$H NMR 400 MHz CDCl$_3$: δ 11.70 (s, 1H), 8.66 (s, 1H), 7.56 (d, J=3.6 Hz, 2H), 7.40-7.32 (m, 9H), 6.34-6.31 (m, 1H), 5.20 (s, 2H), 5.13 (s, 2H), 3.83-3.79 (m, 1H), 3.66-3.52 (m, 4H).

General Procedure for Preparation of Compound 49:

To a solution of Compound 68 (5.0 g, 12.5 mmol, 1.00 eq) in dichloromethane (20 mL) and methanol (60 mL) was added Pd/C (500 mg). The mixture was stirred under H$_2$ (25 psi) at 25° C. for 10 hrs. The suspension was filtered through a pad of Celite and the pad was washed with methanol (500 mL). The combined filtrates were concentrated to dryness to give Compound 49 (1.7 g, crude) as light yellow oil.

$^1$H NMR 400 MHz MeOD: δ 3.79-3.73 (m, 1H), 3.58-3.48 (m, 2H), 3.39-3.34 (m, 1H), 3.26-3.21 (m, 1H).

Example 45

Synthesis of Compound 75

Compound 75 is a Penultimate Intermediate in the Synthesis of Compounds 13-26

Compound 75 was made by the synthetic method outlined in Scheme 27:

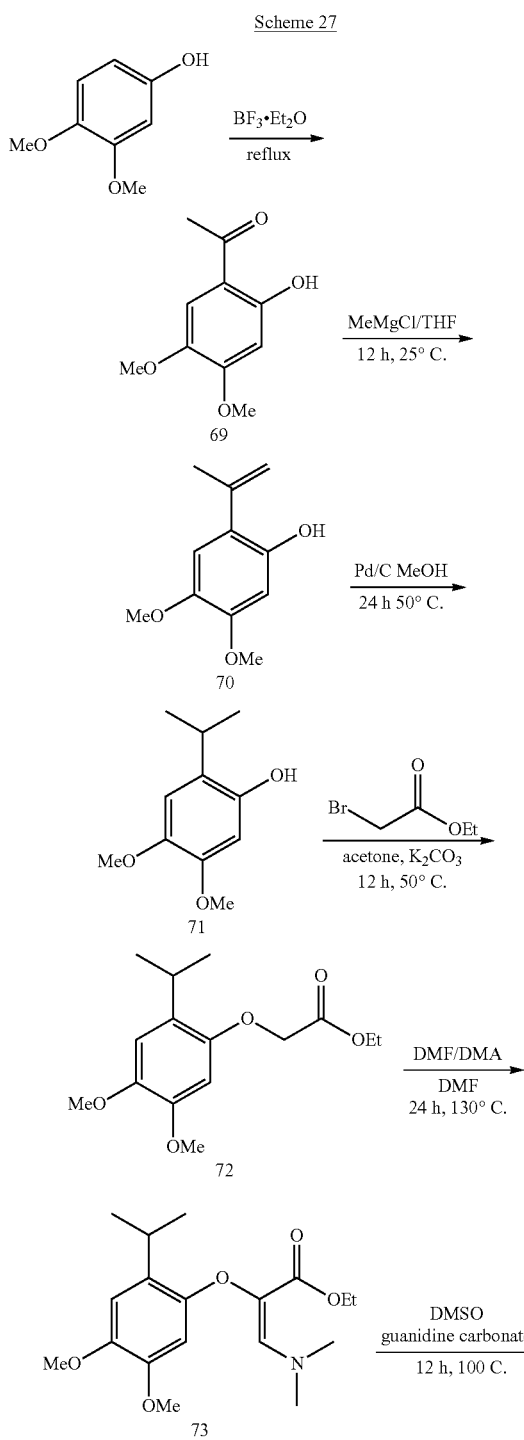

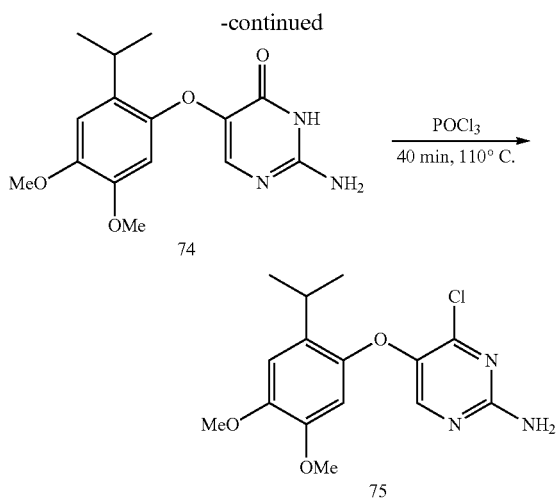

General Procedure for Preparation of Compound 69:

Into a 1000-mL 3-necked round-bottom flask was placed 3,4-dimethoxyphenol (50 g, 324.33 mmol, 1.00 equiv), HOAc (300 mL), and BF$_3$.Et$_2$O (100 mL, 3.00 equiv). The resulting solution was stirred at 100° C. for 3 h, cooled to room temperature, quenched with ice water and filtered. The filtrate was dried to afford 35 g (55%) of Compound 69 as a yellow solid.

MS: [M+H] 197.0

General Procedure for Preparation of Compound 70:

Into a 1000-mL 3-necked round-bottom flask purged and maintained with an inert atmosphere of nitrogen was placed Compound 69 (35 g, 178.39 mmol, 1.00 equiv), THF (300 mL), and MeMgBr (120 mL, 2.00 equiv). The resulting solution was stirred at 0° C. for 30 min and 12 h at 25° C., quenched with 300 mL of water, and extracted with 2×200 mL of ethyl acetate. The combined organic layers were dried over anhydrous sodium sulfate and concentrated under vacuum. The residue was purified on a silica gel column to afford 30 g (87%) Compound 70 as a yellow solid.

General Procedure for Preparation of Compound 71:

Into a 500-mL round-bottom flask purged and maintained with an inert atmosphere of nitrogen was placed Compound 70 (30 g, 154.46 mmol, 1.00 equiv), methanol (300 mL), and palladium carbon (3 g). To the above system, H$_2$ (enough, gas) was introduced. The resulting solution was stirred at 50° C. for 24 h, cooled to room temperature, and filtered. The filtrate was concentrated under vacuum and dried to afford 25 g (82%) Compound 71 as a light yellow solid.

General Procedure for Preparation of Compound 72:

Into a 500-mL 3-necked round-bottom flask purged and maintained with an inert atmosphere of nitrogen was placed Compound 71 (25 g, 127.39 mmol, 1.00 equiv), acetone (300 mL), ethyl 2-bromoacetate (31 g, 185.63 mmol, 1.50 equiv), and potassium carbonate (26.3 g, 190.29 mmol, 1.50 equiv). The resulting solution was stirred at 50° C. for 12 h, cooled to room temperature, quenched with 200 mL of water, and extracted with 3×100 mL of ethyl acetate. The combined organic layers were dried over anhydrous sodium sulfate and concentrated under vacuum. The residue was purified by silica gel column to afford 25 g (70%) of Compound 72 as a light yellow solid.

General Procedure for Preparation of Compound 73:

Into a 250-mL sealed tube purged and maintained with an inert atmosphere of nitrogen was placed Compound 72 (10 g, 35.42 mmol, 1.00 equiv), N,N-dimethylformamide (50 mL), and DMF/DMA (50 mL). The resulting solution was stirred at 130° C. for 24 h, cooled to 25° C., diluted with 100 mL of water, and extracted with 3×100 mL of ethyl acetate. The combined organic layers were dried over anhydrous sodium sulfate and concentrated under vacuum. The residue was purified on a silica gel column to afford 6.0 g (50%) of Compound 73 as light yellow solid.

General Procedure for Preparation of Compound 74:

Into a 100-mL 3-necked round-bottom flask purged and maintained with an inert atmosphere of nitrogen was placed guanidine carbonate (14.6 g, 120.57 mmol, 3.00 equiv) and DMSO (20 mL) followed by the addition of sodium methylate (10.8 g, 199.93 mmol, 5.00 equiv) in several batches with stirring. To this reaction system was added a solution of Compound 73 (13 g, 38.53 mmol, 1.00 equiv) in DMSO (20 mL). The resulting solution was stirred at 100° C. for 12 h, cooled to 25° C., and quenched by 40 mL of water. The pH value of the solution was adjusted to 7 with HOAc. The resulting solution was extracted with 3×100 mL of ethyl acetate. The combined organic layers were dried over anhydrous sodium sulfate and concentrated. The residue was purified by silica gel column to afford 5.3 g (45%) of Compound 74 as a yellow solid.

General Procedure for Preparation of Compound 75:

Into a 100-mL round-bottom flask, was placed Compound 74 (3 g, 9.83 mmol, 1.00 equiv) and phosphoryl trichloride (40 mL). The resulting solution was stirred at 110° C. for 40 min, cooled to 0° C., quenched by the addition of 100 mL of ice water. The pH value of the solution was adjusted to 8 with ammonia. The mixture was stirred at 50° C. for 2 h and extracted with 4×50 mL of ethyl acetate. The combined organic layers were dried over anhydrous sodium sulfate and concentrated under vacuum. The residue was purified on a silica gel column to afford 1.4 g (44%) of Compound 75 as a light yellow solid.

Example 46

Synthesis of Compound 12

Compound 12 was made by the synthetic method outlined in Scheme 28:

Scheme 28

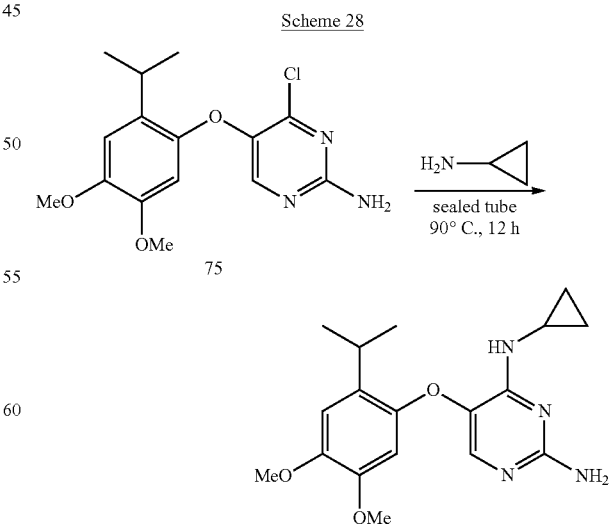

Compound 75 was prepared as outlined above in Example 23.

General Procedure for Preparation of Compound 12:

Into a 40 mL thick walled glass vial, for example a microwave reaction vial, was placed Compound 75 (100 mg, 0.31 mmol, 1.0 eq.), cyclopropylamine (88 mg, 1.55 mmol, 5.0 eq.) and acetonitrile (5 mL). The vial was sealed with a pressure rated cap, and the mixture was stirred in a thermal bath at 90° C. for 12 h, cooled to room temperature and concentrated under reduced pressure to give crude product which was further purified by PTLC to afford Compound 12.

$^1$HNMR 300 MHz, CDCl$_3$: δ 7.24 (s, 1H), 6.80 (s, 1H), 6.39 (s, 1H), 5.40 (s, 1H), 4.86 (s, 2H), 3.91 (s, 3H), 3.77 (s, 3H), 3.15-3.24 (m, 1H, J=27 Hz), 2.83-2.91 (m, 1H, J=24 Hz), 1.22-1.24 (m, 6H), 0.86-0.90 (m, 2H), 0.59-0.62 (m, 2H).

MS: [M+1] 345

Using the general procedure given for Compound 12, the following examples were synthesized substituting the appropriate amine in the same stoichiometric ratio:

Compound 13

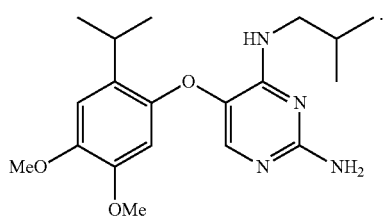

$^1$HNMR 300 MHz, CDCl$_3$: δ 7.307 (s, 1H), 6.811 (s, 1H), 6.418 (s, 1H), 5.217-5.253 (t, 1H), 4.685 (s, 2H), 3.881 (s, 3H), 3.797 (s, 3H), 3.269-3.319 (m, 2H), 3.199-3.245 (m, 1H), 1.830-1.942 (m, 1H), 1.241-1.264 (d, 6H), 0.945-0.967 (d, 6H).

MS: [M+1] 361.2

Compound 14

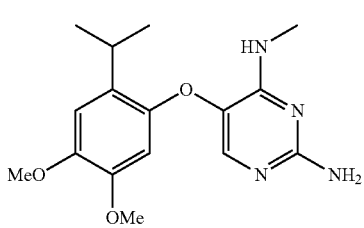

$^1$HNMR 300 MHz, CDCl$_3$: δ 7.247 (s, 1H), 6.801 (s, 1H), 6.398 (s, 1H), 5.250-5.261 (d, 1H), 4.769 (s, 2H), 3.869 (s, 3H), 3.761 (s, 3H), 3.171-3.263 (m, 1H), 3.027-3.044 (d, 3H), 1.189-1.246 (d, 6H).

MS: [M+1] 319.3

Compound 15

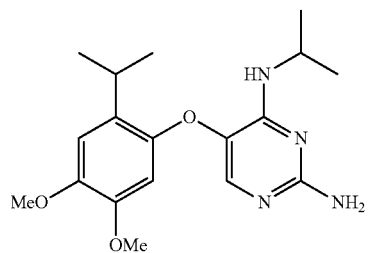

$^1$HNMR 300 MHz, CDCl$_3$: δ 7.221 (s, 1H), 6.811 (s, 1H), 6.418 (s, 1H), 5.108-5.134 (d, 1H), 4.866 (s, 2H), 4.266-4.335 (m, 1H), 3.909 (s, 3H), 3.777 (s, 3H), 3.163-3.256 (m, 1H), 1.234-1.276 (d, 6H), 1.156-1.178 (d, 6H).

MS: [M+1] 347.2

Compound 16

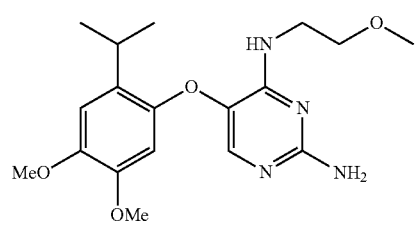

$^1$HNMR 300 MHz, CDCl$_3$: δ 7.306 (s, 1H), 6.807 (s, 1H), 6.425 (s, 1H), 5.541-5.559 (d, 1H), 4.670 (s, 2H), 3.903 (s, 3H), 3.794 (s, 3H), 3.639-3.691 (m, 2H), 3.553-3.607 (m, 2H), 3.375 (s, 3H), 3.198-3.290 (m, 1H), 1.233-1.256 (d, 6H).

MS: [M+1] 363.2

Compound 17

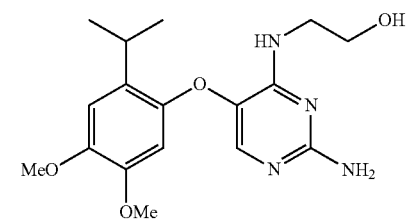

$^1$HNMR 300 MHz, CDCl$_3$: δ 7.253 (s, 1H), 6.803 (s, 1H), 6.422 (s, 1H), 5.715-5.751 (t, 1H), 4.787 (s, 2H), 3.901 (s, 3H), 3.834-3.866 (m, 2H), 3.776 (s, 3H), 3.637-3.688 (m, 2H), 3.158-3.250 (m, 1H), 1.186-1.244 (d, 6H).

MS: [M+1] 349.1

Compound 18

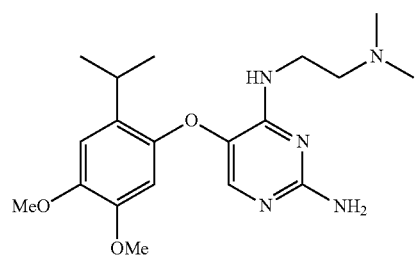

¹HNMR 300 MHz, CDCl₃: δ 7.327 (s, 1H), 6.812 (s, 1H), 6.432 (s, 1H), 5.816 (s, 1H), 4.707 (s, 2H), 3.901 (s, 3H), 3.768 (s, 3H), 3.472-3.530 (m, 2H), 3.204-3.296 (m, 1H), 2.491-2.531 (m, 2H), 2.228 (s, 6H), 1.238-1.261 (d, 6H).
MS: [M+1] 376.3

Compound 19

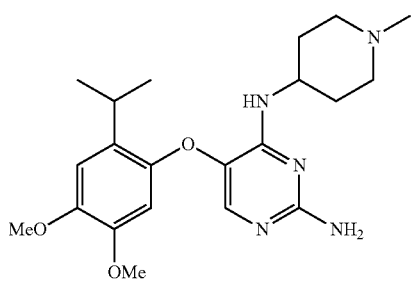

¹HNMR 300 MHz, CDCl₃: δ 7.271-2.282 (d, 1H), 6.809 (s, 1H), 6.419 (s, 1H), 5.125-5.153 (d, 1H), 4.797 (s, 2H), 4.000-4.100 (m, 1H), 3.901 (s, 3H), 3.774 (s, 3H), 3.136-3.256 (m, 1H), 2.916-3.015 (m, 2H), 2.419 (s, 3H), 2.316-2.349 (m, 2H), 2.101-2.133 (m, 2H), 1.708-1.778 (m, 2H), 1.230-1.253 (d, 6H).
MS: [M+1] 402.3

Compound 20

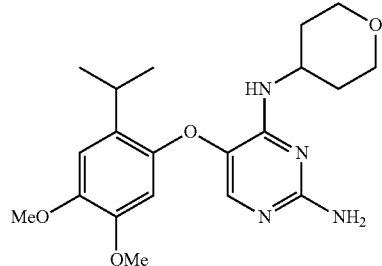

¹HNMR 300 MHz, CDCl₃: δ 7.280 (s, 1H), 6.812 (s, 1H), 6.420 (s, 1H), 5.132-5.158 (d, 1H), 4.781 (s, 2H), 4.100-4.300 (m, 1H), 3.960-4.100 (m, 2H), 3.982 (s, 3H), 3.774 (s, 3H), 3.524-3.667 (m, 2H), 3.165-3.254 (m, 1H), 2.028-2.208 (m, 2H), 1.500-1.613 (m, 2H), 1.230-1.350 (d, 6H).
MS: [M+1] 389.2

Compound 21

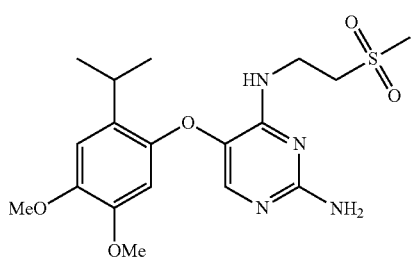

¹HNMR 300 MHz, CDCl₃: δ 6.806 (s, 1H), 6.412 (s, 1H), 5.898 (s, 1H), 4.866 (s, 2H), 4.009-4.070 (m, 2H), 3.905 (s, 1H), 3.775 (s, 3H), 3.399-3.439 (m, 2H), 2.982-3.216 (m, 1H, J=6.9 Hz), 2.982 (s, 3H), 1.219-1.242 (d, 6H).
MS: [M+1] 411.3

Compound 22

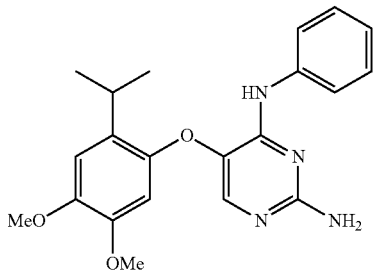

¹HNMR 300 MHz, CDCl₃: δ 7.685-7.717 (m, 2H), 7.347-7.404 (m, 3H). 7.200 (s, 1H), 7.090-7.140 (t, 1H), 6.837 (s, 1H), 6.490 (s, 1H), 4.834 (s, 2H), 3.922 (s, 3H), 3.785 (s, 1H), 3.212-3.304 (m, 1H), 1.260-1.283 (d, 6H).
MS: [M+1] 381.2

Compound 26

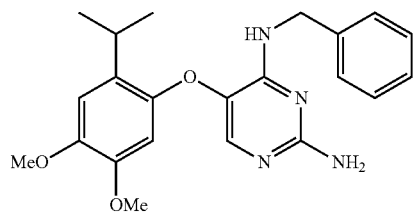

¹HNMR 300 MHz, CDCl₃: δ 7.283-7.395 (m, 6H), 6.792 (s, 1H), 6.416 (s, 1H), 5.552-5.588 (t, 1H), 4.816 (s, 2H), 4.689-4.708 (d, 2H), 3.898 (s, 3H), 3.758 (s, 3H), 3.161-3.253 (m, 1H), 1.168-1.277 (d, 6H).
MS: [M+1] 395.2

Example 47

Synthesis of Compound 23

Compound 23 was made by the synthetic method outlined in Scheme 29:

Scheme 29

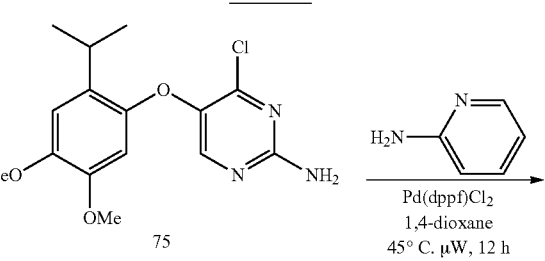

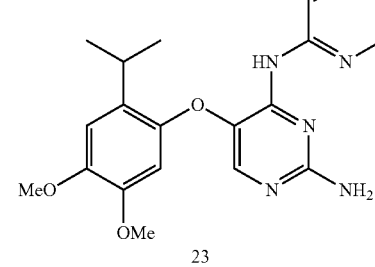

Compound 75 was prepared as outlined above in Example 23.

General Procedure for Preparation of Compound 23

Into a 40 mL vial was placed 4-chloro-5-(2-isopropyl-4,5-dimethoxyphenoxy) pyrimidin-2-amine (100 mg, 0.31 mmol, 1.0 eq.), 2-aminopyridine (145 mg, 1.55 mmol, 5.0 eq), XantPhos (15 mg), $Pd_2(dba)_3Cl_2$ (10 mg), $Cs_2CO_3$ (200 mg, 0.62 mmol, 2.0 eq) and 1,4-dioxane (5 mL). The mixture was stirred at 100° C. for 30 mins under microwave heating, cooled to room temperature, quenched with 10 mL of water, and extracted with 2×10 mL of ethyl acetate. The combined organic layers were dried over anhydrous sodium sulfate and concentrated under vacuum. The crude product was purified by prep-TLC to afford Compound 23.

$^1$HNMR 300 MHz, $CDCl_3$: δ: 8.53-8.56 (d, 1H, J=9 Hz), 8.31-8.32 (d, 1H, J=3 Hz), 8.04 (s, 1H), 7.72-7.78 (t, 1H, J=18 Hz), 7.42 (s, 1H), 7.00-7.03 (t, 1H, J=9 Hz), 6.83 (s, 3H), 6.46 (s, 3H), 4.92 (s, 1H), 3.92-4.01 (d, 3H, J=27 Hz), 3.68-3.78 (d, 3H, J=30 Hz), 3.19-3.28 (m, 1H, J=27 Hz), 1.25-1.27 (d, 6H).

MS: [M+1] 382.2

Example 48

Synthesis of Compound 24

Compound 24 was made by the synthetic method outlined in Scheme 30:

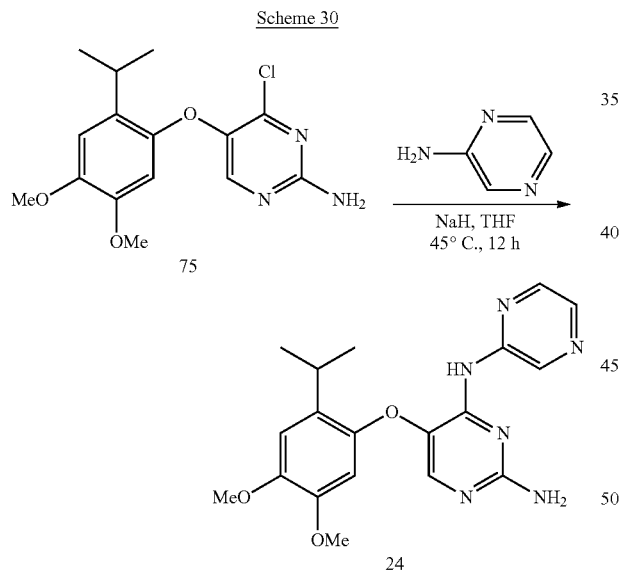

Compound 75 was prepared as outlined above in Example 23.

General Procedure for Preparation of Compound 24:

Into a 40 mL vial was placed 4-chloro-5-(2-isopropyl-4,5-dimethoxyphenoxy) pyrimidin-2-amine (100 mg, 0.31 mmol, 1.0 eq), aminopyrazine (88 mg, 0.93 mmol, 3.0 eq), THF (5 mL) and NaH (1.55 mmol, 37 mg, 5.0 eq, 60% in mineral oil). The mixture was stirred at 45° C. for 12 h, cooled to room temperature, quenched by 3 drops of water, and concentrated under reduced pressure. The crude product was further purified by prep-TLC to afford Compound 24.

$^1$HNMR 300 MHz, $CDCl_3$: δ 9.90 (s, 1H), 8.27-8.32 (m, 2H), 7.92 (s, 1H), 7.50 (s, 1H), 6.81-6.84 (d, 1H, J=9 Hz), 6.47 (s, 1H), 4.92 (s, 2H), 3.90-3.93 (d, 3H, J=9 Hz), 3.75-3.79 (d, 3H, J=12 Hz), 1.26-1.28 (d, 6H).

MS: [M+1] 383.3

Using the general procedure given for Compound 13, the Compound 25 was synthesized substituting appropriate amine:

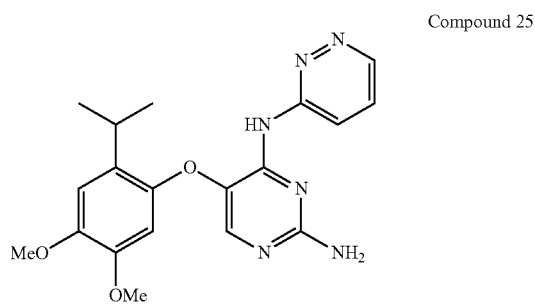 [SMILES: COc1cc(Oc2cnc(N)nc2Nc2cccnn2)c(C(C)C)cc1OC]

1HNMR 300 MHz, $CDCl_3$: δ 8.920-8.940 (m, 1H), 8.804-8.838 (m, 1H), 8.506 (s, 1H), 7.501-7.532 (t, 1H), 7.486 (s, 1H), 6.847 (s, 1H), 6.479 (s, 1H), 4.961 (s, 2H), 3.931 (s, 3H), 3.795 (s, 3H), 3.182-3.273 (m, 1H), 1.256-1.279 (d, 6H).

MS: [M+1] 383.1

Example 49

General Procedure for Preparation of Compound AF056

An exemplary synthetic route for AF056 is as follows:

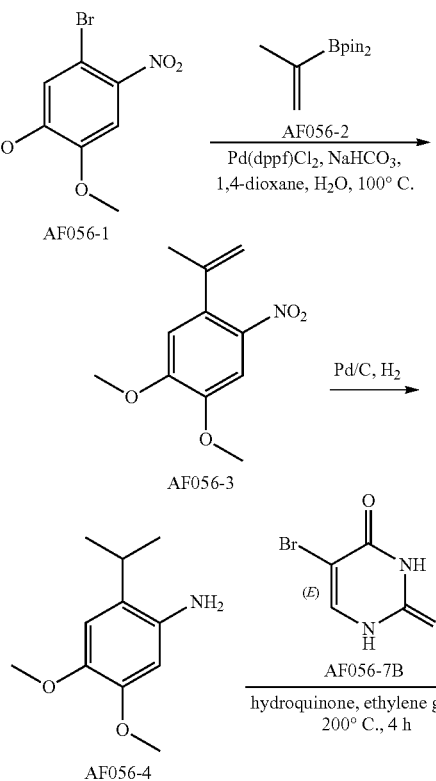

-continued

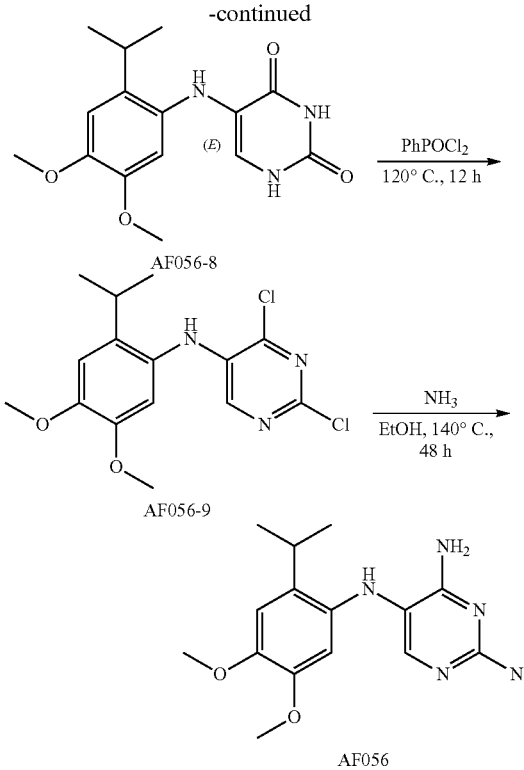

A general procedure for preparation of Compound AF056-3 is as follows:

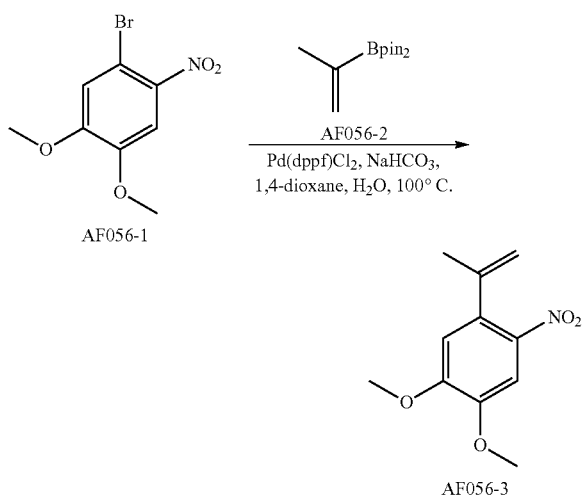

A solution of AF056-1 (5.00 g, 19.1 mmol, 1.00 eq), AF056-2 (3.85 g, 22.9 mmol, 1.20 eq), Pd(dppf)Cl₂ (279 mg, 0.381 mmol, 0.02 eq) and NaHCO₃ (3.21 g, 38.2 mmol, 1.48 mL, 2.00 eq) in 1,4-dioxane (40.0 mL) and H₂O (8.0 mL) was heated at 100° C. for 12 h under N₂ atmosphere. LCMS showed starting material was consumed completely and the main peak was desired. To the mixture was added ethyl acetate (50 mL) and H₂O (20 mL). The two phases were separated and the aqueous phase was extracted with ethyl acetate (2×50 mL). The combined organic phases were dried, filtered and concentrated. The residue was purified via column chromatography on silica gel (eluting with petroleum to petroleum ether: ethyl acetate=5:1) to give AF056-3 (3.80 g, 17.0 mmol, 89% yield) as a yellow oil.

¹H NMR (400 MHz, DMSO-d₆) δ=7.55 (s, 1H), 6.90 (s, 1H), 5.16-5.08 (m, 1H), 4.90-4.83 (m, 1H), 3.88 (s, 3H), 3.85 (s, 3H), 2.02 (d, J=0.7 Hz, 3H)

A general procedure for preparation of Compound AF056-4 is as set forth below:

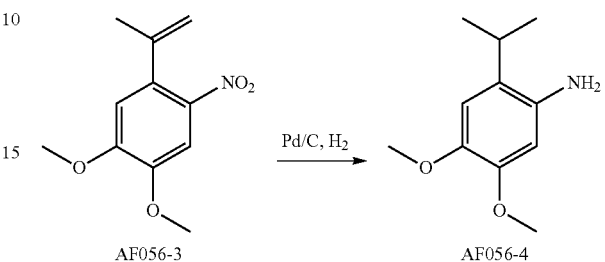

A solution of AF056-3 (3.80 g, 17.0 mmol, 1.00 eq) and Pd/C (906 mg, 8.51 mmol, 0.50 eq) in MeOH (80.00 mL) was stirred at 20° C. under H₂ (50 psi) for 12 h. LCMS showed starting material was consumed completely. The mixture was filtered and the solid was washed with MeOH (100 mL). Then the combined filtrates were were concentrated to give AF056-4 (3.00 g, 15.4 mmol, 90% yield) as brown oil which was used for the next step without purification.

¹H NMR (400 MHz, DMSO-d₆) δ=6.59 (s, 1H), 6.31 (s, 1H), 4.45 (s, 2H), 3.64 (s, 3H), 3.62 (s, 3H), 2.88 (td, J=6.7, 13.8 Hz, 1H), 1.10 (d, J=6.6 Hz, 6H)

A general procedure for the preparation of Compound AF056-8 is as follows:

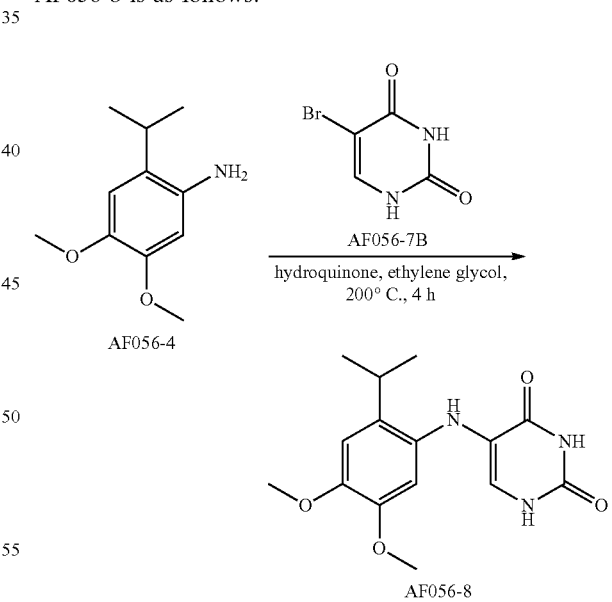

The mixture of AF056-4 (1.02 g, 5.22 mmol, 3.50 eq), AF056-7B (285 mg, 1.49 mmol, 1.00 eq) and hydroquinone (16.4 mg, 149 wool, 0.10 eq) in ethylene glycol (6.00 mL) was stirred at 200° C. for 4 h. LCMS showed most of the starting material (AF056-7B) was consumed and the main peak was desired. One additional vial was set up as described above. All the two reaction mixtures were combined. To the mixture was added ethyl acetate (30 mL) and H₂O (10 mL). The aqueous phase was separated and extracted with ethyl acetate (2×20 mL). The organic phases were combined, dried over anhydrous Na$_2$SO$_4$, filtered and concentrated. The residue was purified via prep-HPLC to give AF056-8 (500 mg, 1.64 mmol, 55% yield) as a light yellow solid.

Prep-HPLC Method:

Instrument: Shimadzu LC-8A preparative HPLC

Column: Phenomenex luna C18 250*50 mm*10 um

Mobile phase: A for H$_2$O (0.09% TFA) and B for CH$_3$CN

Gradient: B from 10% to 40% in 20 min

Flow rate: 80 mL/min

Wavelength: 220&254 nm $^1$H NMR (400 MHz, DMSO-d$_6$) δ=11.26 (s, 1H), 10.21 (br d, J=4.4 Hz, 1H), 6.80 (s, 1H), 6.53 (s, 1H), 6.38 (d, J=5.5 Hz, 1H), 5.92 (s, 1H), 3.73 (s, 3H), 3.66 (s, 3H), 3.01 (quin, J=6.8 Hz, 1H), 1.13 (d, J=6.8 Hz, 6H)

A general procedure for the preparation of Compound AF056-9 is as follows:

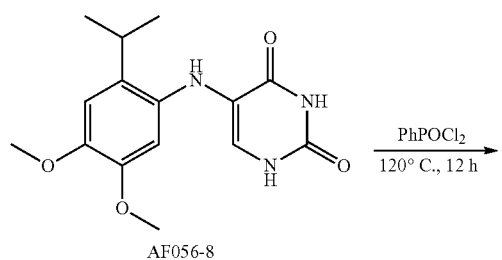

A mixture of AF056-8 (500 mg, 1.64 mmol, 1.00 eq) in PhPOCl$_2$ (2.76 mL, 19.7 mmol, 12.00 eq) was degassed by sparging with N$_2$ for 3 times and then stirred at 120° C. for 12 h under N$_2$ atmosphere. LCMS showed starting material was consumed completely and the main peak was desired. The reaction mixture was poured to ice. Then ethyl acetate (30 mL) and H$_2$O (10 mL) were added in. The two phases were separated and the aqueous phase was extracted with ethyl acetate (2×15 mL). The combined organic phases were washed with saturated Na$_2$CO$_3$ (3×10 mL) and dried over anhydrous Na$_2$SO$_4$. Then filtered and concentrated to give AF056-9 (285 mg, 833 umol, 51% yield) as a brown solid which was used for the next step directly.

$^1$H NMR (400 MHz, chloroform-d) δ=7.76 (s, 1H), 6.86 (s, 1H), 6.66 (s, 1H), 5.67 (s, 1H), 3.94 (s, 3H), 3.83 (s, 3H), 3.04 (td, J=6.7, 13.7 Hz, 1H), 1.20 (d, J=7.1 Hz, 6H)

A general procedure for the preparation of Compound AF056 is as follows:

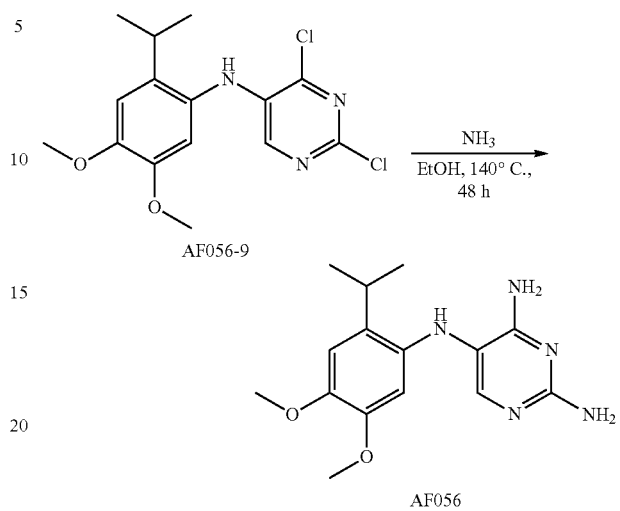

A solution of AF056-9 (285 mg, 833 μmol, 1.00 eq) in NH$_3$/EtOH (20 N, 10 mL) was added to an autoclave. The mixture was stirred at 140° C. for 48 h. LCMS and HPLC showed starting material was consumed completely and the ratio of desired product and mono-amino byproduct was 1 to 1.5. The mixture was concentrated. The residue was purified via prep-TLC (CH$_2$Cl$_2$:MeOH=15:1) to give 50 mg of desired product which was further purified via prep-HPLC to give AF056 (14.0 mg, 46.2 umol, 5% yield) as a pink solid. Finally, this batch of final compound was combined with 3 mg of product from ET8131-283 and a total of 17 mg of AF056 was obtained.

Prep-HPLC Method:

Instrument: Gilson 281 semi-preparative HPLC system

Mobile phase: A: 10 mM NH$_4$HCO$_3$ in H$_2$O; B: CH$_3$CN

Column: YMC-Actus Triart C18 150*30 5 u

Flow rate: 25 mL/min

Monitor wavelength: 220&254 nm

| Time | B % |
|---|---|
| 0.0 | 30 |
| 12.0 | 50 |
| 12.1 | 50 |
| 12.2 | 100 |
| 14.2 | 100 |
| 14.3 | 30 |
| 15.5 | 30 |

$^1$H NMR (400 MHz, CHLOROFORM-d)

δ=7.76 (s, 1H), 6.80 (s, 1H), 6.09 (s, 1H), 4.91 (br s, 2H), 4.76 (s, 2H), 4.66 (s, 1H), 3.85 (s, 3H), 3.72 (s, 3H), 3.04 (spt, J=6.8 Hz, 1H), 1.31 (d, J=6.6 Hz, 6H)

Example 50

Biological Assay

1321N1 human astrocytoma and HEK293 human embryonic kidney cells were stably transfected with human P2X2 and P2X3 receptor subunits to form heteromeric P2X2/3 channels and passaged in flasks. Additionally, HEK293 cells were stably transfected with human P2X3 receptor subunits to form homomeric P2X3 channels.

Approximately 24 hours before the FlexStation calcium fluorescence experiment, cells were released from their flasks, centrifuged and re-suspended in nutrient medium. The cells were aliquoted into black-wall, clear-bottom 96 well plates at a density of 25,000 cells per well and incubated overnight in a humidified, $CO_2$-enriched (5%) atmosphere at 37° C.

On the day of the experiment, cells were washed with assay buffer (calcium- and magnesium-free Hank's balanced salt solution, 20 mM HEPES, 2 mM $CaCl_2$; AB) and loaded with 4 μM Fluo-4 (P2X2/3) or Calcium 6 (Molecular Devices, according to manufacturer's instructions; P2X3) calcium-sensitive fluorescent dye in 100 μL AB.

After 1 hour of dye loading at 37° C., 1321N1-hP2X2/3 cells were washed two times with AB and test compound or vehicle added to each well in a total volume of 150 μL AB. HEK-hP2X3 cells were not washed because the Calcium 6 dye kit includes an extracellular dye that quenches unabsorbed Calcium 6 dye; test compound or vehicle were added directly to the assay plates to achieve the appropriate concentration of test compound in a total volume of 150 μL AB.

After 20 minutes incubation at room temperature and protected from light, the assay plates were loaded into the FlexStation microplate reader and baseline fluorescence measured with an excitation wavelength of 485 nm and emission wavelength readings centered at 525 nm (515 nm cut off).

The agonist was dispensed by the FlexStation during fluorescence measurement to construct agonist activation and antagonist inhibition curves. The final agonist concentration for inhibition was 1 μM α,β-meATP for P2X3 and 3 μM ATP for P2X2/3. Peak fluorescence was measured and curves generated using a four parameter nonlinear regression equation.

The data in Table 2 were obtained using the assay referred to above:

TABLE 2

| # | Structure | Average pIC$_{50}$ | | Selectivity |
|---|---|---|---|---|
| | | P2X3 | P2X2/3 | P2X3/P2X2/3 |
| 1 | 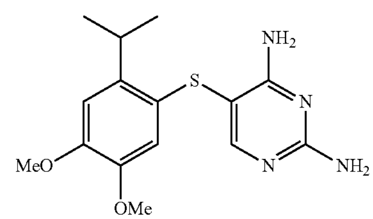 [SMILES: COc1cc(Sc2cnc(N)nc2N)c(C(C)C)cc1OC] | 7.0 | <5 | >100 |
| 2 | 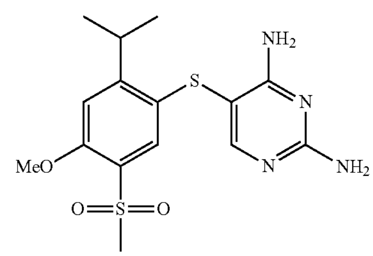 [SMILES: COc1cc(C(C)C)c(Sc2cnc(N)nc2N)cc1S(C)(=O)=O] | 6.3 | <5 | >18 |
| 3 | 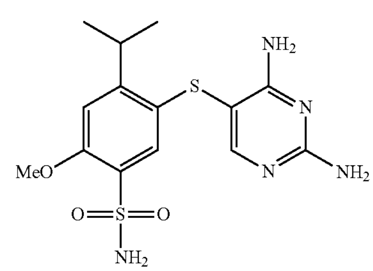 [SMILES: COc1cc(C(C)C)c(Sc2cnc(N)nc2N)cc1S(N)(=O)=O] | 6.8 | <5 | >67 |
| 4 | 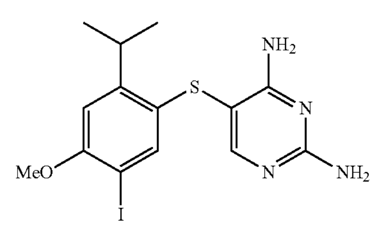 | 6.9 | 5.2 | 48 |

TABLE 2-continued

| # | Structure | A | B | C |
|---|---|---|---|---|
| 5 | 2-isopropyl-4-methoxy-5-ethynylphenyl thio-2,4-diaminopyrimidine | 7.4 | 5.4 | 97 |
| 6 | 2-isopropyl-4-methoxy-5-(prop-1-ynyl)phenylthio-2,4-diaminopyrimidine | 6.1 | <5 | >13 |
| 7 | 2-isopropyl-4-methoxy-5-methylphenylthio-2,4-diaminopyrimidine | 6.5 | <5 | >34 |
| 8 | 2-isopropyl-4-methoxy-5-bromophenylthio-2,4-diaminopyrimidine | 6.7 | <5 | >47 |
| 9 | 2-isopropyl-4-methoxy-5-chlorophenylthio-2,4-diaminopyrimidine | 6.8 | <5 | >56 |
| 10 | 4-isopropyl-5-methoxy-2-cyanophenylthio-2,4-diaminopyrimidine | <5 | <5 | NA |

TABLE 2-continued

| # | Structure | | | |
|---|---|---|---|---|
| 11 | (isopropyl, MeO, tetrazolyl-phenyl)-S-(2,4-diaminopyrimidine) | 6.8 | <5 | >58 |
| 12 | (isopropyl, MeO, COOH-phenyl)-S-(2,4-diaminopyrimidine) | 5.3 | <5 | >2 |
| Comparative Compound 1 | (isopropyl, MeO, OMe-phenyl)-S(=O)-(2,4-diaminopyrimidine) | <5 | <5 | NA |
| Comparative Compound 2 | (isopropyl, MeO, OMe-phenyl)-S(=O)₂-(2,4-diaminopyrimidine) | <5 | <5 | NA |
| 13 | (isopropyl, diMeO-pyridyl)-O-(2,4-diaminopyrimidine) | 7.4 | 6.7 | 5.2 |
| 14 | (isopropyl, MeO-pyridazinyl)-O-(2,4-diaminopyrimidine) | 5.9 | <5 | >7.1 |
| 15 | (isopropyl, MeO, I-pyridyl)-O-(2,4-diaminopyrimidine) | 7.2 | 6.4 | 6.5 |

TABLE 2-continued

| # | Structure | P2X3 | P2X2/3 | Selectivity |
|---|---|---|---|---|
| 16 | (isopropyl-methoxy-methylsulfonyl-pyridine linked via O to 2,4-diaminopyrimidine) | 7.2 | <5 | >145 |
| 17 | (isopropyl-methoxy-cyano-pyridine linked via O to 2,4-diaminopyrimidine) | 6.0 | <5 | >10 |
| 18 | (isopropyl-methoxy-trifluoromethyl-pyridine linked via O to 2,4-diaminopyrimidine) | 7.2 | 5.8 | 23 |
| 19 | (isopropyl-methoxy-ethynyl-pyridine linked via O to 2,4-diaminopyrimidine) | 8.2 | 6.7 | 28 |
| 20 | (isopropyl-methoxy-sulfamoyl-pyridine linked via O to 2,4-diaminopyrimidine) | 7.7 | 6.4 | 19 |

| Compound # | Average $pIC_{50}$ | | Selectivity |
|---|---|---|---|
| | P2X3 | P2X2/3 | P2X3 vs P2X2/3 |
| 21 | 7.1 | 6.4 | 5.0 |
| 22 | 6.7 | 5.8 | 7.9 |
| 23 | 6.0 | <5 | >10.5 |
| 24 | 5.8 | <5 | >5.9 |
| 25 | 6.2 | 5.6 | 4.3 |
| 26 | 6.2 | 5.5 | 5.4 |
| 27 | 6.7 | 6.3 | 2.5 |
| 28 | 6.4 | 5.9 | 3.2 |
| 29 | 6.4 | 5.5 | 9.3 |
| 30 | 6.9 | 6.2 | 4.9 |
| 31 | 6.7 | 5.4 | 21 |
| 32 | 6.1 | 5.9 | 1.6 |
| 33 | 6.2 | <5 | >15 |
| 34 | 5.8 | <5 | >6.4 |

TABLE 2-continued

| | | | |
|---|---|---|---|
| 35 | 5.4 | <5 | >2.5 |
| 36 | 6.0 | <5 | >10 |
| 37 | 6.0 | <5 | >10 |
| 38 | 6.8 | 5.6 | 17 |
| 39 | 6.5 | 5.2 | 20 |
| 40 | 5.9 | <5 | >8 |
| 41 | 6.4 | <5 | >27 |
| 42 | 6.0 | <5 | >10 |
| 43 | 5.8 | <5 | >5.6 |
| 44 | 6.0 | <5 | >10 |
| 45 | 5.5 | <5 | 3.5 |
| 46 | 6.2 | 5.5 | 4.8 |
| 47 | 7.31 | 5.86 | 28 |

The potential tolerability benefits of P2X3 channel selectivity have become evident with experience from clinical studies using novel drug-like antagonists. Previously reported carbon- and oxygen-linked diaminopyrimidine analogs display either no or only modest potency selectivity favoring homotrimeric P2X3 over heterotrimeric P2X2/3 channels.

For example the most selective carbon-linked analog displays a 16 fold selectivity ratio. Oxygen-linked examples shown in Table 1 (X=O) exhibit an average P2X3-to-P2X2/3 selectivity ratio of 10 (potencies shown as $pIC_{50s}$).

The data in Tables 3A and 3B show the $pIC_{50s}$ and selectivity of diaminopyrimidine antagonists of the P2X3 and P2X2/3 ion channels of previously disclosed oxygen-linked versus sulfur linked analogs of the present disclosure.

TABLE 3A

| | | X = O[1] | | | X = S | | |
|---|---|---|---|---|---|---|---|
| Row | R | P2X3 | P2X2/3 | Selectivity | P2X3[2] | P2X2/3[3] | Selectivity |
| A | OCH$_3$ | 7.6 | 6.3 | 20 | 7.0 | <5 | >100 |
| B | I | 8.0 | 7.1 | 8 | 6.8 | 5.2 | 48 |
| C | S(O)$_2$CH$_3$ | 7.0 | 6.0 | 10 | 6.3 | <5 | >18 |
| D | Cl | 7.6 | 7.0 | 4 | 6.8 | <5 | >50 |
| | Average selectivity: | | | 10 | | | >50 |

[1]Mean $pIC_{50s}$ from Carter et al, *Bioorg Med Chem Lett* 2009 Mar 15; 19(6): 1628-31.
[2]Mean $pIC_{50}$, hP2X3, HEK293 cells
[3]Mean $pIC_{50}$, hP2X2/3, 1321N1 (astrocytoma) cells One of the most selective diaminopyrimidine inhibitors previously known, the oxygen-linked analog in row A of Table 3A, has $pIC_{50s}$ of 7.6 and 6.3 for the P2X3 and P2X2/3 receptors, respectively, a potency ratio of 20 (pIC50=−log $IC_{50}$, Ratio=10^(P2X3pIC$_{50}$−P2X2/3pIC$_{50}$). The corresponding sulfur-linked analog (Row A, X=S; compound 1) exhibits $pIC_{50s}$ of 7.00 and <5 (highest concentration tested is 10 μM) at P2X3 and P2X2/3, respectively, or a selectivity ratio that is greater than 100.

TABLE 3B

[Structure diagram showing isopropyl/MeO-substituted phenyl ether linked to diaminopyrimidine with HNR' and NH2 substituents, with R on the phenyl ring]

| | | R = I | | | R = OMe | |
|---|---|---|---|---|---|---|
| Row | R' | P2X3[1] | P2X2/3[1] | Selectivity | P2X3[2] | P2X2/3[3] | Selectivity |
| A | CH2CH2OH | 8.0 | 7.8 | 1.6 | 6.7 | 5.8 | 7.9 |
| B | CH2(CHOH)CH2OH | 8.1 | 7.5 | 4.0 | 6.7 | 5.4 | 20 |
| C | CH(CH2OH)2 | 8.7 | 8.3 | 2.5 | 6.9 | 6.2 | 5.0 |
| | Average selectivity: | | | 2.7 | Average selectivity: | | 11 |

[1]Mean pIC$_{50s}$ from Jahangir et al, *Bioorg Med Chem Lett* 2009 Mar 15; 19(6): 1632-1635.
[2]Mean pIC$_{50}$, hP2X3, HEK293 cells, Table 2
[3]Mean pIC$_{50}$, hP2X2/3, 1321N1 (astrocytoma) cells, Table 2

The iodo example in row A of Table 3B has pIC$_{50s}$ of 8.0 and 7.8 for the P2X3 and P2X2/3 receptors, respectively, a potency ratio of 1.6 (pIC50=−log IC$_{50}$, Ratio=10^ (P2X3pIC$_{50}$−P2X2/3pIC$_{50}$). The corresponding N-alkylated dimethoxyaryl analog of the present invention (Row A, R=OMe, (compound 17)) exhibits a selectivity ratio of 7.9, a 5 fold increase. Other examples exhibit even greater increases in selectivity upon substituting methoxy for iodo, for example Row B compounds display a 20 fold increase in selectivity.

The average selectivity for the three matched pairs shown in Table 3 increases from 23 to 11. Although this is influenced by the larger gain of selectivity from Row B compounds, in every case the dimethoxy substituted arylether diaminopyrimidines exhibit higher selectivity than their iodo matched pair. The trend extends beyond these three examples to all diaminopyrimidine analogs that have published inhibition activity at the P2X3 and P2X2/3 receptors. For published analogs the average selectivity=4, while for the compounds of the present disclosure, the average selectivity=9.

All other pairs of analogs shown in Table 3 exhibit a significant increase in the selectivity ratio for the sulfur-linked analog relative to the corresponding oxygen- or carbon-linked compound.

Importantly, the average selectivity for sulfur-linked compounds in Table 3 is more than 5 times greater than the average selectivity of the oxygen-linked compounds.

The trend extends beyond these four examples to all diaminopyrimidine analogs that have published inhibition activity at the P2X3 and P2X2/3 receptors for oxygen- and carbon-linked analogs the average selectivity=4, while for the sulfur-linked analogs of the present disclosure the average selectivity is 45.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective spirit and scope of the present disclosure. All such modifications are intended to be within the scope of the claims appended hereto.

The invention claimed is:
1. A compound of Formula 1:

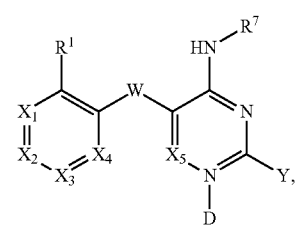

Formula 1 or a pharmaceutically acceptable salt thereof, wherein:
   W is O or S;
   $X_1$ is N or $CR^2$;
   $X_2$ is $CR^3$;
   $X_3$ is $CR^4$;
   $X_4$ is $CR^5$;
   $X_5$ is N or $CR^6$, provided, however, when $X_1$ is $CR^2$, W is not O;
   Y is selected from hydrogen or —$NR^dR^e$, wherein one of $R^d$ and $R^e$ is hydrogen, and the other is: hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalkyl; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{1-12}$-hydroxycarbonylalkyl; $C_{2-12}$-hydroxylalkyloxycarbonylalkyl; $C_{5-12}$-aryl; $C_{6-12}$-arylalkyl; $C_{5-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; or $C_{4-12}$-heterocyclylalkyl;
   D is an optional oxygen;
   $R^1$ is $C_{1-12}$-alkyl;
   $R^2$ and $R^4$ are each independently selected from hydrogen; $C_{1-12}$-alkyl; $C_{2-12}$-alkenyl; $C_{2-12}$-alkynyl; amino; halo; amido; $C_{1-12}$-haloalkyl; $C_{1-12}$-alkoxy; hydroxy; $C_{1-12}$-haloalkoxy; nitro; $C_{1-12}$-hydroxyalkyl; $C_{2-12}$-alkoxyalkyl; $C_{1-12}$-hydroxyalkoxy; $C_{3-12}$-alkynylalkoxy; $C_{1-12}$-alkylsulfonyl; $C_{5-12}$-arylsulfonyl; cyano; $C_{6-12}$-aryl; $C_{5-12}$-heteroaryl; $C_{3-12}$-heterocyclyl; $C_{4-12}$-heterocyclylalkoxy; $C_{6-12}$-aryloxy; $C_{5-12}$-heteroaryloxy; $C_{7-12}$-arylalkyloxy; $C_{6-12}$-heteroaralkyloxy; optionally substituted phenoxy; —(CH₂)m-(Z)n-(CO)—R$^f$ and —(CH₂)m-(Z)n-SO₂—(NR$^g$)n'-R$^f$, where m, n and n' are each independently 0 or 1;

R³ is $C_{1-12}$-alkoxy;

R⁵ is hydrogen;

Z is O or NR$^g$;

R$^f$ is selected from hydrogen, $C_{1-12}$-alkyl, hydroxy, $C_{1-12}$-alkoxy, amino, $C_{1-12}$-hydroxyalkyl and $C_{2-12}$-alkoxyalkyl;

each R$^g$ is independently hydrogen or $C_{1-12}$-alkyl;

or alternatively, R³ and R⁴ together with the atoms to which they are attached form a five or six-membered ring that optionally includes one or two heteroatoms independently selected from O, S and N;

or alternatively, R² and R³ together form an alkylene dioxy; or R² and R³ together with the atoms to which they are attached may form a five or six-membered ring that optionally includes one or two heteroatoms independently selected from O, S and N;

R⁶ is selected from hydrogen and $C_{1-12}$-alkyl; and

R⁷ is selected from hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalkyl; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{3-12}$-hydroxyalkyloxycarbonylalkyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

2. The compound of claim 1, or a pharmaceutically acceptable salt thereof, wherein X₁ is CR² and W is S, providing compounds of Formula 1a as follows:

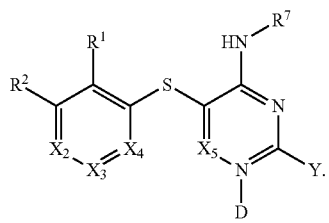

Formula 1a

3. The compound of claim 1, or a pharmaceutically acceptable salt thereof, wherein X₁ is N, providing compounds of the Formula 1b, as follows:

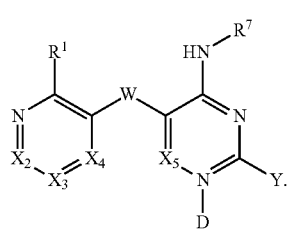

Formula 1b

4. The compound of claim 1, or a pharmaceutically acceptable salt thereof, wherein X₅ is CR⁶, providing compounds of Formula 1m, as follows:

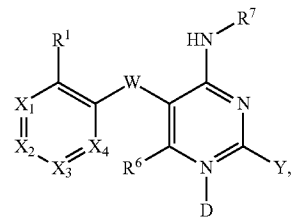

Formula 1m provided, however, when X₁ is CR², W is not O.

5. The compound of claim 1, or a pharmaceutically acceptable salt thereof, wherein X₂ and X₃ of Formula I are each C—OMe, providing compounds of Formula 1n, as follows:

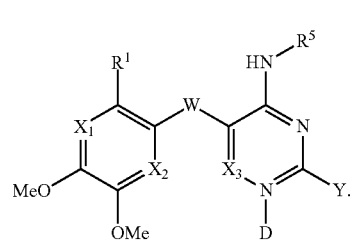

Formula 1n

6. The compound of claim 1, or a pharmaceutically acceptable salt thereof, wherein W is O.

7. The compound of claim 1, or a pharmaceutically acceptable salt thereof, wherein W is S.

8. The compound of claim 1 of Formula 2, or a pharmaceutically acceptable salt thereof:

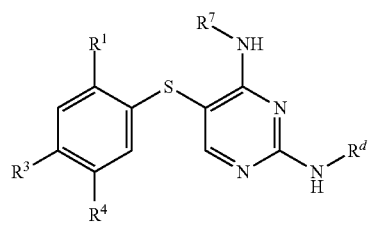

Formula 2 wherein:

R¹ is $C_{1-12}$-alkyl;

R³ is $C_{1-12}$-alkoxy;

R⁴ is: hydrogen; $C_{1-12}$-alkyl; $C_{2-12}$-alkenyl; $C_{2-12}$-alkynyl; amino; halo; amido; $C_{1-12}$-haloalkyl; $C_{1-12}$-alkoxy; hydroxy; $C_{1-12}$-haloalkoxy; nitro; $C_{1-12}$-hydroxyalkyl; $C_{2-12}$-alkoxyalkyl; $C_{1-12}$-hydroxyalkoxy; $C_{3-12}$-alkynylalkoxy; $C_{2-12}$-alkylsulfonyl; $C_{6-12}$-arylsulfonyl; cyano; $C_{6-12}$-aryl; $C_{5-12}$-heteroaryl; $C_{3-12}$-heterocyclyl; $C_{4-12}$-heterocyclylalkoxy; $C_{6-12}$-aryloxy; $C_{5-12}$-heteroaryloxy; $C_{7-12}$-arylalkyloxy; $C_{6-12}$-heteroarylalkyloxy; optionally substituted phenoxy; —(CH₂)m-(Z)n-(CO)—R$^f$ or —(CH₂)m-(Z)n-SO₂—(NR$^g$)n'-R$^f$, where m, n and n' are each independently 0 or 1;

Z is O or NR$^g$;

R$^f$ is hydrogen, $C_{1-12}$-alkyl, hydroxy, $C_{1-12}$-alkoxy, amino, $C_{1-12}$-hydroxyalkyl or $C_{2-12}$-alkoxyalkyl;

each R$^g$ is independently hydrogen or $C_{1-12}$-alkyl;

or alternatively, R³ and R⁴ together with the atoms to which they are attached may form a five or six-membered ring that optionally includes one or two heteroatoms independently selected from O, S and N;

$R^7$ is selected from hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalkyl; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl; and $R^d$ is selected from hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

9. A compound of Formula 3, or a pharmaceutically acceptable salt thereof:

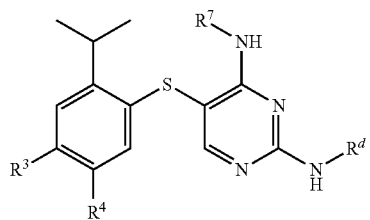

Formula 3 wherein:

$R^3$ is $C_{1-12}$-alkoxy;

$R^4$ is: hydrogen; $C_{1-12}$-alkyl; $C_{2-12}$-alkenyl; $C_{2-12}$-alkynyl; amino; halo; amido; $C_{1-12}$-haloalkyl; $C_{1-12}$-alkoxy; hydroxy; $C_{1-12}$-haloalkoxy; nitro; $C_{1-12}$-hydroxyalkyl; $C_{2-12}$-alkoxyalkyl; $C_{1-12}$-hydroxyalkoxy; $C_{3-12}$-alkynylalkoxy; $C_{1-12}$-alkylsulfonyl; $C_{6-12}$-arylsulfonyl; cyano; $C_{6-12}$-aryl; $C_{5-12}$-heteroaryl; $C_{3-12}$-heterocyclyl; $C_{4-12}$-heterocyclylalkoxy; $C_{6-12}$-aryloxy; $C_{5-12}$-heteroaryloxy; $C_{7-12}$-arylalkyloxy; $C_{6-12}$-heteroaralkyloxy; optionally substituted phenoxy; or —(CH$_2$)m-(Z)n-(CO)—R$^f$ or —(CH$_2$)m-(Z)n-SO$_2$—(NR$^g$)n'-R$^f$, where m, n and n' are each independently 0 or 1;

Z is O or NR$^g$;

$R^f$ is hydrogen, $C_{1-12}$-alkyl, hydroxy, $C_{1-12}$-alkoxy, amino, $C_{1-12}$-hydroxyalkyl or $C_{2-12}$-alkoxyalkyl, and each R$^g$ is independently hydrogen or $C_{1-12}$-alkyl;

or alternatively, $R^3$ and $R^4$ together with the atoms to which they are attached may form a five or six-membered ring that optionally includes one or two heteroatoms independently selected from O, S and N;

$R^7$ is selected from: hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl; and $R^d$ is selected from: hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

10. The compound of claim 1 of Formula 4, or a pharmaceutically acceptable salt thereof:

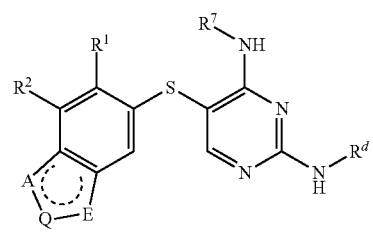

Formula 4 wherein:

$R^1$ is $C_{1-12}$-alkyl;

$R^2$ is hydrogen; $C_{1-12}$-alkyl; $C_{2-12}$-alkenyl; $C_{2-12}$-alkynyl; amino; halo; amido; $C_{1-12}$-haloalkyl; $C_{1-12}$-alkoxy; hydroxy; $C_{1-12}$-haloalkoxy; nitro; $C_{1-12}$-hydroxyalkyl; $C_{2-12}$-alkoxyalkyl; $C_{1-12}$-hydroxyalkoxy; $C_{3-12}$-alkynylalkoxy; $C_{1-12}$-alkylsulfonyl; $C_{6-12}$-arylsulfonyl; cyano; $C_{6-12}$-aryl; $C_{5-12}$-heteroaryl; $C_{3-12}$-heterocyclyl; $C_{4-12}$-heterocyclylalkoxy; $C_{6-12}$-aryloxy; $C_{5-12}$-heteroaryloxy; $C_{7-12}$-arylalkyloxy; $C_{6-12}$-heteroarylalkyloxy; optionally substituted phenoxy; or —(CH$_2$)m-(Z)n-(CO)—R$^f$ or —(CH$_2$)m-(Z)n-SO$_2$—(NR$^g$)n'-R$^f$, where m, n and n' are each independently 0 or 1;

Z is O or NR$^g$;

$R^f$ is hydrogen, $C_{1-12}$-alkyl, hydroxy, $C_{1-12}$-alkoxy, amino, $C_{1-12}$-hydroxyalkyl or $C_{2-12}$-alkoxyalkyl, and each R$^g$ is independently hydrogen or $C_{1-12}$-alkyl;

$R^7$ is selected from: hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl;

$R^d$ is selected from: hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl;

Q is (CR$^9$)x, one of A and E is O, S or NR$^{10}$ and the other is (CR$^9$)x or N, wherein each x is independently 1 or 2;

or alternatively, Q is N, one of A and E is NR$^{10}$ and the other is (CR$^9$)x;

each R$^9$ is independently hydrogen, $C_{1-12}$-alkyl, halo or $C_{1-12}$-alkoxy; and R$^{10}$ is hydrogen, $C_{1-12}$-alkyl, $C_{1-12}$-hydroxyalkyl, $C_{2-12}$-alkoxyalkyl, —(CH$_2$)m-(Z)n-(CO)—R$^f$, or —(CH$_2$)m-(Z)n-SO$_2$—(NR$^g$)n'-R$^f$.

11. The compound of claim 1 of Formula 5, or a pharmaceutically acceptable salt thereof:

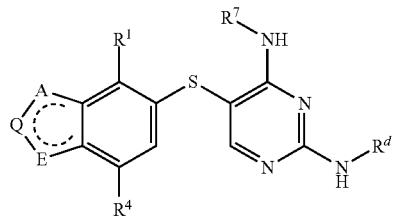

Formula 5 wherein:
- $R^1$ is: $C_{1-12}$-alkyl;
- $R^4$ is: hydrogen; $C_{1-12}$-alkyl; $C_{2-12}$-alkenyl; $C_{2-12}$-alkynyl; amino; halo; amido; $C_{1-12}$-haloalkyl; $C_{1-12}$-alkoxy; hydroxy; $C_{1-12}$-haloalkoxy; nitro; $C_{1-12}$-hydroxyalkyl; $C_{2-12}$-alkoxyalkyl; $C_{1-12}$-hydroxyalkoxy; $C_{3-12}$-alkynylalkoxy; $C_{1-12}$-alkylsulfonyl; $C_{6-12}$-arylsulfonyl; cyano; $C_{6-12}$-aryl; $C_{5-12}$-heteroaryl; $C_{3-12}$-heterocyclyl; $C_{4-12}$-heterocyclylalkoxy; $C_{6-12}$-aryloxy; $C_{5-12}$-heteroaryloxy; $C_{7-12}$-arylalkyloxy; $C_{6-12}$-heteroarylalkyloxy; optionally substituted phenoxy; or —(CH$_2$)m-(Z)n-(CO)—R$^f$ or —(CH$_2$)m-(Z)n-SO$_2$—(NR$^g$)n'-R$^f$, where m, n and n' are each independently 0 or 1;
- Z is O or NR$^g$;
- R$^f$ is hydrogen, $C_{1-12}$-alkyl, hydroxy, $C_{1-12}$-alkoxy, amino, $C_{1-12}$-hydroxyalkyl or $C_{2-12}$-alkoxyalkyl;
- each R$^g$ is independently hydrogen or alkyl;
- $R^7$ is selected from hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl;
- R$^d$ is selected from: hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl;
- Q is (CR$^9$)x, one of A and E is O, S or NR$^{10}$ and the other is (CR$^9$)x or N, wherein each x is independently 1 or 2; or alternatively, Q is N, one of A and E is NR$^{10}$ and the other is (CR$^9$)x;
- each R$^9$ is independently hydrogen, $C_{1-12}$-alkyl, halo or $C_{1-12}$-alkoxy; and
- R$^{10}$ is hydrogen, $C_{1-12}$-alkyl, $C_{1-12}$-hydroxyalkyl, $C_{2-12}$-alkoxyalkyl, —(CH$_2$)m-(Z)n-(CO)—R$^f$, or —(CH$_2$)m-(Z)n-SO$_2$—(NR$^g$)n'-R$^f$.

12. A method for treating a disease mediated by a P2X3 receptor antagonist, a P2X2/3 receptor antagonist, or both, said method comprising administering to a subject in need thereof an effective amount of a compound of claim 1, or a pharmaceutically acceptable salt thereof.

13. The compound of claim 2, or a pharmaceutically acceptable salt thereof, wherein $X_5$ is CH.

14. The compound of claim 6, or a pharmaceutically acceptable salt thereof, wherein $X_5$ is CH.

15. A compound of claim 1, or a pharmaceutically acceptable salt thereof, selected from:

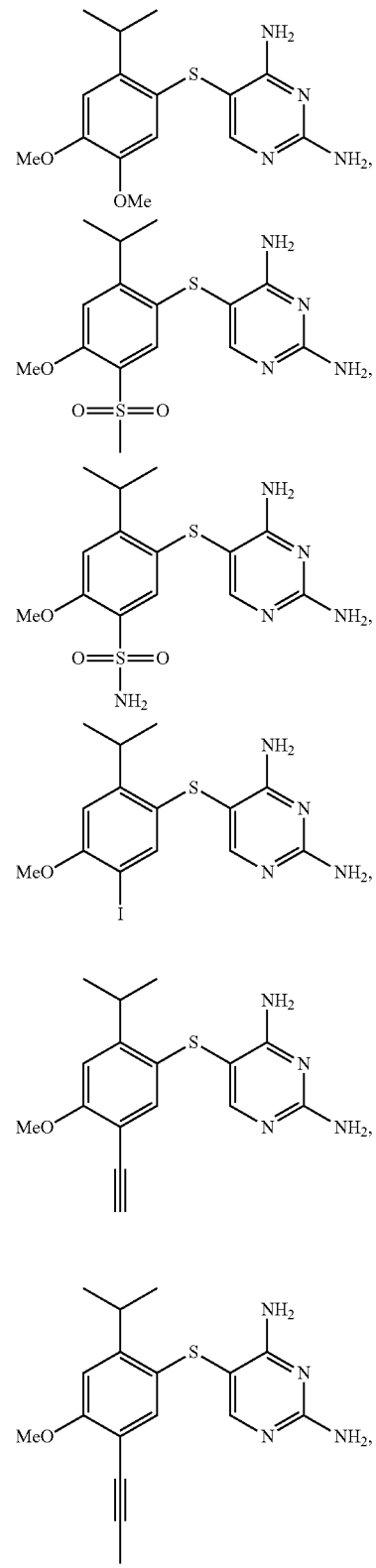

151
-continued
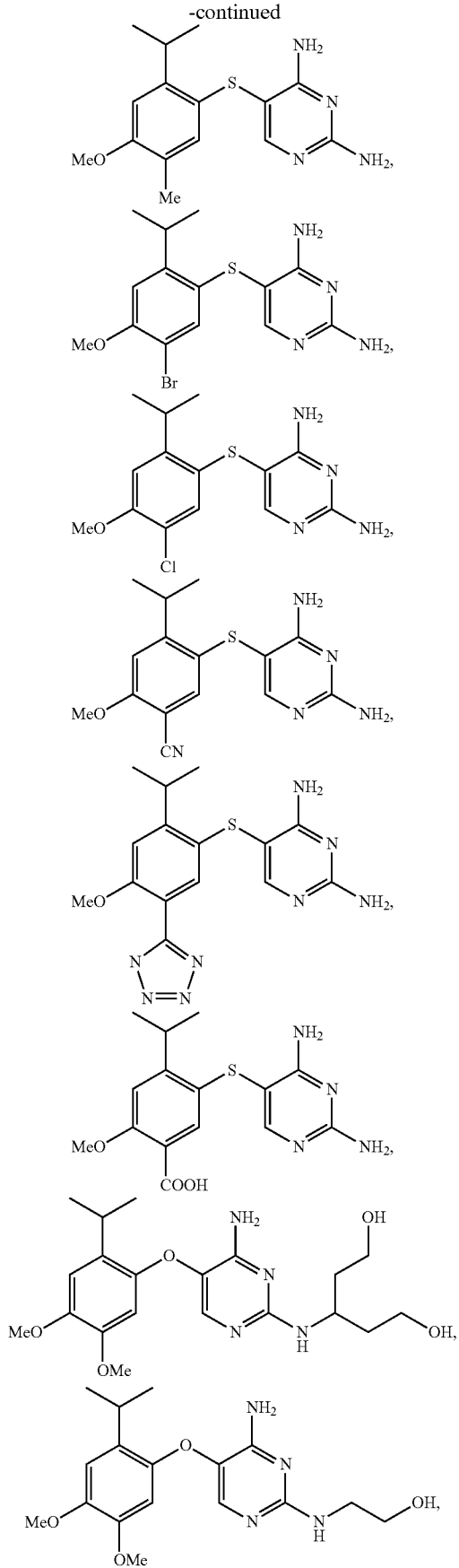
152
-continued
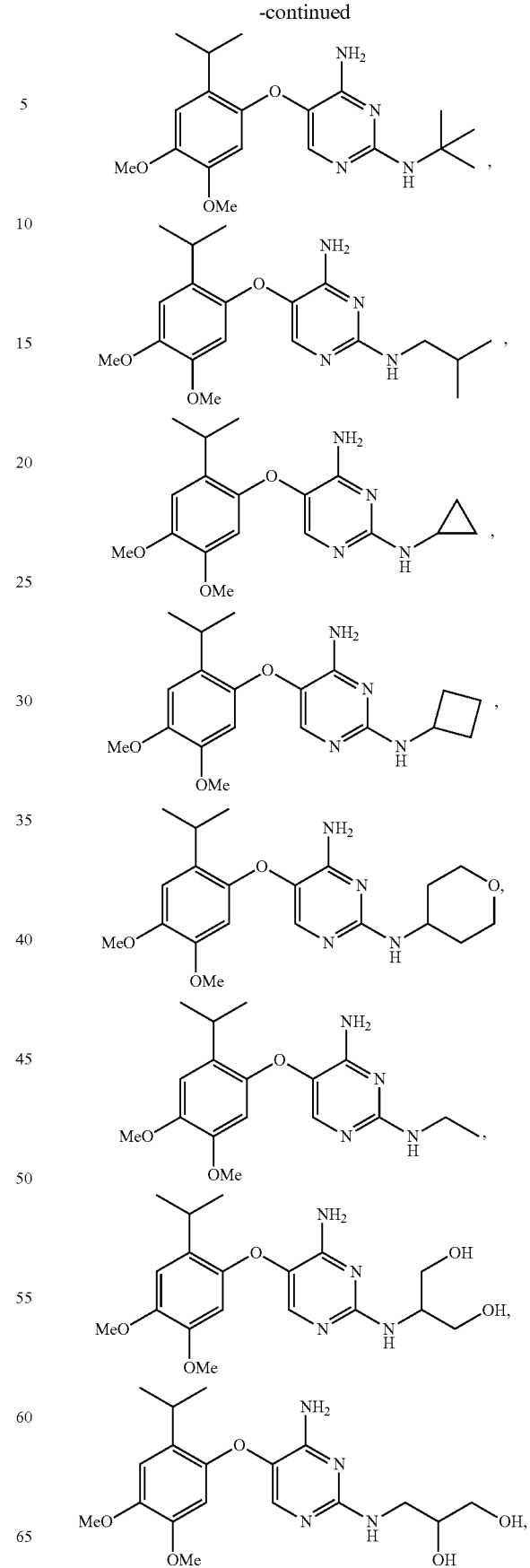

153
-continued
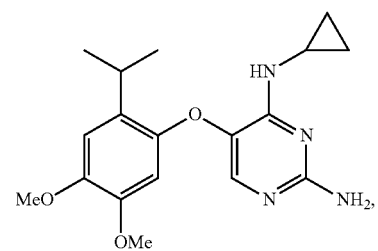
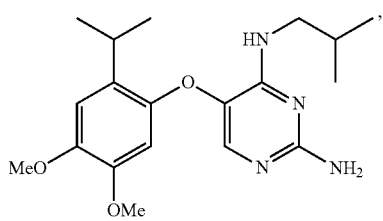
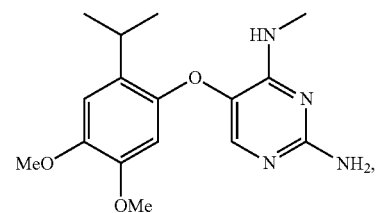
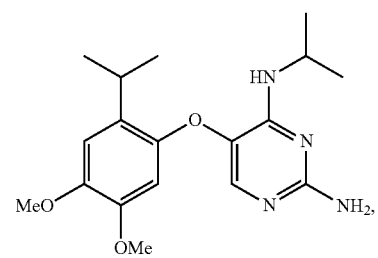
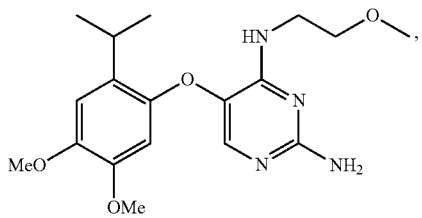
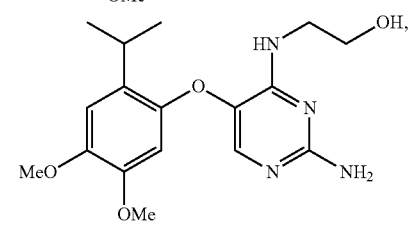
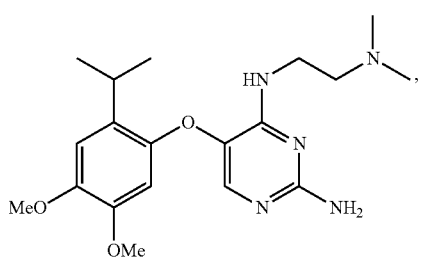
154
-continued
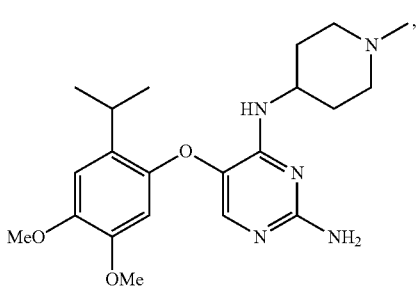
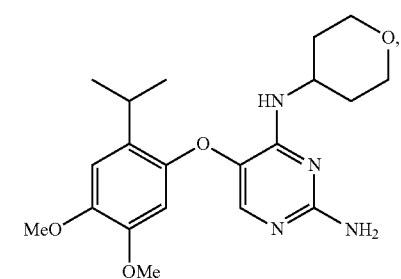
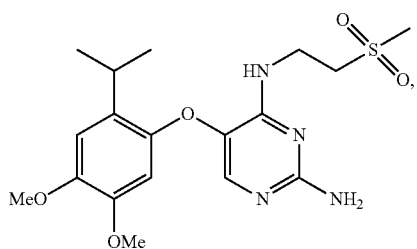
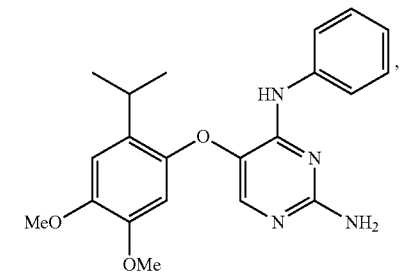
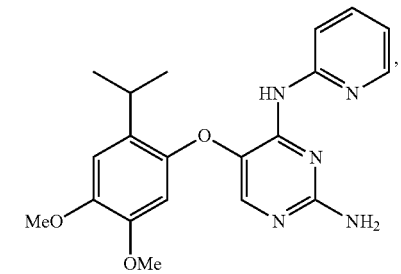

-continued
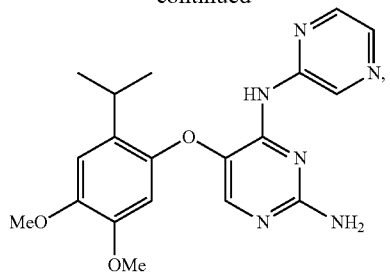
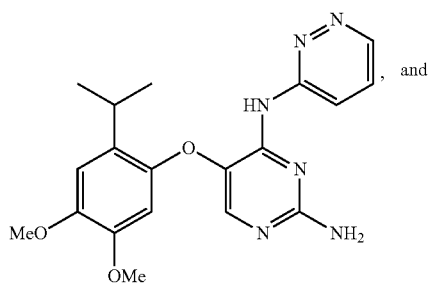
-continued
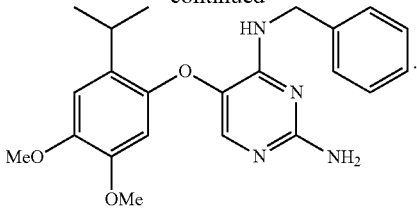
16. A compound of the following structure, or a pharmaceutically acceptable salt thereof:
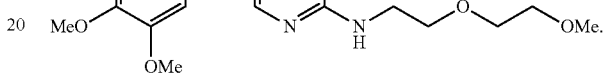
* * * * *